(12) United States Patent
Hijazi et al.

(10) Patent No.: US 11,491,186 B2
(45) Date of Patent: Nov. 8, 2022

(54) HUMAN BLOOD-DERIVED PRODUCTS HAVING DECREASED FIBRINOLYTIC ACTIVITY AND USES THEREOF IN HEMOSTATIC DISORDERS

(71) Applicant: PLAS-FREE LTD, Nazareth (IL)

(72) Inventors: Abd Alrauf Hijazi, D.N. Shimshon (IL); Muhamed Higazi, D.N. Shimshon (IL)

(73) Assignee: PLAS-FREE LTD, Nazareth (IL)

( * ) Notice: Subject to any disclaimer, the term of this patent is extended or adjusted under 35 U.S.C. 154(b) by 0 days.

(21) Appl. No.: 16/329,985

(22) PCT Filed: Aug. 31, 2017

(86) PCT No.: PCT/IL2017/050977
§ 371 (c)(1),
(2) Date: Mar. 1, 2019

(87) PCT Pub. No.: WO2018/042438
PCT Pub. Date: Mar. 8, 2018

(65) Prior Publication Data
US 2019/0192564 A1   Jun. 27, 2019

Related U.S. Application Data

(60) Provisional application No. 62/382,344, filed on Sep. 1, 2016.

(51) Int. Cl.
| | |
|---|---|
| *A61K 35/16* | (2015.01) |
| *A61K 38/36* | (2006.01) |
| *A61P 17/02* | (2006.01) |
| *A61K 35/14* | (2015.01) |
| *C12N 9/68* | (2006.01) |
| *C07K 1/22* | (2006.01) |
| *C12N 9/72* | (2006.01) |

(52) U.S. Cl.
CPC ............ *A61K 35/16* (2013.01); *A61K 35/14* (2013.01); *A61K 38/36* (2013.01); *A61K 38/363* (2013.01); *A61P 17/02* (2018.01); *C07K 1/22* (2013.01); *C12N 9/6435* (2013.01); *C12N 9/6459* (2013.01); *C12Y 304/21007* (2013.01); *C12Y 304/21068* (2013.01)

(58) Field of Classification Search
CPC ........ A61K 35/16; A61K 38/36; A61K 35/14; A61K 38/363; A61P 17/02; C12Y 304/21068; C12Y 304/21007; C12N 9/6435; C12N 9/6459; C07K 1/22
See application file for complete search history.

(56) References Cited

U.S. PATENT DOCUMENTS

| | | | |
|---|---|---|---|
| 3,998,946 A | 12/1976 | Condie et al. | |
| 4,578,056 A | 3/1986 | King et al. | |
| 7,125,569 B2 | 10/2006 | Nur et al. | |
| 10,188,706 B2 | 1/2019 | Higazi et al. | |
| 2003/0124703 A1 | 7/2003 | Nur et al. | |
| 2010/0203033 A1* | 8/2010 | Nur ........................ | A61L 24/106 424/94.63 |
| 2010/0310524 A1* | 12/2010 | Bechor .............. | A61K 38/1709 435/375 |
| 2014/0154233 A1* | 6/2014 | Pham .................. | C07K 14/745 424/94.64 |
| 2016/0000823 A1 | 1/2016 | Emanuele et al. | |
| 2016/0058937 A1 | 3/2016 | Gaitas et al. | |

FOREIGN PATENT DOCUMENTS

| | | |
|---|---|---|
| CN | 104602701 A | 5/2015 |
| EP | 0 156 496 A1 | 2/1985 |
| WO | 01/37900 A2 | 5/2001 |
| WO | 02/072234 A1 | 9/2002 |
| WO | 02/095019 A1 | 11/2002 |
| WO | 03/007873 A2 | 1/2003 |
| WO | 03/039588 A1 | 5/2003 |
| WO | 2013/001524 A1 | 1/2013 |
| WO | 2013/070809 A2 | 5/2013 |

OTHER PUBLICATIONS

H. Atrah. Fibrin Glue. BMJ (1994), 308(9), 933-934. (Year: 1994).*
Law et al. New insights into the structure and function of the plasminogen/plasmin system. Current Opinion in Structural Biology (2013), 23, 836-841 (Year: 2013).*
Abdel-Wahab, et al.. Effect of fresh-frozen plasma transfusion on prothrombin time and bleeding in patients with mild coagulation abnormalities, Transfusion, Aug. 2006, pp. 1279-1285, vol. 46.
EVICEL Fibrin Sealant provides sustained hemostasis, demonstrated in high risk patients, with effective clot formation regardless of patient coagulation profile, EVICEL Fibrin Sealant (Human), Ethicon part of the Johnson & Johnson Family of Companies, 2017, pp. 1-5.
Higazi, et al., Lysis of Plasma Clots of Urokinase-Soluble Urokinase Receptor Complexes, Blood, Sep. 15, 1998, pp. 2075-2083, vol. 92, No. 6.
Hijazi, et al., Endogenous plasminogen activators mediate progressive intracerebral hemorrhage after traumatic brain injury in mice. Blood, Apr. 16, 2015, pp. 2558-2567, vol. 125(16).
Holland, et al., The Effect of Plasma Transfusion on Coagulation Test Results, Am. J. Clin Pathol., 2006, pp. 133-139, vol. 126.
Iwamoto, Abstract Only, Plasminogen-plasmin system IX. Specific binding of tranexamic acid to plasmin, Thromb. Diath. Haemorrh., Jun. 30, 1975, pp. 573-585, vol. 33(3).

(Continued)

*Primary Examiner* — Sean C. Barron
(74) *Attorney, Agent, or Firm* — Browdy and Neimark, PLLC

(57) ABSTRACT

The present invention provides therapeutic products with decreased fibrinolytic activity of t-PA-deficient and/or plasminogen-deficient blood products, as well as compositions, kits and methods using the same in treating bleeding associated with hereditary or acquired bleeding disorders. The invention further provides extracorporeal apparatus for blood or blood products Plasmapheresis aimed to prevent or treat bleeding disorders.

34 Claims, 10 Drawing Sheets

(56) References Cited

OTHER PUBLICATIONS

Lund, et al., Plasminogen activation independent of uPA and tPA maintains wound healing in gene-deficient mice, The EMBO Journal, 2006, pp. 2686-2697, vol. 25.

Meheux, et al., Efficacy of Intra-articular Platelet-Rich Plasma Injections in Knee Osteoarthritis: A Systematic Review, Arthroscopy: The Journal of Arthroscopic and Related Surgery, Mar. 2016, pp. 495-505, vol. 32, No. 3.

Pap, et al., Expression of Stromelysin and Urokinase Type Plasminogen Activator Protein in Resection Specimens and Biopsies at Different Stages of Osteoarthritis of the Knee, Pathology Research and Practice, 2000, pp. 219-226, vol. 196.

Pleines, et al., Megakaryocyte-specific RhoA deficiency causes macrothrombocytopenia and defective platelet activation in hemostasis and thrombosis, Blood, Jan. 26, 2012, pp. 1054-1063, vol. 119, No. 4.

Seligsohn, et al., Classification, Clinical Manifestations, and Evaluation of Disorders of Hemostasis, Williams Hematology, Ed. James Shanahan and Harriet Lebowitz, McGraw-Hill Books, 2010, pp. 1-13, Eighth Edition, chapter 18.

Plasminogen Removal, GE Healthcare Life Sciences, Data File 28-9168-16 AB, 2 pages (2012).

Kraut et al., Metabolic acidosis: pathophysiology, diagnosis and management, Nat. Rev. Neuphrol., 6:274-285 (2010).

Kalarickal, et al., TranexamicAcid. In Essence of Anesthesia Practice (p. 651). WB Saunders. 2011.

Tinawi, Pathophysiology, Evaluation, and Management of Metabolic Alkalosis, Cureus, 13(1):e12841. DOI 10.7759/cureus. 12841 (2021).

Strijks et al.. Pathophysiology, Evaluation, and Management of Metabolic Alkalosis as Intracranial Haematoma in Infancy. Neuropediatrics, 30:320-324 (1999).

* cited by examiner

HUMAN BLOOD-DERIVED PRODUCTS HAVING DECREASED FIBRINOLYTIC ACTIVITY AND USES THEREOF IN HEMOSTATIC DISORDERS

FIELD OF THE INVENTION

The present invention pertains to the field of coagulation and transfusion medicine. More specifically, the present invention provides specific blood-derived products that are devoid in fibrinolytic activity, methods and uses thereof.

BACKGROUND ART

References considered to be relevant as background to the presently disclosed subject matter are listed below.
Selighson U et al. Classification, Clinical Manifestations & Evaluation of Disorders of Hemostasis. In: Williams Hematology, $8^{th}$ ed, 2010, pp 2322-2330.
Abdel-Wahab O I et al. Effect of fresh-frozen plasma transfusion on prothrombin time and bleeding in patients with mild coagulation abnormalities. Transfusion 2006; 46: 1279-1285.
Holland L L et al. Toward rational fresh frozen plasma transfusion: The effect of plasma transfusion on coagulation test results. Am J Clin Pathol 2006; 126: 133-139.
Hijazi N et al. Endogenous plasminogen activators mediate progressive intracerebral hemorrhage after traumatic brain injury in mice. Blood, 2015, 125:2558-2567.
Pleines I et al. Megakaryocyte-specific RhoA deficiency causes macrothrombocytopenia and defective platelet activation in hemostasis and thrombosis. Blood 2012 119:1054-1063.
Higazi A A et al. Lysis of plasma clots by urokinase-soluble urokinase receptor complexes. Blood, 1998, 92:2075-2083.
Meheux C J et al. Efficacy of Intra-articular Platelet-Rich Plasma Injections in Knee Osteoarthritis: A Systematic Review. Arthroscopy, 2016, 32, 495-505.
Pap G et al. Expression of stromelysin and urokinase type plasminogen activator protein in resection specimens and biopsies at different stages of osteoarthritis of the knee. Pathol. Res. Pract. 2000, 196: 219-226.
U.S. Pat. No. 7,125,569.
U.S. Pat. No. 3,998,946.
Acknowledgement of the above references herein is not to be inferred as meaning that these are in any way relevant to the patentability of the presently disclosed subject matter.

BACKGROUND OF THE INVENTION

Normal hemostasis is a very delicately balanced system. When it functions as it should, the blood is maintained in a fluid state in the vasculature, yet rapidly clots when the need to seal an injury arrives. In the 1960s, two groups proposed a model for clot formation that envisaged a sequential series of steps in which activation of one clotting (coagulation) factor led to the activation of another, finally leading to a clot formation. When these coagulation factors by sequential activation cause formation of the clot, the counterpart system, called fibrinolytic system, is further activated to become a cause of dissolution (lysis) of the clot. This fibrinolytic system comprises of anti-clotting proteins (plasminogen activator, plasminogen and plasmin), which following sequential activation lead to lysis of the clot (Selighson U et al.).

The failure of hemostatic function due to coagulation factors deficiency causes impairment (or lack) in clot formation. Likewise, the result of an excessive fibrinolytic activity results in rapid and unwarranted dissolution of the formed clot. On the other hand, over stimulation of the coagulation cascade or inhibition of the fibrinolytic system would cause the formation of pathological clots. Thus, the outcome of the failure of each one of the above systems could be bleeding or increased coagulation tendency.

Replacement therapy is effective in treating bleeding disorders, however this treatment may not be sufficient. Fresh-frozen plasma (FFP) is frequently transfused to bleeding patients or patients with prolongation of coagulation tests under the assumption that it will improve hemostasis and will correct and/or prevent bleeding. The effect of FFP on coagulation parameters such as prothrombin time (PT) and international normalized ratio (INR) was examined in a prospective audit performed at Massachusetts General Hospital (Abdel-Wahab O I et al.). The data showed that transfusion of FFP in this setting failed to correct the PT in 99% of patients and in only 15% of patients was INR corrected by at least halfway to normal.

Similarly, Holland et al. reported that FFP failed to change INR over time. They hypothesized that failure of FFP to correct INR results from the dilution of the coagulation factors present in the infused FFP by recipient plasma.

FFP contains all components (proteins) of the coagulation and fibrinolytic systems, thus being in theory suitable for the treatment of bleeding in patients with hereditary or acquired coagulation factor deficiencies. In addition, this product is supposed to prevent bleeding in subjects with coagulopathy before, during and after surgical procedures. However, since these plasma derived products contain in addition to coagulation factors fibrinolytic proteins, they have a potential to induce undesired lysis (dissolution) of the hemostatic clot formed during and following the replacement of coagulation factors of the product.

U.S. Pat. No. 3,998,946 discloses methods for treating blood plasma or related products with fumed colloidal silica to remove fibrinogen without polymerization to fibrin, plasminogen and plasmin and other compounds but retain coagulation factor II. As being devoid of fibrinogen, the resulting product cannot support clot formation and as such, cannot be used for the treatment of bleeding and hemostatic disorders.

U.S. Pat. No. 7,125,569, and its corresponding applications and patents disclose specific methods using a very particular resin for removal of only plasmin(ogen) from protein mixture/s. The resulting products were produced for the purpose of preparing plasmin(ogen) free fibrinogen for use as a biological glue. However, the resulting mixtures still contain tPA and as such, clearly exhibit fibrinolytic activity. More specifically, the tPA present in the product activated the plasminogen in the treated area, thereby leading to cleavage of the newly formed fibrin net. Plasminogen is normally present at high concentrations in the blood (about 2 µM), therefore, any blood leakage during any surgical intervention increases the plasminogen concentration in the extra vascular area. Furthermore, in case such glue is applied on the injured blood vessels during surgical intervention, the tPA present in the biological glue may contact the plasminogen present in the blood and by that, may activate the fibrinolytic cascade. Thus, the plasminogen-free products disclosed in U.S. Pat. No. 7,125,569 may be used only for topical applications as a biological glue, and are irrelevant for systemic use in transfusion or for treating bleeding associated with fibrinolytic or thrombolytic therapy.

Thus, a long-felt need exists, specifically for product/s containing coagulation factors but at the same time missing fibrinolytic proteins that are suitable for transfusion and systemic use. This need, identified by the inventor, for a safe and efficient hemostatic product led the inventors to develop novel different products with a decreased fibrinolytic activity that are applicable for systemic as well as for topical uses.

SUMMARY OF THE INVENTION

In a first aspect, the invention relates to a blood and/or blood-derived product that has a reduced fibrinolytic activity. The product of the invention comprises at least one coagulation factor. In some embodiments, the product of the invention may be a tissue plasminogen activator (tPA)-deficient and/or is devoid of plasminogen or plasmin activity. In some specific embodiments, the product of the invention is a t-PA-deficient and/or plasminogen-deficient blood or blood-derived product. In yet some further embodiments, the product of the invention may be a t-PA-deficient blood or blood-derived product. In some other specific embodiments, the product of the invention may be a plasminogen-deficient blood or blood-derived product. In yet some further specific embodiments, the product of the invention may be a t-PA-deficient and plasminogen-deficient blood or blood-derived product.

The invention further provides a composition comprising as an active ingredient a therapeutically effective amount of a blood and/or blood-derived product that has a reduced fibrinolytic activity. More specifically, the product comprises at least one coagulation factor. In some embodiments the product may be a tPA-deficient and/or is devoid of plasminogen or plasmin activity. Optionally, the composition of the invention may further comprise at least one of pharmaceutically acceptable carrier/s, excipient/s, additive/s diluent/s and adjuvant/s.

In another aspect, the invention relates to a biological glue or sealant comprising a blood and/or blood-derived product that display or has a reduced fibrinolytic activity, the product comprises at least one coagulation factor. In some embodiments, the product comprised within the biological glue of the invention may be a tPA-deficient and/or is devoid of plasminogen or plasmin activity. More specifically, the product may be at least one of t-PA-deficient and/or plasminogen-deficient fresh plasma (FP), t-PA-deficient and/or plasminogen-deficient platelets reach plasma (PRP), t-PA-deficient and/or plasminogen-deficient fresh frozen plasma (FFP), and t-PA-deficient and/or plasminogen-deficient cryoprecipitate.

A further aspect of the invention relates to a method for the treatment, prophylaxis, amelioration, inhibition or delaying the onset of bleeding, hemostatic disorders and any bleeding or pathologic condition associated therewith in a subject in need thereof. More specifically, the method of the invention may comprise the step of administering to said subject a therapeutically effective amount of at least one blood and/or blood-derived product that has a reduced fibrinolytic activity and comprise at least one coagulation factor, or of any composition or biological glue or sealant comprising the same. The product used by the method of the invention may be a tPA-deficient and/or may be devoid of plasminogen or plasmin activity.

In a further aspect the invention encompasses a blood and/or blood-derived product that has a reduced fibrinolytic activity or any composition or glue or sealant thereof for use in the treatment, prevention prophylaxis, amelioration, inhibition or delaying the onset of bleeding, hemostatic disorders and any bleeding or pathologic condition associated therewith in a subject in need thereof. The product of the invention may comprise at least one coagulation factor. Still further, the product of the invention may be a tPA-deficient and/or may be devoid of plasminogen or plasmin activity.

In a further aspect, the invention provides a kit comprising at least one blood and/or blood-derived product that has a reduced fibrinolytic activity, in accordance with the invention; and at least one coagulation promoting agent. The product used by the kit of the invention may comprise at least one coagulation factor. Still further, the product of the invention may be a tPA-deficient and/or may be devoid of plasminogen or plasmin activity. The product use by the kit of the invention may be at least one of t-PA-deficient and/or plasminogen-deficient whole blood, t-PA-deficient and/or plasminogen-deficient FP, t-PA-deficient and/or plasminogen-deficient PRP, t-PA-deficient and/or plasminogen-deficient FFP, and t-PA-deficient and/or plasminogen-deficient cryoprecipitate.

Yet further, the invention discloses a method for the preparation of at least one blood and/or blood-derived product that has a reduced fibrinolytic activity. The product prepared by the method of the invention may comprise at least one coagulation factor. Still further, the product of the invention may be a tPA-deficient and/or may be devoid of plasminogen or plasmin activity. More specifically, the method comprising the steps of subjecting whole blood or blood-derived product comprising at least one coagulation factor to affinity-depletion procedure specific for at least one of t-PA and plasminogen; and recovering the t-PA-deficient and plasminogen-deficient blood-derived product obtained in the earlier step.

Additional aspect of the invention provides a method for performing an extracorporeal procedure in a subject in need thereof. The method comprising the steps of transferring the blood of the subject into an extracorporeal apparatus; subjecting said blood to affinity depletion procedure specific for t-PA and/or plasminogen. The depletion may be performed before, during or after blood is being transferred into and out-off said apparatus, thereby obtaining an extracorporeal t-PA-deficient and/or plasminogen-deficient blood or plasma of said subject. The next step involves returning the t-PA-deficient and/or plasminogen-deficient blood or plasma obtained in the above step to said subject.

In yet another aspect, the invention provides an extracorporeal apparatus for blood and blood product/s pheresis. The apparatus of the invention may comprise or coated, at least in part, by tranexamic acid that specifically binds at least one of tPA and/or plasminogen.

These and further aspects of the invention will become apparent by the hand of the following description.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

The figure presents a schematic structure of a solid support or matrix, specifically, magnetic beads conjugated to Tranexamic acid (TXA).

Figure 2:
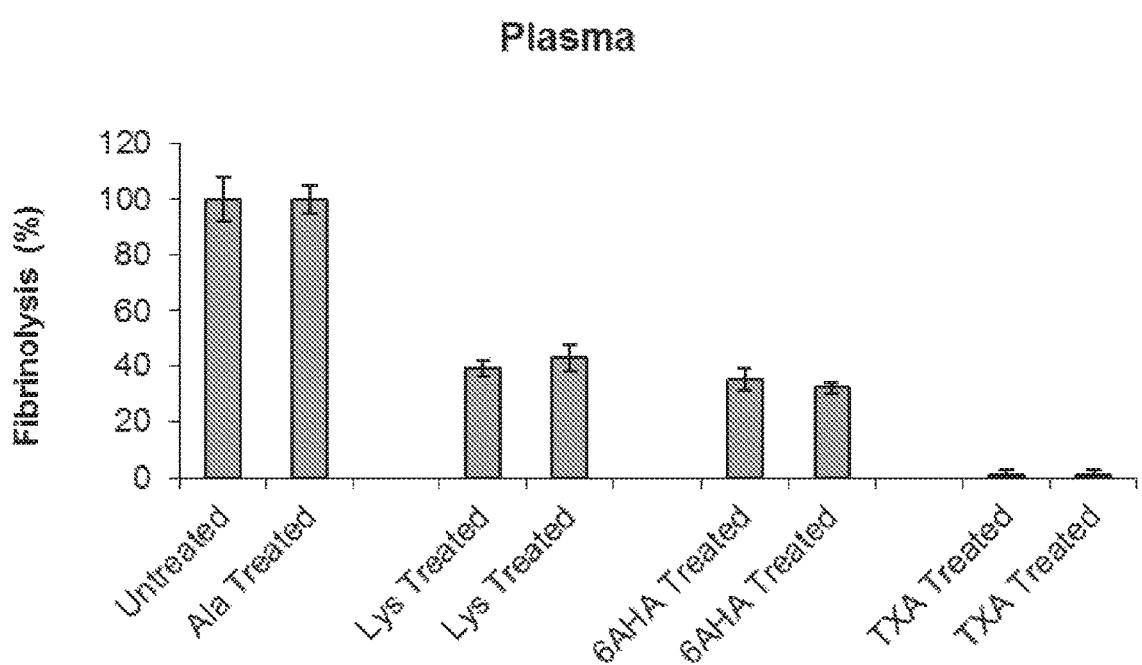

FIG. 2. Pretreating of human plasma with magnetic beads coated with lysine or lysine analogs inhibits fibrinolysis t-PA-deficient and/or Plasminogen-depleted plasma was generated from FFP by incubation with either lysine (Lys Treated), 6-Aminohexanoic-Acid (6AHA Treated) or tranexamic acid (TXA Treated) coated beads flowed by submitting the FFP to magnetic field and separating the FFP free beads, as detailed in Experimental procedures. Plasma clots were formed by adding thrombin (Higazi A A et al. 1998). Following the addition of tPA (10 nM), the lysis of plasma clots was measured and presented as a percent of fibrinolysis relative to that observed in untreated plasma or plasma treated with alanine coated beads (negative controls).

Figure 3:
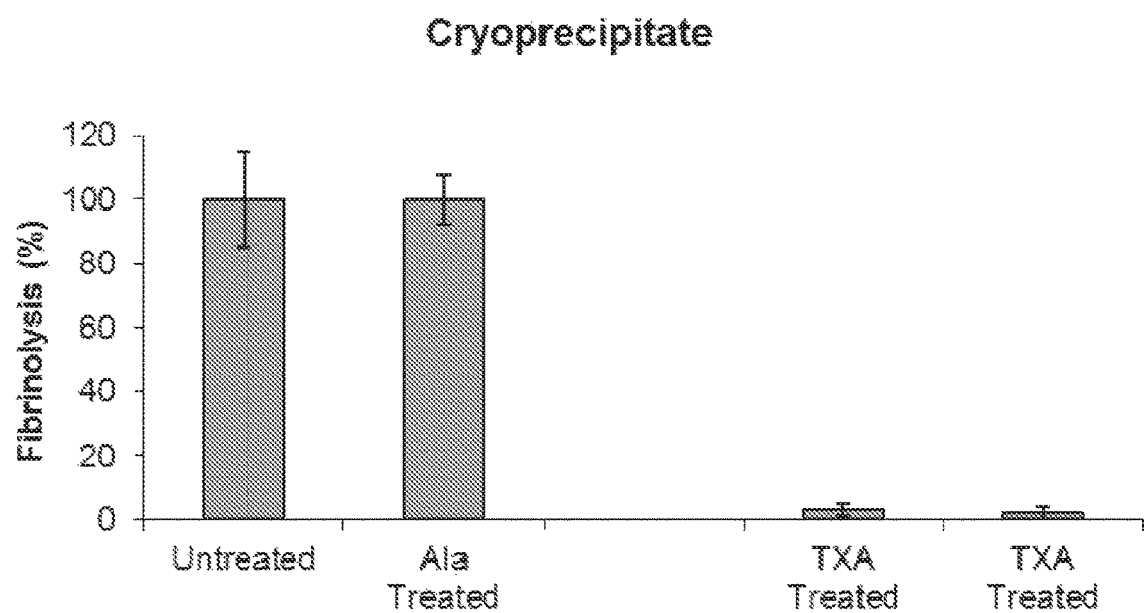

FIG. 3. Pretreating of human cryoprecipitate with magnetic beads coated with tranexamic acid (TXA) inhibits fibrinolysis t-PA-deficient and Plasminogen depleted cryoprecipitate prepared from FFP by incubation with tranexamic acid coated beads as detailed in FIG. 2 and Experimental procedures. Followed by clot formation and the addition of tPA, the lysis of plasma clots was measured and presented as a percent of fibrinolysis relative to that observed in untreated cryoprecipitate or cryoprecipitate treated with alanine coated beads (negative controls).

Figure 4:
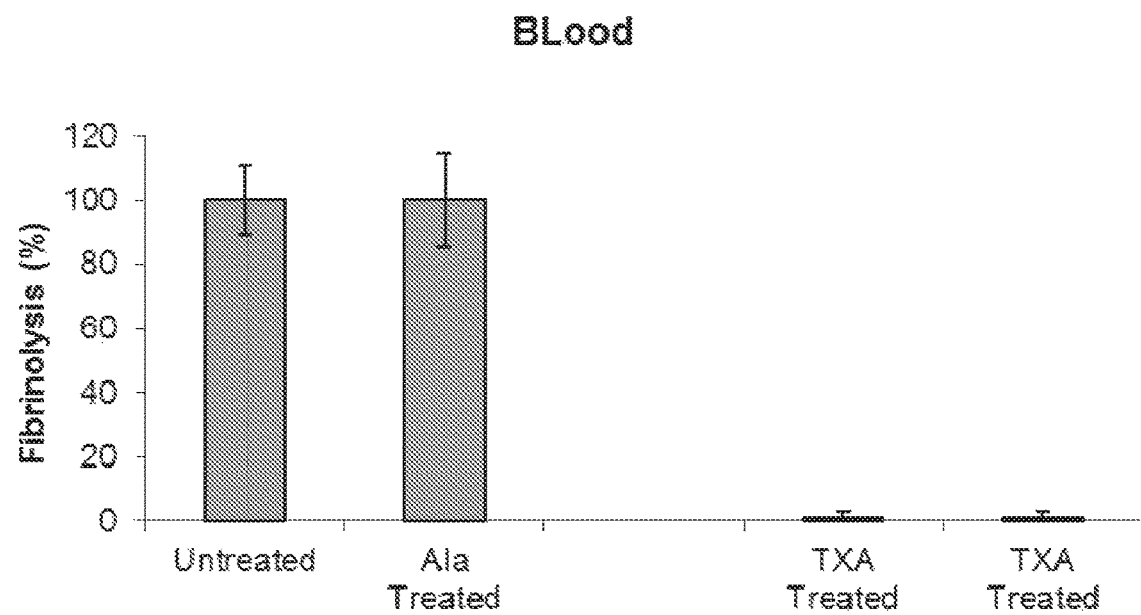

FIG. 4. Pretreating of human whole blood with magnetic beads coated with tranexamic acid (TXA) inhibits fibrinolysis Whole blood deficient in t-PA and plasminogen was prepared by incubation with tranexamic acid coated beads as detailed in Experimental procedures. Followed by clot formation and the addition of tPA, the lysis of plasma clots was measured and presented as a percent of fibrinolysis relative to that observed in untreated blood or the blood treated with alanine coated beads (negative controls).

Figure 5:
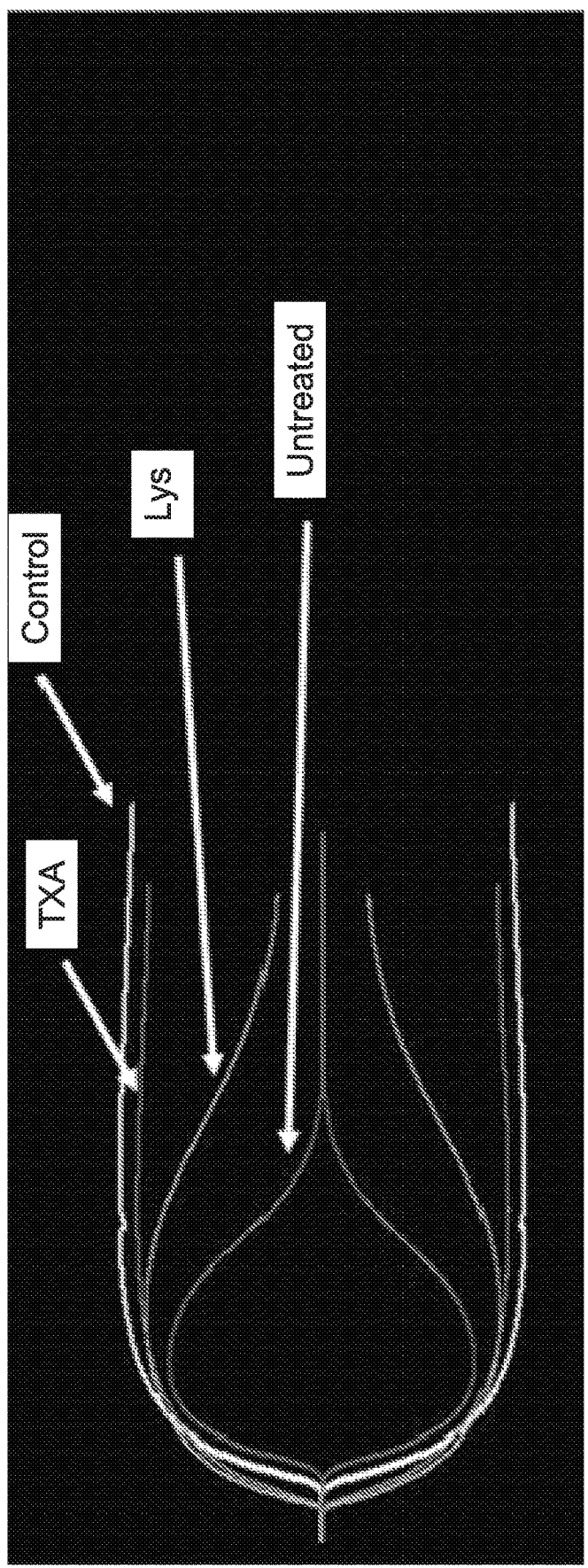

FIG. 5. Pretreating of human blood with magnetic beads coated with lysine or tranexamic acid inhibits clot lysis monitored by Thromboelastography (TEG)

Lysis of clots prepared from fresh whole human blood untreated ("Untreated") or pre-treated with magnetic beads coated with lysine (Lys) or its synthetic analog, tranexamic acid (TXA), was monitored by TEG. Clot lysis was induced by adding tPA (10 nM). "Control" relates to the clot formation and lysis of untreated human blood in the absence of tPA.

Figure 6A:
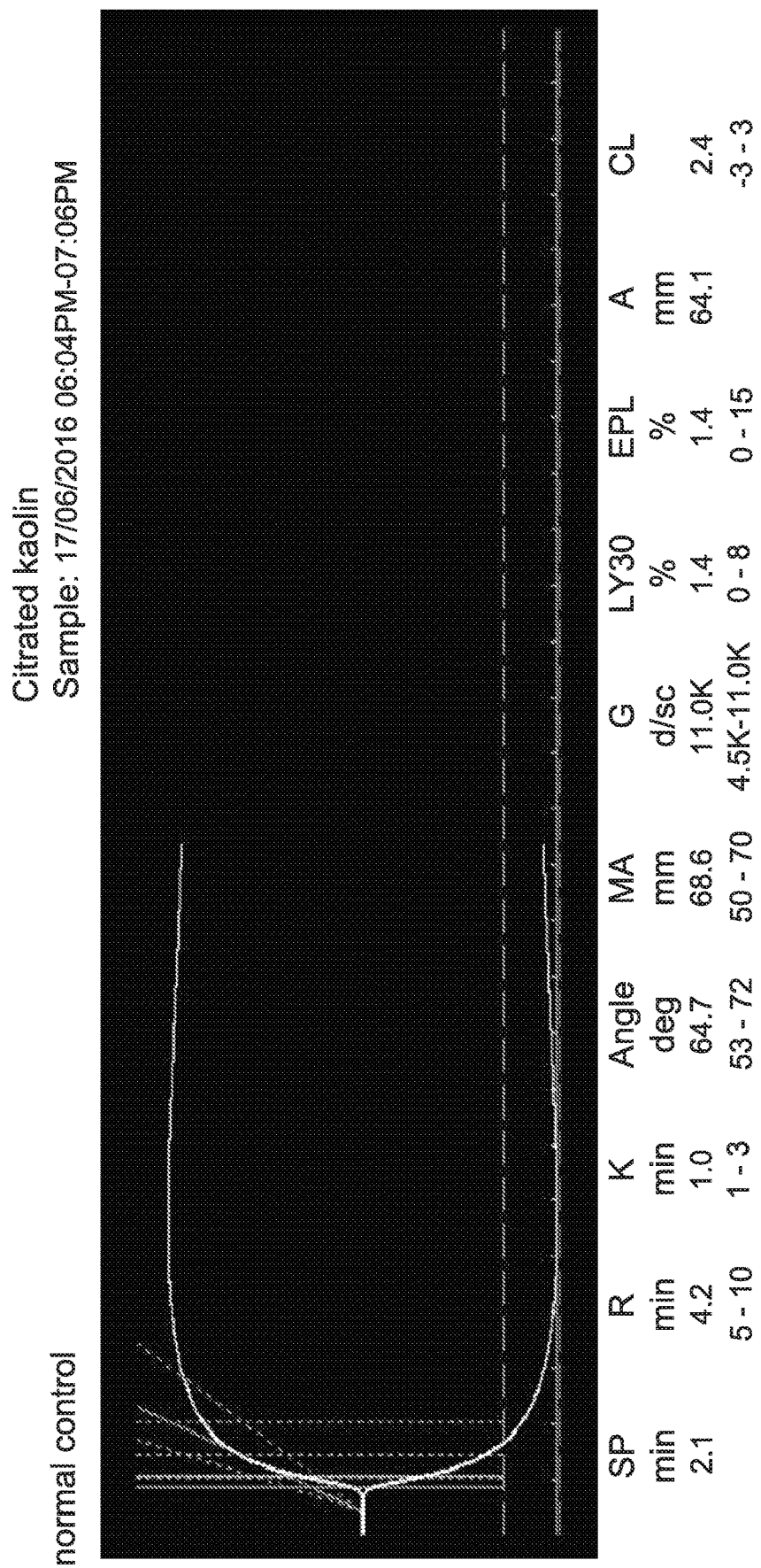
Figure 6B:
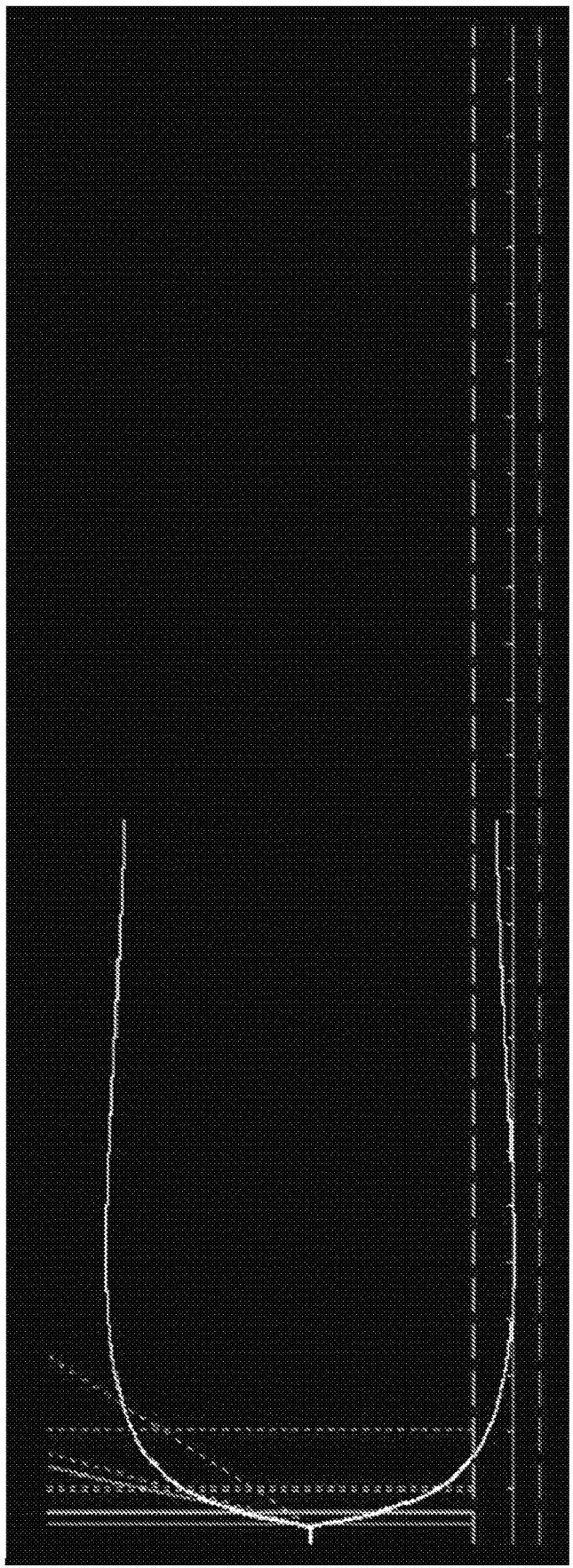
Figure 6C:
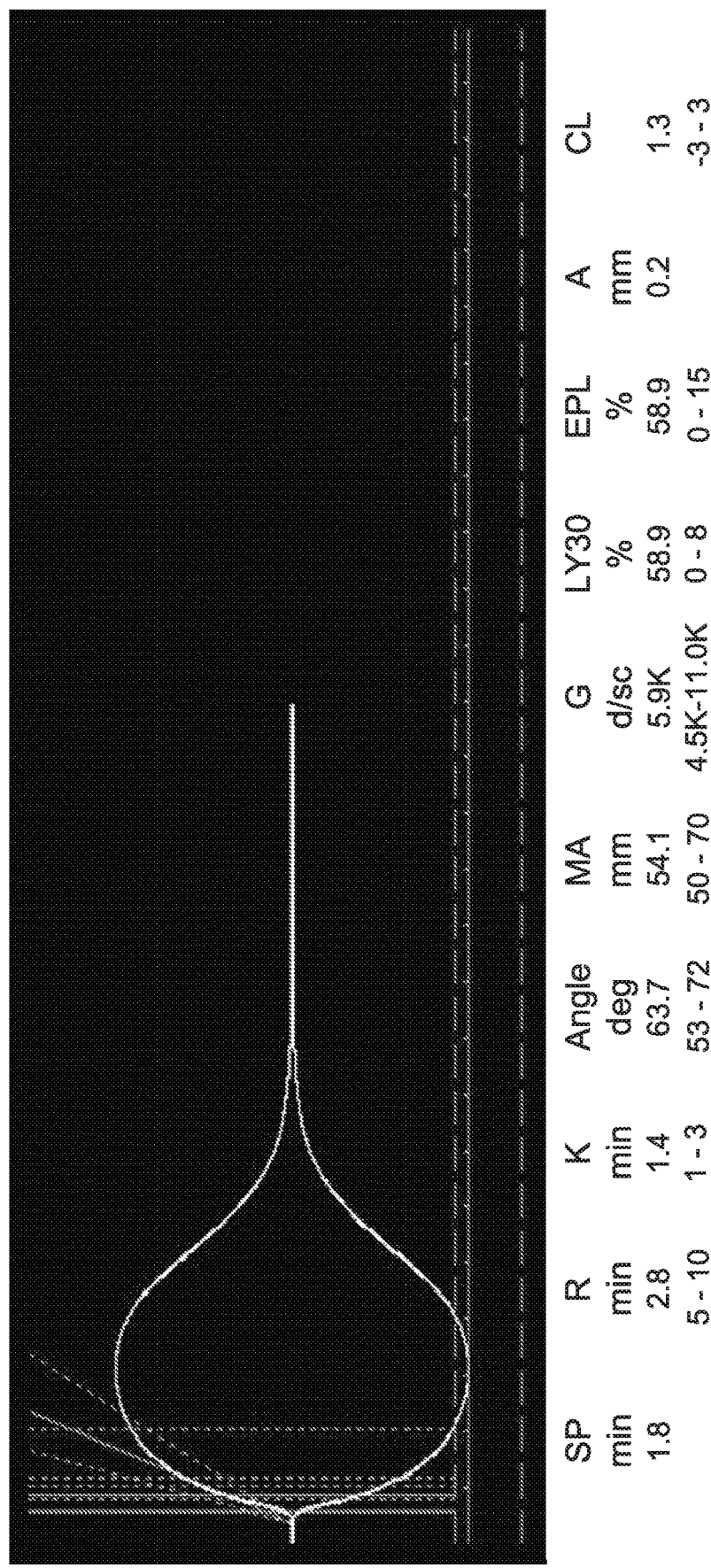

FIG. 6A-6C. Pretreating of human blood with magnetic beads coated with tranexamic acid enhances blood coagulation The extent of fibrinolysis of either pretreated or untreated plasma was monitored by TEG. The R value obtained by TEG represents the time until the first evidence of a clot is detected. FIG. 6A shows the R value of untreated blood, FIG. 6B shows the R value of the blood pretreated with magnetic beads coated with tranexamic acid and FIG. 6C shows the R value in the presence of tPA.

Figure 7A:
Figure 7B:
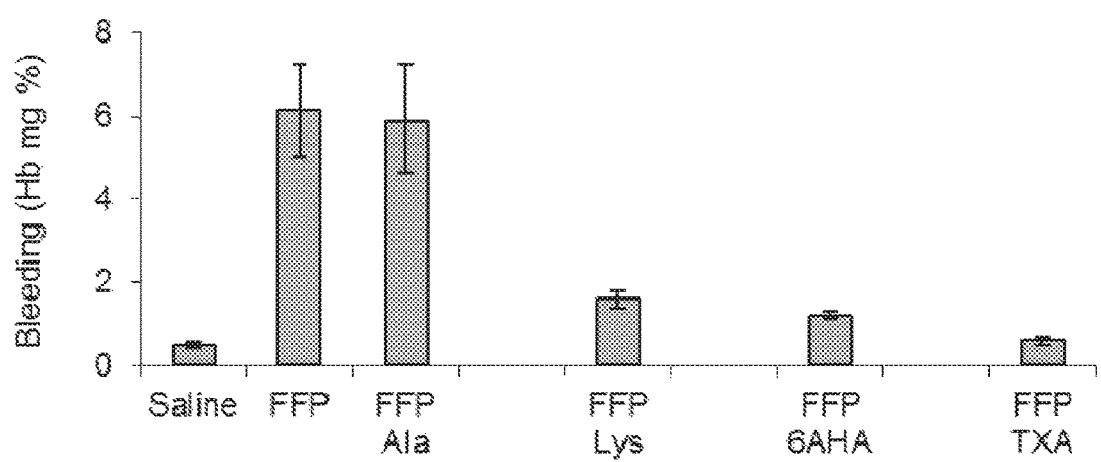

FIG. 7A-7B. Pretreating of human plasma with magnetic beads coated with lysine or lysine analogs inhibits bleeding tendency induced by tail tip amputation in mice After tail tip amputation, the tails were immersed in saline (Saline), human untreated FFP (FFP) or FFP treated with magnetic beads coated with lysine (FFP Lys), 6-Aminohexanoic-Acid (FFP 6AHA), tranexamic acid (FFP TXA) or alanine (FFP Ala) for 30 min. After 30 min the extend of bleeding was determined by measuring hemoglobin concentration in the saline solution and each one of the FFP products.

FIG. 8.

t-PA and Plasminogen-depleted Plasma injection reduces the amount of blood lost induced by tail tip amputation in mice.

Mice were intravenous injected with 50 μl (5% of total blood volume) of plasma Normal Plasma i.e. containing plasminogen or with Treated Plasma i.e. depleted plasminogen and t-PA or with PBS. Following, the mice tails were cut and blood from the tip of tails were collected for 30 min. The histogram represent the amount of hemoglobin form the different groups. (N=5) for each group.

FIG. 9.

Plasma treated with magnetic beads coated with lysine analogs (TXA) and the commercially available product EVICEL® are both plasminogen-deficient.

Fibrinolysis levels observed following addition of exogenous tPA to clots formed from plasma treated with magnetic beads coated with lysine analogs (TXA) or clots formed from a commercially available product.

FIG. 10.

Plasma treated with magnetic beads coated with lysine analogs (TXA) is also tPA deficient in contrast with EVICEL®

Fibrinolysis levels observed following addition of exogenous Plasminogen to clots formed from plasma treated with magnetic beads coated with lysine analogs (TXA) or clots formed from a commercially available product.

FIG. 11.

Comparison of tPA concentrations in plasma treated with magnetic beads coated with lysine analogs (TXA) and EVICEL® tPA concentrations measured by Elisa assay in untreated blood, plasma or serum, in EVICEL® and in plasma treated with magnetic beads coated with lysine analogs (TXA).

Figure 12:
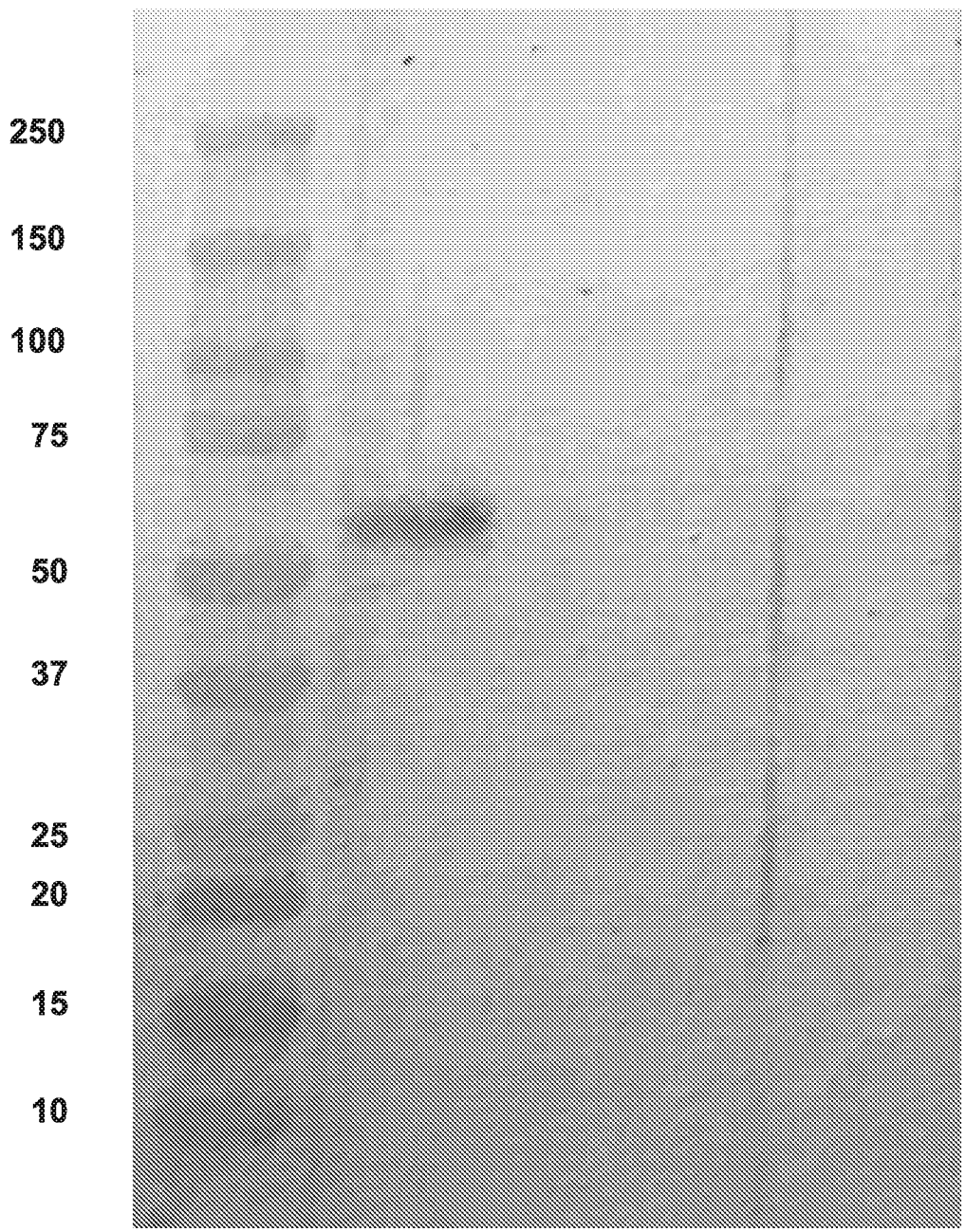

FIG. 12. The TXA-matrix of the invention binds tPA

Figure shows western blot analysis performed in proteins eluted from TXA-magnetic beads of the invention (lane 2), as compared to proteins eluted from TEA-sepharose 4B (Omrix, LANE 3). Blot was incubated with anti-tPA antibodies. Lane 1 shows molecular weight markers).

DETAILED DESCRIPTION OF THE INVENTION

A proposed physiological cell-based model of hemostasis is initiated when activated factor VII (VIIa) binds to tissue factor bearing cells leading to further activation of factors IX and X, which in turn cut (activates) factor II (prothrombin) to form thrombin (IIa). Thrombin activates factor XI that in turn activates other factors to generate more thrombin. Thrombin then further cleaves fibrinogen to form the preliminary fibrin clot, which is then stabilized into firm hemostatic clot by the cross-linked action of factor XIII In response to vascular injury, the coagulation system is activated as above leading to, cross-linked fibrin deposition in tissues and blood vessels, thus compromising the flow of blood. Therefore, a further system is required that can appropriately dissolve the fibrin clot, thereby preventing further growth of the clot beyond the physiological need, and initiate clot lysis when the clot is not needed any more. This system is composed of the fibrinolytic proteins, which are then activated, converting fibrin to its soluble degradation products through the action of the serine protease, plasmin. Under physiologic conditions, fibrinolysis is precisely regulated by the measured participation of activators, inhibitors and cofactors.

Plasminogen, the main component of the fibrinolytic system, is synthesized primarily in the liver. Cleavage (activation) of plasminogen at a single Arg-Val peptide bond at position 560-561, gives rise to the active serine protease, plasmin, which in turn dissolves fibrin clot. The cleavage of plasminogen is mediated by plasminogen activators.

The main endogenous plasminogen activator is tissue plasminogen activator (tPA). Functionally, t-PA is itself a poor activator of plasminogen. However, in the presence of fibrin, the catalytic efficiency of tPA-dependent plasminogen activation increases by 500-fold. Surpassed plasmin activity also cleaves the coagulation factors and by that would prevent the formation of new clots.

The second endogenous plasminogen activator is a single chain u-PA or prourokinase. u-PA has much lower affinity for fibrin than tPA. Although uPA is an effective plasminogen activator in the presence or the absence of fibrin, its plasminogen activation activity is significantly stimulated by fibrin. u-PA is expressed by several cells including activated endothelial cells, macrophages, renal epithelial cells, and some tumor cells.

The fibrinolytic system is quite balanced by the action of activators (as detailed above) and inhibitors of fibrinolytic proteins. The main inhibitor of plasmin is $\alpha_2$ antiplasmin—a single chain glycoprotein that is synthesized primarily in the liver and circulates in plasma at relatively high concentrations (2 µM). Plasmin released into flowing blood or in the vicinity of a clot is immediately neutralized upon forming an irreversible 1:1 stoichiometric complex with $\alpha_2$ antiplasmin.

Among the inhibitors of plasminogen activators, plasminogen activator inhibitor-1 (PAI-1) is the most ubiquitous. It is released by endothelial cells, monocytes, macrophages, hepatocytes, adipocytes, and platelets. PAI-1 is the most important and rapidly acting physiologic inhibitor of both tPA and u-PA.

Plasminogen activator inhibitor 2 (PAI 2) is synthesized by human placenta. Significant levels of PAI 2 are found in human plasma primarily during pregnancy.

Finally, thrombin-activatable fibrinolysis inhibitor (TAFI) is a plasma carboxypeptidase with specificity for carboxy-terminal arginine and lysine residues that acts as a potent inhibitor of fibrinolysis.

Treatment of patients with various coagulation abnormalities is essential during spontaneous bleeding episodes, trauma and throughout surgical procedures. In most such situations blood/plasma-derived products (for example regular plasma or fresh frozen plasma—FFP) are used. These products contain coagulation factors and fibrinolytic proteins, and therefore, supposed to stop bleeding and to correct the missing or impaired coagulation abnormality by inducing formation of a hemostatic clot. In general, a lack or abnormality of any coagulation factor may end up with bleeding tendency because of an insufficient ability to make a stable hemostatic clot. Without being bound by any theory, the inventors assumed that the presence of fibrinolytic proteins is responsible for lysis of the hemostatic clot may result in dissolution of the clot and aggravation of bleeding phenomena.

Thus, once a hemostatic clot has been formed following the replacement of missing coagulation factor by blood/plasma-derived product/s available, the clot dissolution, if required, is accomplished by the fibrinolytic system. However, if dissolution of the clot is not desired and quite an opposite activity is needed, for example, to keep the hemostatic clot in situations of bleeding or to generate more blood clots, then a treatment with blood/plasma-derived products that consist the coagulation factors but are depleted in fibrinolytic factors is a desirable solution.

This need for coagulation factors-containing but fibrinolytic factor-free products for the treatment or prevention of bleeding in congenital or acquired bleeding tendencies including coagulopathies, has been hypothesized for the first time by the inventors and stimulated them to develop blood and blood-derived product that may be tPA-deficient and/or devoid of plasminogen or plasmin activity, specifically, t-PA-deficient and/or plasminogen-deficient products, in particular t-PA-deficient and/or plasminogen-deficient blood, t-PA-deficient and/or plasminogen deficient fresh plasma, t-PA-deficient and/or plasminogen-deficient-FFP and t-PA-deficient and/or plasminogen-deficient cryoprecipitate to fulfill a long-felt need for hemostatic fibrinolytic protein-free products.

Specifically, the inventors hypothesize that the clot formation by the transfused coagulation factors also activates the fibrinolytic system, and accelerates lysis of newly formed clots. Based on this, the current invention discloses that extracting t-PA and depleting or deactivating plasminogen from blood and plasma products prevents untoward fibrinolysis and enhances the efficacy of the products, as well as minimizes the amount given to a patient.

Thus, a blood and blood-derived product that may be tPA-deficient and/or devoid of plasminogen or plasmin activity, specifically, a t-PA-deficient and/or plasminogen-deficient blood, and plasma product, that lack fibrinolytic activity are generated and in addition, these products are enriched in the endogenous plasmin inhibitor, $\alpha_2$-anti-plasmin. These products will be suitable for treatment of active bleeding or for prevention of anticipated bleeding in patients with coagulopathies.

The use of t-PA-deficient and plasminogen-free blood or plasma products decrease the activity of the endogenous fibrinolytic system, improve hemostasis in a bleeding patient, while the presence of $\alpha_2$-antiplasmin in the products and increase further the endogenous anti-fibrinolytic activity needed to stop or prevent the resolution of any hemostatic clots and by that prevent any life threatening bleeding.

Figure 8:
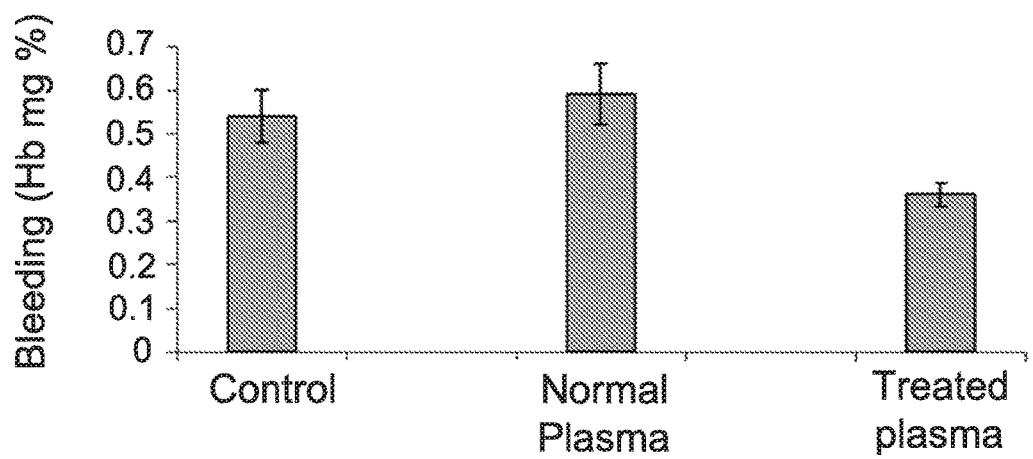
Figure 10:
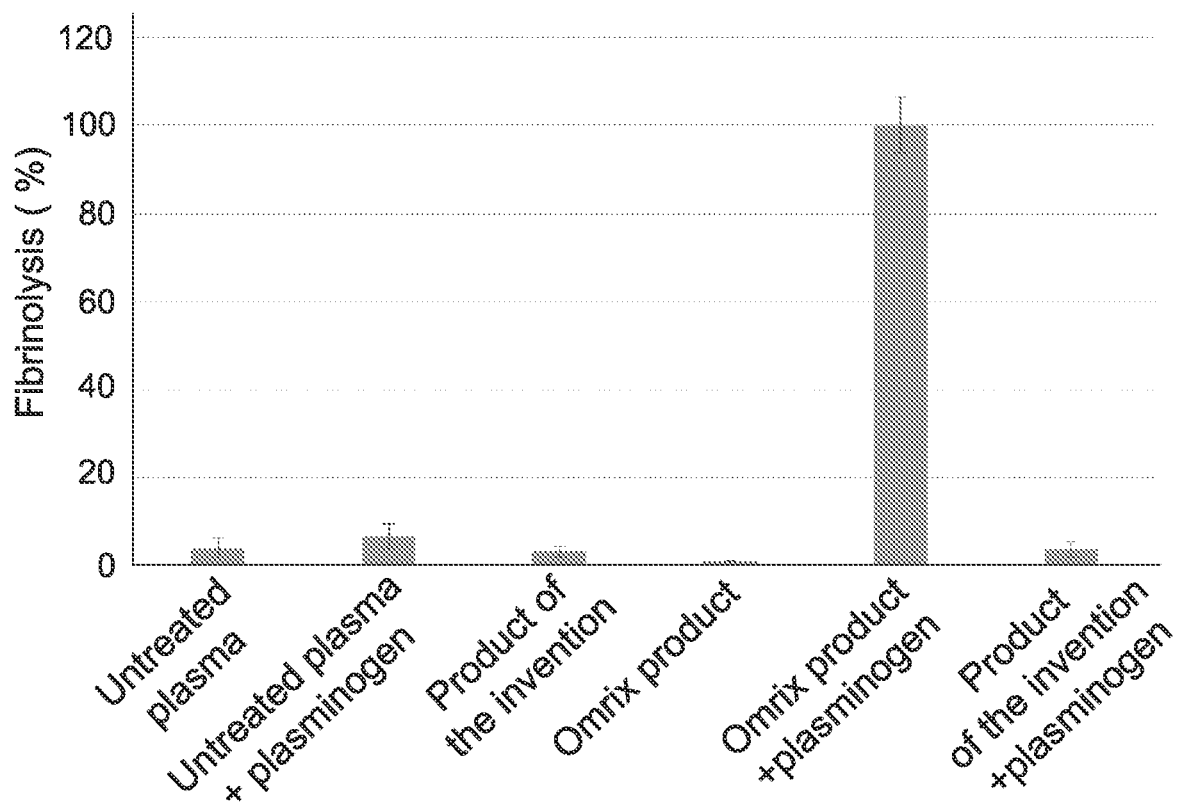
Figure 11:
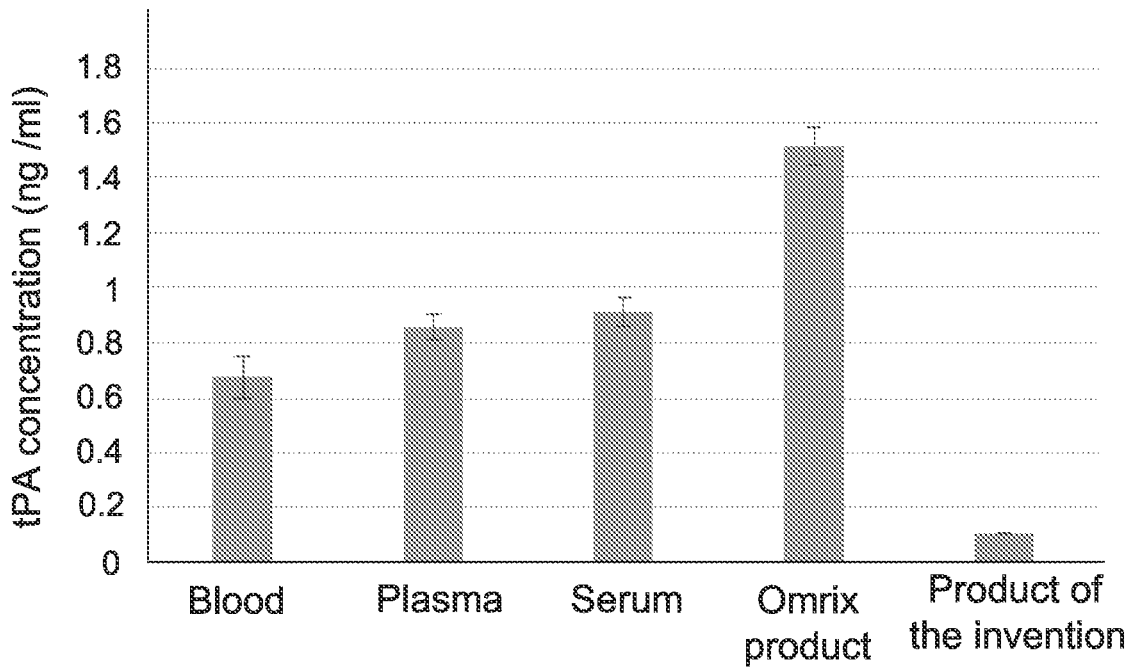

The new therapeutic strategies undertaken by the inventors may lead to the development of new products, which exhibit pro-coagulant and antifibrinolytic properties at the same time (as shown in Examples). These products of the invention are highly valuable and may substantiate new therapeutic strategy in situations associated with bleeding in which a formation of a clot resistant to fibrinolysis is desirable. As shown by the Examples, application of lysine or lysine analogs coated beads to the blood and blood derived products aiming to deplete t-PA and plasminogen, resulted in inhibition of fibrinolysis by these products as determined by clot lysis assay (FIGS. 2-3) or by thromboelastography (FIGS. 5-6). Specifically, the inhibition of fibrinolysis was observed with t-PA-deficient and plasminogen-depleted plasma (FIG. 2), t-PA and plasminogen-depleted cryoprecipitate (FIG. 3) and t-PA and plasminogen depleted whole blood (FIG. 4). In addition, depletion of t-PA and plasminogen from whole blood resulted in a combined pro-coagulant quality of the product: an increased coagulation on one hand and a decreased fibrinolysis on the other hand, as demonstrated by TEG (FIGS. 5-6). Moreover, the product of the invention (t-PA and plasminogen-depleted plasma) significantly reduced the amount of bleeding in the murine tail-tip model (FIGS. 7-8). Finally, the product of the invention was compared to a commercially available plasminogen-deficient product i.e. EVICEL® and provides significant therapeutic advantages. The product of the invention was clearly shown as displaying increased stability of the clots even upon addition of plasminogen in the presence of thrombin (FIG. 10). This enhanced stability is attributed to the depletion of tPA from the blood product of the invention as shown in FIG. 11. As shown by FIG. 12, the commercial plasminogen removable gels used for the preparation of the EVICEL® product, could not bind tPA and thereby lack the ability of depleting tPA from blood or blood products. The resulting mixtures (EVICEL® product) still contain tPA and as such, can activate any plasminogen present in the treated area thereby exhibiting fibrinolytic activity. Thus, the plasminogen-free products disclosed in U.S. Pat. No. 7,125,569 may be used only for topical applications as a biological glue, and are irrelevant for systemic use in transfusion or for treating bleeding associated with fibrinolytic or thrombolytic therapy.

Further comparative in vivo assay presented in Example 6, performed using a rat model for internal bleeding, revealed the clear advantage of the product/s of the invention over the commercial EVICEL® product, in significantly reducing the bleeding time, even in topical applications.

Thus, the first aspect of the present invention relates to a blood and blood-derived product that may be tPA-deficient and/or devoid of plasminogen or plasmin activity. It should be noted that the products of the invention comprise at least one coagulation factor and has decreased fibrinolytic activity.

As indicated herein, in some embodiments, the product of the invention is devoid of plasminogen and/or plasmin activity. Plasminogen, when activated to form the active plasmin enzyme, display proteolytic activity, specifically, cleavage or breakdown of proteins into smaller polypeptides or amino acids. In this connection, the product of the invention is devoid of plasminogen or plasmin proteolytic activity. In some specific embodiments, the proteolytic activity of plasmin and plasminogen involves the cleavage of fibrin, thereby dissolving fibrin clots. It should be appreciated that the term "devoid of plasmin and plasminogen activity" is meant that the product of the invention lacks or displays "reduced", "decreased" "moderated", "inhibited" or "attenuation" proteolytic activity of plasmin and plasminogen by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9% or 100%, as compared to the proteolytic activity of active plasmin or plasminogen in a blood or blood product, specifically, untreated blood or blood product.

In some specific embodiments, the product of the invention may be a t-PA-deficient blood or blood-derived product. In some other specific embodiments, the product of the invention may be devoid of plasminogen and/or plasmin activity. In yet some specific embodiments, the product of the invention may be a t-PA-deficient and devoid of plasminogen and/or plasmin activity. In yet some further embodiments, the product of the invention may be a t-PA-deficient blood or blood-derived product. In some other specific embodiments, the product of the invention may be a plasminogen-deficient blood or blood-derived product. In yet some specific embodiments, the products provided by the invention may be t-PA-deficient and plasminogen-deficient blood and blood-derived product/s that comprise at least one coagulation factor and display decreased fibrinolytic activity.

As noted above, the product of the invention may be a tPA-deficient product. It should be appreciated that the term tPA used herein for the tissue plasminogen activator (also known as PLAT; enzyme entry EC 3.4.21.68,) relates to a secreted serine protease that converts and activates the proenzyme plasminogen to a potent fibrinolytic enzyme plasmin. tPA is synthesized in vascular endothelial cells as a single polypeptide chain that undergoes proteolytic cleavage by plasmin or trypsin at a centrally located arginine-isoleucine bond, resulting in a 2-chain disulfide-linked form composed of the N-terminally derived heavy chain and the C-terminal light chain. The tPA gene (DNA acc. NT 167187.1 mapped to chr. 8p11.21) contains 14 exons encoding the heavy chain domain including two kringle regions (K1 and K2) and regions homologous to growth factors and the light chain domain comprising the serine protease catalytic site. Alternative splicing of the tPA gene results in multiple transcript variants encoding different isoforms taking part in multiple biological processes, apart from fibrinolysis, such as cell migration and tissue remodeling. Increased tPA activity causes hyperfibrinolysis manifested as excessive bleeding; decreased tPA activity leads to hypofibrinolysis which can result in thrombosis or embolism. tPA linked phenotypes include familial hyperfibrinolysis (due to increased tPA release) and familial thrombophilia (due to decreased tPA release (OMIM num. 612348).

A "tPA-deficient product" or "tPA-free product" as used herein is meant that the products of the invention (that according to some embodiments, have been prepared by treating blood or blood products with a tPA- and/or plasminogen-binding agents), display a reduced, decreased, attenuated, amount of tPA normally present in about 100% to 50%, as compared to untreated blood or blood product. More specifically, at least about 50%, 55%, 60%, 65%, 70%, 75%, 80%, 85%, 90%, 95%, 96%, 97%, 98%, 99% or 100%, of tPA is removed from the products of the invention, specifically when compared to untreated blood or blood products, or in some embodiments, as compared to the commercially available EVICEL® product (see FIG. 11). In other words, the product of the invention may comprise tPA in an amount of about 0.01% to about 50% of the amount of tPA in other products or in untreated blood or blood products. Specifically, about 0.01% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50% or less, even 60% or 70% of the amount of tPA as compared to untreated blood or blood products.

In yet some further embodiments, the product of the invention may be also plasminogen-deficient. Plasminogen, (also known as PLG, Enzyme entry EC:3.4.21.7), as used herein, is the main component of the fibrinolytic system and is synthesized primarily in the liver. Two major glycoforms of plasminogen are present in humans—type I plasminogen that contains two glycosylation moieties (N-linked to N289 and O-linked to T346), whereas type II plasminogen contains only a single O-linked sugar (O-linked to T346). Type II plasminogen is preferentially recruited to the cell surface over the type I glycoform. Conversely, type I plasminogen appears more readily recruited to blood clots. In circulation, plasminogen adopts a closed, activation resistant conformation. Upon binding to clots, or to the cell surface, plasminogen adopts an open form that can be converted into active plasmin by a variety of enzymes, including tissue plasminogen activator (tPA), urokinase plasminogen activator (uPA), kallikrein, and factor XII (Hageman factor). More specifically, the cleavage (activation) of plasminogen at a single Arg-Val peptide bond at position 560-561, gives rise to the active serine protease, plasmin, which in turn dissolves fibrin clot.

Full length plasminogen comprises seven domains. In addition to a C-terminal chymotrypsin-like serine protease domain, plasminogen contains an N-terminal Pan Apple domain (PAp) together with five Kringle domains (KR1-5). The Pan-Apple domain contains important determinants for maintaining plasminogen in the closed form, and the kringle domains are responsible for binding to lysine residues present in receptors and substrates.

In some embodiments, the plasminogen referred to by the invention may be the human plasminogen. In such embodiments, the plasminogen gene (GenBank: AY192161.1 mapped to chr6q26) spans about 52.5 kb of DNA and contains 19 exons (OMIM num173350).

A "plasminogen-deficient product" or "plasminogen-free product" as used herein is meant that the products of the invention (that according to some embodiments, have been prepared by treating blood or blood products with tPA- and/or plasminogen-binding agents), display a reduced, decreased, attenuated, amount of plasminogen in about 100% to 50%, as compared to untreated blood or blood product. More specifically, at least about 50%, 55%, 60%, 65%, 70%, 75%, 80%, 85%, 90%, 95%, 96%, 97%, 98%, 99% or 100%, of plasminogen normally present in blood or blood products is removed from the products of the invention, specifically when compared to untreated blood or blood products. In other words, the product of the invention may comprise plasminogen in an amount of about 0.01% to about 50% of the amount of the plasminogen in other products or untreated blood or blood products. Specifically, about 0.01% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 60%, 70% or less of the amount of plasminogen as compared to untreated blood or blood products.

As noted above, due to lack of tPA and plasminogen, the product of the invention displays reduced fibrinolytic activity. Fibrinolytic activity, as used herein refers to the ability of some proteolytic enzymes in the blood and blood-derived products to dissolve the fibrin and blood clots. The major proteolytic enzyme cleaving fibrin is plasmin. When plasmin breaks down fibrin, fibrin degradation products (FDPs) are formed. FDPs compete with thrombin, and thus slow down clot formation by preventing the conversion of fibrinogen to fibrin.

As indicated above, the blood products of the invention display reduced, or decreased fibrinolytic activity. It should be appreciated that the terms "reduced", "decreased" "moderated", "inhibited" or "attenuation" as referred to herein, relate to the retardation, restraining, decrease or reduction of a process, specifically, fibrinolytic activity, by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%, or even 100% as compared to blood or blood products that comprise tPA and or plasminogen, to blood or blood products that were not treated with the tPA and/or plasminogen binding compounds (e.g., TXA), to normal blood or blood products or to commercially available blood products. In other words, these products display no fibrinolytic activity, or at the most, neglectabal and reduced fibrinolytic activity, specifically, about 0.01% or less, 0.05%, 0.1%, 0.5%, 1%, 2%, 3%, 4%, 5%, 6%, 7%, 8%, 9%, 10%, 15%, 20%, 25%, 30%, 35%, 40%, 45%, 50% or less of the fibrinolytic activity as compared to the fibrinolytic activity of an untreated blood or blood product.

In some specific embodiments, the t-PA-deficient and plasminogen-deficient blood and blood-derived product with reduced fibrinolytic activity of the invention is at least one of whole blood, plasma, fresh frozen plasma (FFP), platelet rich plasma (PRP) and cryoprecipitate.

Blood transfusion is still the most essential factor in saving a life. In modern blood banking therapy blood components rather than whole blood is transfused.

Blood-component therapy refers to separation of blood into components to allow transfusion of only specific desired component to the patient, thus, avoiding the use of unnecessary component. By using blood components several patients can be treated with the blood from one donor.

The term "Fresh frozen plasma" (FFP) as used herein relates to the main blood component, that is the acellular liquid fraction of human blood that has been frozen and preserved after a blood donation and will be used for transfusion. Following donation, one unit of human blood is centrifuged, the cell content of the blood is separated, and the remained plasma is frozen at −18 C (0 F) or colder within eight hours of collection.

FFP contains all components (factors/proteins) of the coagulation, fibrinolytic and complement systems. Well-defined indications exist for the use of FFP in single or multiple coagulation deficiencies, as well as in existing or anticipated hemorrhage as occur in trauma or surgery.

"Cryoprecipitate" as used herein, relates to precipitated proteins of plasma obtained from a single unit of fresh plasma by rapid freezing within 6-8 hrs of collection (as done for FFP) and rapid thawing at 4° C. Cryoprecipitate is rich in Factor VIII, factor XIII, von Willebrand factor and fibrinogen. Thus, this component is suitable for treatment or prevention of bleeding in hereditary or acquired conditions associated with lack or impairment of the above mentioned coagulation proteins. The data of the inventors as shown in Example 2, indicate that the conventional cryoprecipitate contains plasminogen that can be activated by plasminogen activators and thereby contribute to clot lysis exerting deleterious effect in the recipient. The cryoprecipitate of the invention that lacks tPA and plasminogen has decrease fibrinolytic activity and therefore may be particularly suitable for treating hereditary or acquired conditions associated with lack or impairment of the above mentioned coagulation proteins.

"Platelet rich plasma" (PRP) blood component is prepared from one unit of fresh (donated) blood by centrifugation or aphaeresis procedure.

Beside to being prepared from a standard unit of whole blood, blood components can be obtained by aphaeresis procedure. Aphaeresis is done using a pheresis apparatus/machine, which is a semi-automated blood-separator instrument. In this procedure if plasma is planned to be used for a donation, the donor's anticoagulated whole blood is passed through an apparatus in which the blood is separated into red cells, plasma, and a leukocyte/platelet fractions, which are then returned to the subject. Only the separated plasma is not returned to the subject but is further used for donation.

Several semi-automated blood-cell-separator instruments are available for collection of platelets, granulocytes, blood stem cells, mononuclear cells, and plasma. All of these instruments use centrifugation to separate the blood components. Some apheresis procedures involve two venipunctures with continuous flow of blood from the donor through the blood cell separator; others can be accomplished with a single venipuncture and intermittent blood withdrawal and return.

In certain specific embodiments, the invention provides blood and blood-derived product that may comprise fibrinogen. In more specific embodiments, the product/s of the invention may be further supplemented with exogenous fibrinogen.

Fibrinogen (coagulation factor I) is the last protein of the coagulation cascade. It is cleaved by thrombin (factor IIa) to yield a primary unstable fibrin clot, which is further stabilized into firm and stable clot. Fibrinogen is a constant constituent of every blood derived product, and therefore in situations where a replacement therapy with fibrinogen is required these blood derived products are administered to provide fibrinogen. More specifically, Fibrinogen (factor I), as used herein, is a soluble plasma glycoprotein with a molecular weight of approximately 340 kDa and circulates in plasma as a precursor of fibrin. The native molecule is a homo-dimer, in which both subunits consist of three different polypeptide chains (Aα, Bβ, and γ). All three polypeptide chains of the subunits as well as the dimer are linked with disulfide bonds. The three pairs of polypeptide chains named Aα, Bβ, and γ are composed of 610, 461, and 411 amino acids, respectively. Fibrinogen is synthesized in the liver by the hepatocytes. The concentration of fibrinogen in the blood plasma is 200-400 mg/dL (normally measured using the Clauss method).

Variety of Fibrinogen concentrates and products are currently commercially available, to name but a few, Haemocomplettan (CSL Behring, Marburg, Germany), FIBRINOGENE T1 and Clottagen (LFB, Les Ulis, France), Fibrinogen HT (Benesis, Osaka, Japan) and FibroRAAS (Shangai RAAS, Shangai, China). However, the most widely used is Haemocomplettan (commercialized in the USA as RiaSTAP), a human pasteurised, highly purified, plasma-derived fibrinogen concentrate. It should be appreciated that any fibrinogen preparation, for example, any of the preparations disclosed above, may be added to the tPA and/or plasminogen free products of the invention.

It should be further appreciated that the t-PA-deficient and/or plasminogen-deficient blood or blood-derived product of the invention, may also serve as a suitable source for fibrinogen and may therefore be suitable for use in situation where the replacement with fibrinogen is required.

In yet certain embodiments, the product of the invention may further comprises at least one inhibitor of at least one of plasmin, plasminogen and plasminogen activator or any combination thereof.

In the present disclosure the inventors employed a novel approach for inhibiting fibrinolytic activity of blood and blood-derived products supplemented or not with exogenous fibrinogen, which is based on the depletion of main fibrinolytic proteins, specifically, tPA and plasminogen.

Moreover, the fibrinolytic activity of the product of the invention can be further inhibited by adding to the t-PA-deficient and plasminogen-depleted blood and blood derived product additional inhibitor of fibrinolysis, such as at least one of inhibitor/s of plasmin, inhibitor/s of plasminogen and inhibitor/s of plasminogen activator.

Thus, according to specific embodiments, the product of the invention may be particularly suitable for parenteral use. When used parenterally, at least one of inhibitors of fibrinolysis, TLCK hydrochloride (TLCK), Camostat mesylate, Benzamidine HCl, α2-anti-plasmin, tPA-mutant, PAI-1, aprotonin, PPACK dihydrochloride, biotinylated (tTA inhibitor), TAFI (thrombin-activatable fibrinolysis inhibitor) and lysine analogs like tranexamic acid may be added to the product.

More specifically, TLCK hydrochloride (TLCK), (CAS 4238-41-9), as used herein, is an active site-directed agent that irreversibly inhibits trypsin-like serine proteases such as granzyme D and tryptase. Cysteine proteases and other enzymes may be inhibited by TLCK through non-selectively interactions with thiol groups. To prevent proteolytic degradation, TLCK may be employed in protein purification protocols. TLCK has been shown to selectively inactivate clostripain obtained from C. histolyticum. Also, TLCK has been observed to inhibit other proteases including trypsin, plasminogen (plasmin), thrombin, papain and some kinases including PKC.

Camostat (INN) or FOY-305, (CAS 59721-28-7) is a trypsin-like protease inhibitor known to inhibit trypsin and various inflammatory proteases including plasmin, kallikrein, and thrombin.

Benzamidine (CAS 618-39-3) is a reversible competitive inhibitor of trypsin, trypsin-like enzymes and serine proteases.

PPACK, Dihydrochloride, CAS 142036-63-3, is a highly potent, selective & irreversible inhibitor of thrombin. It can also inhibit tPA, Factors VIIa & XIa.

Thrombin activatable fibrinolysis inhibitor (TAFI) also known as Carboxypeptidase B2 (CPB2), carboxypeptidase U (CPU), plasma carboxypeptidase B (pCPB) is an enzyme that, in humans, is encoded by the gene CPB2. TAFI is synthesized by the liver and circulates in the plasma as a plasminogen-bound zymogen. When it is activated by proteolysis at residue Arg92 by the thrombin/thrombomodulin complex, TAFI exhibits carboxypeptidase activity. Activated TAFI reduces fibrinolysis by removing the fibrin C-terminal residues that are important for the binding and activation of plasminogen.

As noted above, the main advantage of the products of the invention is their applicability for transfusion and systemic use. Thus, in further embodiments the products of the invention may be suitable for systemic administration. The products of the invention can be administered and dosed by the methods of the invention, in accordance with good medical practice.

The phrases "systemic administration", "administered systemically" as used herein mean the administration of a product directly intravenously into the central blood system, such that it enters the patient's system and, thus, is subject to metabolism and other like processes. The phrases "parenteral administration" and "administered parenterally" as used herein means modes of administration other than enteral and topical administration, usually by injection, and includes, intravenous injection or intra-arterial.

In some further embodiments, the blood product of the invention may be derived from autologous human source (e.g. human blood, plasma or any other blood products).

In yet some other embodiments, the blood product of the invention may be derived from allogeneic human source (e.g. human blood, plasma or any other blood products).

"Autologous" blood donation as used herein is a concept where transfusion individuals can donate blood for their own use if the need for blood can be anticipated and a donation plan developed. Most commonly this situation occurs with elective surgery. Autologous blood for transfusion can be obtained by preoperative donation. In some specific embodiments, the blood or blood product of the invention may be originated from the human subject that will be treated with the same product.

The term "allogeneic blood" as used herein relates to blood collected from an unrelated donor of the same species. More specifically, in some embodiments, where the blood or blood products of the invention is obtained from at least one human subject or more, allogeneic source is meant that the resulting product may be used for other human individual/s.

In some embodiments, the autologous or allogeneic blood or blood product of the invention may be collected and maintained in sterile containers. In some embodiments, the containers may be made of plasticized material that is biocompatible with blood cells and allows diffusion of gases so as to provide optimal cell preservation. These blood containers are combinations of bags and integral tubing that allow separation of the whole blood into its components in a closed system, thus minimizing the chance of bacterial contamination while making storage of the components for days or weeks possible. It should be however appreciated that any suitable container may be used for the product/s of the invention.

Still further, due to the lack of tPA and/or plasmin and the resulting reduced fibrinolytic activity, in some embodiments, the product of the invention may further exhibit increased and extended shelf-life in appropriate preserving conditions.

According to a second aspect, the invention provides a composition comprising an effective amount of at least one blood and blood-derived product that may be tPA-deficient and/or devoid of plasminogen or plasmin activity. It should be noted that such product may comprise at least one coagulation factor and has reduced fibrinolytic activity. In some further embodiments, the product of the invention may be a t-PA-deficient blood or blood-derived product. In some other specific embodiments, the product of the invention may be devoid of plasminogen and/or plasmin activity. In yet some specific embodiments, the product of the invention may be a t-PA-deficient and devoid of plasminogen and/or plasmin activity. In yet some further embodiments, the product used by the composition of the invention may be a t-PA-deficient blood or blood-derived product. In some other specific embodiments, the product used by the composition of the invention may be a plasminogen-deficient blood or blood-derived product. In more specific embodiments, the product used for the composition of the invention may by a t-PA-deficient and plasminogen-deficient blood or blood-derived product.

In some embodiments, the composition of the invention may comprise the t-PA-deficient and plasminogen-deficient blood-derived product according to the invention, with no further pharmaceutically acceptable carrier/s, excipient/s, additive/s diluent/s and adjuvant/s. In yet some further alternative embodiments, the composition of the invention may be co-administered with at least one of pharmaceutically acceptable carrier/s, excipient/s, additive/s diluent/s and adjuvant/s.

In yet some further optional embodiments the composition of the invention may optionally further comprises at least one of pharmaceutically acceptable carrier/s, excipient/s, additive/s diluent/s and adjuvant/s.

In specific embodiments the product of the invention comprises at least one of t-PA-deficient and plasminogen-deficient whole blood, t-PA-deficient and plasminogen-deficient plasma (or plasminogen-deficient FFP), t-PA-deficient and plasminogen-deficient cryoprecipitate and t-PA-deficient and plasminogen-deficient PRP.

In some embodiments, the composition of the invention may comprise any of the products of the invention as defined in any of the embodiments disclosed herein before. In yet some further embodiments, the composition of the invention may be further supplemented with an effective amount of fibrinogen, and/or any other coagulation factor/s.

In some further embodiments the composition of the invention may be adapted for parenteral use. In yet another embodiment, the composition of the invention may be applicable for topical use.

Still further, it should be appreciated that in certain embodiments, the products of the invention may be further applicable as a pharmaceutical composition. More specifically, the composition of the invention may comprise as an active ingredient at least one of the products of the invention as described above, or any combinations thereof, and at least one pharmaceutically acceptable carrier/s, diluent/s, excipient/s.

"Pharmaceutically or therapeutically acceptable carrier" refers to a carrier medium which does not interfere with the effectiveness of the biological activity of the active ingredients and which is not toxic to the host or patient. As mentioned herein, the compositions provided by the invention optionally further comprise at least one pharmaceutically acceptable excipient or carrier. As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In yet another aspect, the invention relates to the biological glue or sealant comprising a blood and blood-derived product that may be tPA-deficient and/or devoid of plasminogen or plasmin activity. In yet some further embodiments, the product used by the glue of the invention may be a t-PA-deficient blood or blood-derived product. In some other specific embodiments, the product used by the glue of the invention may be devoid of plasminogen and/or plasmin activity. In yet some specific embodiments, the product of the invention may be a t-PA-deficient and devoid of plasminogen and/or plasmin activity. In more specific embodiments, the product used in the biological glue of the invention may be a t-PA-deficient and/or plasminogen-deficient blood-derived product. In yet some further specific embodiments, the glue of the invention may comprise at least one of t-PA-deficient and/or plasminogen-deficient FP, t-PA-deficient and/or plasminogen-deficient PRP, t-PA-deficient and/or plasminogen-deficient FFP, and t-PA-deficient and/or plasminogen-deficient cryoprecipitate.

The term "biological glue" as used herein refers to any biological glue which can provide adhesion between a living biological tissue and a synthetic or biological material (e.g. a patch); thus, providing an attachment between said tissue and said synthetic or biological material.

In some embodiments the biological glue/sealant of the invention may be produced from at least one of t-PA-deficient and/or plasminogen-deficient PRP, t-PA-deficient and plasminogen-deficient FFP and t-PA-deficient and plasminogen-deficient cryoprecipitate. Consequently, biological glue/sealant of the invention displays decreased fibrinolytic activity as it is deficient in the main fibrinolytic proteins, t-PA-deficient and plasminogen.

In further embodiments, biological glue/sealant may be produced from autologous plasma, FFP, cryoprecipitate and PRP. In yet another embodiment's biological glue/sealant is produced from allogeneic FP, FFP, cryoprecipitate and PRP.

The t-PA-deficient and plasminogen-deficient biological glue/sealant product of the invention will make the generated clot resistant to lysis induced by plasminogen activators present in the adjacent tissues. In addition, t-PA-deficient and plasminogen-deficient biological glue/sealant product can target its endogenous $\alpha_2$-antiplasmin inhibitor towards the fibrinolytic components of the neighboring tissues of the host, thereby further preventing the degradation of the clot by surrounding tissues.

Thus, according to some specific embodiments, t-PA-deficient and/or plasminogen-deficient, specifically, t-PA-deficient and plasminogen-deficient products/compositions as described by the invention (FP, FFP, cryoprecipitate and PRP) may be particularly suitable for preparation of fibrin sealant/glue that will be subsequently deficient in t-PA-deficient and plasminogen. "Biological glue/sealant" as used herein is a complex blood or plasma-derived product which is increasingly used as a biodegradable tissue adhesive or sealant to stop or control bleeding in many surgical situations and to prevent leaks of different components from operated tissues, as in case of bleeding from gastrointestinal tract (GI), urinary tract, central nerve system or blood vessels. This product mimics the last step of the coagulation cascade through the cleavage of fibrinogen by thrombin, leading to the formation of a fibrin clot. The fibrin clot consolidating and adhering to the application site acts as a fluid tightness agent able to hold tissues or materials in a required configuration and preventing leaks of components (tissue components, that may include parts of organs and the like) and blood, while evidencing hemostatic and healing properties.

Usual components of commercial fibrin sealant products include coagulation factors such as: fibrinogen, factor XIII, thrombin, as well as fibrinolytic protein plasminogen. Interaction of the content of the biological glue with surrounding tissues that secrete plasminogen activators will then cleave plasminogen within the glue to plasmin, which in turn will degrade fibrin clot, thus favoring bleeding. Thus, the biological glue of the invention that may comprise tPA-deficient and/or plasminogen-deficient, specifically, t-PA-deficient and plasminogen-deficient blood and blood-derived product/s exhibits reduced fibrinolytic activity, thereby acting as an effective glue/sealant.

In yet some further embodiments, the biological glue of the invention may further comprise at least one inhibitor of at least one of plasmin, plasminogen and plasminogen activator. More specifically, the inhibitors may be inhibitors of fibrinolysis, such as $\alpha 2$-anti-plasmin, tPA-mutant, PAI-1, aprotonin and lysine analogs like tranexamic acid. In some particular embodiments, in addition to $\alpha_2$-anti-plasmin, the biological glue of the invention may further comprise an effective amount of Alpha-1 Antitrypsin (for example, 1.5-3.5 gram/liter). Alpha-1 Antitrypsin inhibits a wide range of proteases and by that protects tissues from degradation. Therefore, the tPA and plasminogen free blood, blood products, plasma or plasma products used by the biological glue of the invention may be further enriched with Alpha-1 Antitrypsin.

Alpha-1 Antitrypsin or $\alpha_1$-antitrypsin (A1AT) is a protease inhibitor belonging to the serpin superfamily. It is generally known as serum trypsin inhibitor. Alpha 1-antitrypsin is also referred to as alpha-1 proteinase inhibitor (A1PI) because it inhibits a wide variety of proteases. It protects tissues from enzymes of inflammatory cells, especially neutrophil elastase, and has a reference range in blood of 1.5-3.5 gram/liter, but the concentration can rise many fold upon acute inflammation. In its absence (such as in alpha 1-antitrypsin deficiency), neutrophil elastase is free to break down elastin, which contributes to the elasticity of the lungs, resulting in respiratory complications such as emphysema, or such as emphysema, or such as emphysema, or chronic obstructive pulmonary diseas (COPD) in adults and cirrhosis in adults or children. Disorders of this protein include alpha 1-antitrypsin deficiency, an autosomal codominant hereditary disorder in which a deficiency of alpha 1-antitrypsin leads to a chronic uninhibited tissue breakdown. This causes the degradation especially of lung tissue, and eventually leads to characteristic manifestations of pulmonary emphysema. Evidence has shown that cigarette smoke can lead to oxidation of methionine 358 of $\alpha_1$-antitrypsin (382 in the pre-processed form containing the 24 amino acid signal peptide), a residue essential for binding elastase; this is thought to be one of the primary mechanisms by which cigarette smoking (or second-hand smoke) can lead to emphysema. Because A1AT is expressed in the liver, certain mutations in the gene encoding the protein can cause misfolding and impaired secretion, which can lead to liver cirrhosis.

Therefore, the Alpha-1 Antitrypsin in the plasminogen deficient plasma or biological glue should inhibit the proteases that could cleave biological glue. The presence of Alpha-1 Antitrypsin will be of particular relevance in areas of inflammation where proteases such as neutrophil elastase are released. Furthermore, in surgical interventions in the gastrointestinal tract (GI), the presence of Alpha-1 Antitrypsin in the biological glue or any other products of the invention may inhibit the proteases of the GI tract and by this may stabilize the biological glue and prevent the formation of post-operative GI fistulas. In addition, the presence of alpha-1 antitrypsin together with $\alpha 2$-antiplasmin in the t-PA-free and plasminogen free plasma will make possible the treatment of recent and old GI and urinary tract fistulas.

In contrast to other commercial preparations, the t-PA-deficient and plasminogen-depleted plasma-derived fibrin sealant/glue of the invention has a significant advantage, because the removal of t-PA and plasminogen from the glue product prevents clot lysis, as disclosed in the present invention in Examples 1, 2 and 5 and FIGS. 5 and 6. A stable clot that is resistant to lysis is a substantial improvement over the previous preparations of biological glue particularly in situations where treatment or prevention of bleeding is required.

Still further, it should be appreciated that the biological glue/sealant of the invention may comprises at least one coagulation promoting factor such as fibrinogen and at least one of, fibrinogen cleaving enzyme and calcium. It should be noted that each of said coagulation promoting agent/s may be optionally provided within a separate compartment. In some specific embodiments, the biological glue of the invention may further comprise at least one coagulation promoting agent, specifically, at least one of, fibrinogen, thrombin or any fibrinogen cleaving enzyme and calcium. It should be noted that each of the coagulation promoting agent may be optionally provided within a separate compartment.

In some embodiments, the fibrinogen conversion to fibrin could be initiated by tissue factor (TF) or kaolin. Fibrinogen cleaving enzyme that may be used by the biological glue of the invention, may be reptilase. In other embodiments, the fibrinogen cleaving enzyme may be thrombin.

More specifically, thrombin is a catalytic enzyme derived from prothrombin (factor II) after its cleavage. Thrombin by itself cleaves a number of coagulation factors. It cleaves fibrin peptides A and B from fibrinogen to form fibrin monomers that spontaneously polymerize to form a primary fibrin clot. Thus, in some embodiments, the biological glue of the invention may further comprise thrombin.

Reptilase, an enzyme found in the venom of Bothrops snakes, has activity similar to thrombin. Reptilase differs from thrombin by releasing fibrinopeptide A, but not fibrinopeptide B, in its cleavage of fibrinogen. Thus, final product of reptilase cleavage is also a primary fibrin clot. In yet some further embodiments, the biological glue of the invention may further comprise reptilase.

As have been already described herein, the outcome of the interaction of thrombin or any other fibrinogen cleaving enzyme with fibrinogen is an instant cleavage of fibrinogen and formation of primary fibrin clot. In some embodiments, the primary fibrin clot could be further stabilized by factor XIII and calcium. Therefore, effective topical delivery of a biological glue requires that the coagulation promoting and fibrinogen cleaving agents be hold in separate syringes, containers, tubes, vessels and the like. One contain, for example, syringe should contain as active product, a coagulation promoting proteins/agents, such as the blood or blood product of the invention that may be further supplemented with fibrinogen with or without factor XIII, while another syringe or container should contain as another active product—a coagulation promoting proteins/agents that could be fibrinogen cleaving enzyme, such as reptilase, tissue factor (TF), kaolin or thrombin and calcium. In this way no clots are formed within the syringes. Upon the requirement of clot formation outside the syringes, on the surface of a tissue, each one of the separate syringes release their contents into a common container/tubing/spray device, which is suitable for topical application.

Thus, in addition to the product of the invention that is devoid of tPA and plasminogen, the biological glue of the invention may comprise active products, as described herein above, that are kept in separate syringes or containers, while these active products can be further delivered by an immediate release into a common container/tubing form for topical application.

In yet further embodiments, the biological glue or sealant of the invention may further comprises at least one inhibitor of at least one of plasmin, plasminogen and plasminogen activator. More specifically, such inhibitor may be at least one of aprotinin, tranexamic acid and ε-aminocaproic acid (EACA).

It should be further appreciated that in some embodiments, the biological glue or sealant (e.g., fibrin glue/sealant) of the invention may be derived from at least one of t-PA-deficient and/or plasminogen-deficient PRP, t-PA-deficient and/or plasminogen-deficient FFP, and t-PA-deficient and/or plasminogen-deficient cryoprecipitate. In some embodiments, the t-PA-deficient and/or plasminogen-deficient blood product, FP, PRP or FFP, could be supplemented or not with exogenous fibrinogen. In yet some further embodiments, the PRP, FFP and cryoprecipitate are of autologous human or allogeneic human source. In yet some further embodiments such biological glue may further comprise fibrinogen, and at least one of fibrinogen cleaving enzyme and calcium, wherein said fibrinogen cleaving enzyme may be at least one of thrombin and reptilase. In some specific embodiments, tissue factor or kaolin can be also used to activate the extrinsic or intrinsic coagulation pathways.

Two antifibrinolytic agents, EACA and tranexamic acid are synthetic lysine analogs. Fibrinolysis (clot lysis) is accelerated by binding of plasminogen to lysine residues on fibrin. EACA and tranexamic acid inhibit fibrinolysis by competitively blocking this binding.

Aprotinin is a naturally occurring proteinase inhibitor obtained from human lung. It expresses its antifibrinolytic properties by inhibiting plasmin through interaction with the catalytic site.

Accordingly, depletion and/or inactivation in clot lysis proteins, specifically, t-PA and/or plasminogen, on one hand and addition of further antifibrinolytic agents on the other hand, renders improved stability to the formed clot, thereby providing more efficient modality for treating or preventing local bleeding or bleeding leaks. The leaks could be the context of the gastro-intestinal (GI) or urinary tracts or in the context of cerebro-spinal fluid (CSF), in case of neurosurgery.

It should be appreciated that in some embodiments, the biological sealant/glue of the invention may be adapted for topical administration. By "topical administration" it is meant that the fibrin sealant/glue of the invention or any of the tPA and plasminogen deficient products of the invention may be administered locally. Specifically, the product (either glue or any other product of the invention) is applied onto a surface by a mean of external injection, spraying or any other superficial application. The fibrin sealant/glue or any other tPA and plasminogen deficient products of the invention may include any means for local application, or may be designed in a form adapted for local administration, for example, transdermal patches, ointments, lotions, creams, gels, drops, suppositories, sprays, liquids and powders. Still further, it must be understood that the term "topical" refers to local application/s that is not a systemic application that although include, is not limited to dermal or transdermal application. Local application may be further applied locally on the treated surface, organ or tissue by using catheters, syringe or any other applicator or any other pouring, deeping, immersing or coating means. Conventional pharmaceutical carriers, aqueous, powder or oily bases, thickeners and the like may be necessary or desirable.

In yet some specific and not limiting embodiments, the glue of the invention may be adapted for transdermal delivery. Transdermal delivery may be accomplished in various ways. By "transdermal" herein is meant the passing through the skin and into a subject's blood stream, whereby to provide a systemic effect. Whilst the term embraces transmucosal, i.e. passing through mucosal tissue so as to embrace sublingual, buccal, vaginal and rectal delivery, typically transdermal delivery is affected through a subject's skin. For this reason, references are generally made herein to skin for simplicity's sake only although it will be appreciated that the transdermal delivery described herein may also be transmucosal.

According to some embodiments, a transdermal delivery system may be provided comprising the biological sealant/glue of the invention. Such glue may be presented in a number of different ways, a typical presentation being one that permits transdermal delivery. For example, the fibrin sealant/glue may be contained within an adhesive patch designed to be affixed to the skin of a patient, or formulated into a capsule or sachet susceptible to easy rupture. Other formulations, such as topically applied gels, are known to the skilled person. Typically the biological sealant/glue of the present invention are presented as adhesive transdermal patches. Such patches comprising the biological glue of the invention constitute a delivery system for transdermal delivery of the composition of the invention contained within them.

By a patch or adhesive patch herein is meant material adapted for adhesion to a subject's skin or mucosal tissue. Typically patches herein have a substantial degree of rigidity and, in use, comprise a backing layer exposed to the environment and a biological sealant/glue of the invention beneath the backing layer. However, the patches of the invention may also be of a non-rigid nature.

As noted above, biological adhesives require a further contribution of exogenous thrombin enzyme. Additional components may be required to perform coagulation including the calcium ion, but also antibiotics or growth factors.

Commercially available biological adhesives comprise most of the components cited above in dry form. However, the proteins activated by thrombin, such as fibrinogen and factor XIII must be isolated from thrombin because their association generates fibrin in a few seconds after reconstitution in liquid mixture.

Consequently, biological glue kits may comprise at least two components, firstly, a lot based on the proteins activated by thrombin and on the other hand, a lot based on thrombin.

Suitable devices for delivery of the biological glue may therefore enable reconstitution and mixing of the two lots, for example specific double syringes and needles or spray for direct application.

For example, a suitable double-syringe may be composed by a mixer nosecone, topped by a blunt applicator needle, attached to the nozzle to facilitate mixing of the two syringe components. When the common plunger is depressed, the fibrin sealer solution and the thrombin solution are combined in the nosecone, in equal volumes, to form the resulting fibrin sealant that is directly applied to the designated tissues. It should be noted that for topical application of the biological glue/sealant of the invention any suitable applicator may be used, for example, the applicator described herein above or any modifications thereof.

A further aspect of the invention relates to a method for the treatment, prophylaxis, amelioration, inhibition or delaying the onset of bleeding, hemostatic disorders and any bleeding or pathologic condition associated therewith. In yet some further embodiments, the methods of the invention may be applicable for treating disorders that include at least one of or any conditions associated with bleeding tendency. More specifically, the method of the invention may comprise the step of administering to a subject in need thereof an effective amount of at least one blood and blood-derived product that may be tPA-deficient and/or devoid of plasminogen or plasmin activity, or of any composition or biological glue or sealant comprising the same. In yet some further embodiments, the product used by the methods of the invention may be a t-PA-deficient blood or blood-derived product. In some other specific embodiments, the product used by the methods of the invention may be devoid of plasminogen and/or plasmin activity. In yet some specific embodiments, the product of the invention may be a t-PA-deficient and devoid of plasminogen and/or plasmin activity. In some specific embodiments, the method of the invention may involve the step of administration of t-PA and/or plasminogen deficient blood or t-PA and plasminogen deficient blood-derived product or of any composition or biological glue or sealant comprising the same. In some specific embodiments, the product used by the methods of the invention may be a t-PA-deficient blood or blood-derived product. In some other specific embodiments, the product used by the methods of the invention may be a plasminogen-deficient blood or blood-derived product. In yet some specific embodiments, the product used by the methods of the invention may be a t-PA-deficient and plasminogen-deficient blood or blood-derived product.

In some specific embodiments, the methods of the invention employ administering to the bleeding subject or to the subject that suffers of any hemostatic disorder, a therapeutically effective amount of at least one of t-PA-deficient and plasminogen-deficient blood or blood-derived products of the invention or any combination thereof, wherein in some specific embodiments, the product may be at least one of whole blood, plasma, fresh frozen plasma (FFP), platelet rich plasma (PRP) and cryoprecipitate. In some embodiments, the blood and blood-derived product used by the methods of the invention may contain fibrinogen. In specific embodiments the product of the invention may further comprise at least one inhibitor of at least one of plasmin, plasminogen and plasminogen activator or any combination thereof. In some embodiments the blood product of the invention may be derived from autologous source (e.g., blood, blood product, plasma). In yet other embodiments, the product used by the method of the invention may be derived from allogeneic source.

In thus far, certain embodiments provide the method comprising the step of administering to the subject a therapeutically effective amount of a biological glue or sealant of the invention comprising a t-PA-deficient and plasminogen-deficient blood-derived product. More specifically, such product may be at least one of t-PA-deficient and plasminogen-deficient PRP, t-PA and plasminogen-deficient FFP, and t-PA-deficient and plasminogen-deficient cryoprecipitate.

It should be appreciated that the biological glue/sealant used by the method of the invention may comprise at least one coagulation promoting factor such as fibrinogen and at least one fibrinogen cleaving enzyme. Each of said coagulation promoting agent may be optionally provided within a separate compartment.

In some specific embodiments, the glue or sealant used by the method of the invention may further comprise at least one inhibitor of at least one of plasmin, plasminogen and plasminogen activator, wherein said inhibitor is at least one of aprotinin, tranexamic acid and ε-aminocaproic acid (EACA).

In some specific embodiments, the method of the invention may be applicable for the treatment, prevention, prophylaxis, amelioration, inhibition of bleeding, hemostatic disorders and any bleeding or pathologic condition associated therewith in a subject in need thereof, the method comprising the step of administering to said subject a therapeutically effective amount of at least one t-PA-deficient and plasminogen-deficient blood-derived product or of any composition or biological glue or sealant comprising the same.

Yet further, the invention discloses that the product may be at least one of whole blood, plasma, fresh frozen plasma (FFP), platelet rich plasma (PRP) and cryoprecipitate. Such blood and blood-derived product in some embodiments, may contain fibrinogen. In specific embodiments the product used by the method of the invention may further comprise at least one inhibitor of at least one of plasmin, plasminogen and plasminogen activator or combination thereof. In a specific embodiment such inhibitor may be at least one of α2-anti-plasmin, tPA-mutant and PAI-1, antitrypsin or lysine analogs like tranexamic acid or aprotinin. In some embodiments the blood product of the invention is derived from autologous source (blood, blood product, plasma and the like). In yet another embodiment the said product may be derived from allogeneic source.

In yet further embodiments the product administered by the method of the invention may be suitable for parenteral administration. Thus, in some embodiments, the product of the invention may be administered parenterally, to the treated subject. It should be noted that any of the products disclosed herein before in connection with other aspects of the invention may be applicable in any of the methods of the invention.

The phrases "parenteral administration" and "administered parenterally" as used herein means modes of administration other than enteral and topical administration, usually by injection including subcutaneous, intramuscular, intraperitoneal (IP), intravenous (IV) and intradermal) administration. The nature, availability and sources, and the administration of all such compounds including the effective amounts necessary to produce desirable effects in a subject are well known in the art.

In certain embodiments, the methods of the invention may be particularly applicable for subjects suffering from a hemostatic disorder that may be hereditary or acquired bleeding disorders.

Hemostatic disorders are bleeding disorders classified as either hereditary or acquired. Acquired bleeding disorders are disorders where bleeding is induced by an external (acquired) cause such as trauma, surgery or fibrinolytic treatment, as will be discussed herein after.

Bleeding disorders caused by inherited deficiencies of one or more coagulation factors are rare disorders distributed worldwide. Homozygotes or compound heterozygotes for the mutant genes responsible for these defects exhibit bleeding manifestations that are of variable severity and usually related to the extent of the decreased activity of the particular coagulation factor.

In yet further embodiments the methods of the invention are applicable for the treatment, prophylaxis, amelioration, inhibition or delaying the bleeding associated with hereditary hemostatic disorder and undefined bleeding tendency.

"Hereditary hemostatic disorder" as used herein relates to a hereditary deficiency in at least one coagulation factor. More specifically, numerous mutations have been identified in genes encoding coagulation factors I, II, V, VII, X and XI, that lead to deficiency of at least one of said factors or to impaired activity thereof. Homozygotes for these mutations exhibit bleeding tendency either spontaneously or following trauma/surgery. Heterozygotes for the various deficiencies rarely display a bleeding tendency.

Undefined tendency to bleed, as used herein, relates to a condition of bleeding tendency while a precise diagnosis of this condition cannot be established.

Some patients referred for an evaluation of mild bleeding symptoms have an undiagnosed bleeding tendency that may not have been recognized until challenging event that induce bleeding such as surgery or childbirth occur. Clinical variability with regard to bleeding manifestations is common among such individuals, suggesting that environmental and other genetic factors may ameliorate bleeding risks. Although mild bleeding problems may not become evident until exposure to significant hemostatic challenges (such as surgery, dental extractions, major trauma, menarche or childbirth), the predictive risk of bleeding following surgery has not been established for these individuals. Gender has an influence on the manifestations of bleeding. Females are more commonly referred for evaluation because of troublesome bleeding with menses and/or childbirth. In addition, bleeding that persists or becomes problematic 24 hours or longer after dental extractions raises the possibility of a bleeding disorder. Failure to establish a diagnosis in a patient with mild mucocutaneous bleeding is a common problem in practice.

Normal laboratory tests are a hallmark for diagnosis of the undefined bleeding tendency. Failure to establish the diagnosis can be problematic for patient who needs to undergo surgery or childbirth.

For mild bleeding symptoms of patients with undefined bleeding disorders, fibrinolytic inhibitor therapy with ε-aminocaproic acid or tranexamic acid may be used for dental and oral surgeries and it may reduce bleeding with other operative procedures. However, in case severe bleeding develops for example during surgery or childbirth, blood or blood-derived components are required.

Thus, it should be appreciated that the method of treatment or prophylaxis of bleeding with the antifibrinolytic t-PA-deficient and plasminogen-depleted products of the invention may be particularly suitable for this group of patients.

It should be appreciated that the t-PA-deficient and plasminogen deficient blood and blood-derived products and compositions of the invention, and methods described by the invention, may be applicable for any form of bleeding that accompanies hereditary hemostatic disorders caused by a deficiency in at least one of factor XI, factor X, factor V, factor VII, factor II (prothrombin) and factor I (fibrinogen) as disclosed herein.

In yet some further embodiments, the methods of the invention may be applicable for treating disorders characterized by hereditary deficiencies of the coagulation factors I, II, V, VII, X and XI that include at least one of or any bleeding tendency associated therewith.

Hereditary deficiencies of the coagulation factors I, II, V, VII, X and XI are autosomal recessive bleeding disorders that have been described in most populations. Their relative frequency varies among populations partly as a result of high frequencies of specific mutant genes in inbred populations. Several population surveys indicate that common among these bleeding disorders are factors XI and VII deficiency, less common disorders are factors V and X deficiency and afibrinogenemia, and the rarest disorders are factor II (prothrombin) and factor XIII deficiency. The severity of bleeding manifestations in affected patients who are homozygotes or compound heterozygotes for a mutant gene is variable and usually related to the extent of the deficiency. Some patients have only mild bruising or display excessive bleeding only following trauma. Other patients, usually with less than 1 percent of normal factor VII, XIII, or X activity, can exhibit intracranial hemorrhages and hemarthroses similar to patients with severe hemophilias.

In some specific embodiments, the method of the invention may be applicable for treating, preventing, reducing attenuating or inhibiting bleeding associated with hereditary factor XI deficiency, or any acquired bleeding or hemostatic condition in patients suffering from factor IX deficiency.

Hereditary factor XI deficiency is transmitted as autosomal recessive trait. The disorder is exhibited in homozygotes or compound heterozygotes as a mild to moderate bleeding tendency that is mainly injury related. Affected subjects have been described in most populations but in Jews, particularly of Ashkenazi origin, the disorder is common.

Factor XI deficiency as a result of a dysfunctional protein is rare and the majority of the patients have a decreased factor XI protein level. Altogether, above 150 mutations have been reported in non-Jewish and Jewish patients of various origins most of them being missense mutations.

Most bleeding manifestations in homozygotes and compound heterozygotes are injury related. Excessive bleeding can occur at the time of injury or begin several hours or days following trauma. The bleeding tendency varies depending upon the hemostatic challenge and the variable sites of injury. Surgical procedures involving tissues with high fibrinolytic activity (urinary tract, tonsils, nose, tooth sockets) frequently are associated with excessive bleeding in patients with severe factor XI deficiency, irrespective of the genotype. Site-related bleeding tendency now can be understood in light of the demonstrated function of factor XI in preventing clot lysis. Factor XI deficiency by itself is associated with increased fibrinolysis, therefore, the additional bleeding risk of surgery at sites rich in fibrinolysis in these patients may increase the bleeding tendency even further.

The treatment of bleeding patients with factor XI deficiency is by FFP. Patients with severe factor XI deficiency who must undergo a surgical procedure should be carefully evaluated and meticulously prepared for the operation. Use of an anti-fibrinolytic agent should be considered in patients undergoing operation at a site with high local fibrinolytic activity. Therefore, in some embodiments, the tPA and plasminogen-deficient FFP provided by the invention may be particularly relevant for treating patients with Factor XI deficiency, specifically, any of the conditions discussed above.

In other embodiments, the method of the invention may be applicable for treating, preventing, reducing attenuating, inhibiting bleeding associated with hereditary factor VII deficiency, or any acquired bleeding or hemostatic condition in patients suffering from factor VII deficiency.

Hereditary deficiency of factor VII is a rare autosomal recessive disorder that has been observed in most populations. A presumptive diagnosis can be easily made because factor VII deficiency is the only coagulation disorder that produces a prolonged clotting time test prothrombin time (PT). Most mutations causing factor VII deficiency have been missense mutations.

Bleeding manifestations occur in homozygotes and in compound heterozygotes for factor VII deficiency. Patients who have factor VII activity less than 1 percent of normal, frequently present a severe bleeding manifestations such as hemarthroses leading to severe arthropathy and life-threatening intracerebral hemorrhage.

Patients with slightly higher levels of factor VII (factor VII activity of 5 percent of normal or more) have a much milder disease, characterized by epistaxis, gingival bleeding, menorrhagia, and easy bruising. Some surgical procedures such as dental extractions, tonsillectomy, and procedures involving the urogenital tracts frequently are accompanied by bleeding when no prior therapy is instituted prior to the procedure. In contrast, surgical procedures such as laparotomy, herniorrhaphy, appendectomy, and hysterectomy have been uneventful. This apparent discrepancy can be explained by different extents of local fibrinolysis exhibited by the respective traumatized tissues.

Replacement therapy by FFP is essential in patients who present with severe hemorrhage, such as hemarthrosis or intracerebral bleeding. When surgery is required, the site of surgery should be considered, as dental extractions, tonsillectomy, nose surgery, and urologic interventions are likely to be associated with bleeding because of local fibrinolysis. Therefore, in some embodiments, the tPA and plasminogen-deficient FFP provided by the invention may be particularly relevant for treating patients with Factor VII deficiency, specifically, any of the conditions discussed above.

In yet further embodiments, the method of the invention may be applicable for treating, preventing, reducing attenuating, inhibiting bleeding associated with hereditary factor X deficiency, or any acquired bleeding or hemostatic condition in patients suffering from factor X deficiency.

Hereditary factor X deficiency, a moderate to severe bleeding tendency, is an autosomal recessive disorder. The currently described 95 mutations that cause factor X deficiency include large deletions, small frameshift deletions, nonsense mutation, and missense mutations. The clinical manifestations of factor X deficiency are related to the functional levels of factor X. Individuals with severe factor X deficiency and functional factor X levels less than 1 percent of normal bleed spontaneously and following trauma. Bleeding occurs primarily into joints and soft tissues, however, bleeding from mucous membranes such as Menorrhagia may be especially problematic in women. More unusual bleedings are intracerebral hemorrhage, intramural intestinal bleeding (which can produce symptoms like those of an acute abdomen), urinary tract bleeding, and soft tissue bleeding with development of hemorrhagic pseudocysts or pseudotumors. In individuals with mild deficiencies of factor X bleeding is less common, usually occurring only after trauma or during or after surgery. Fresh-frozen plasma is used to treat patients with factor X deficiency. Therefore, in some embodiments, the tPA and plasminogen-deficient FFP provided by the invention may be particularly relevant for treating patients with Factor X deficiency, specifically, any of the conditions discussed above.

In yet another embodiment, the invention may be applicable for treating, preventing, reducing attenuating, and inhibiting bleeding associated with hereditary factor V deficiency, or any acquired bleeding or hemostatic condition in patients suffering from factor V deficiency.

Hereditary factor V deficiency is among the less common inherited bleeding disorders and manifests in homozygotes or compound heterozygotes as a moderate bleeding tendency. Factor V deficiency is inherited as an autosomal recessive trait. Heterozygotes, whose plasma factor V activity ranges between 25 and 60 percent of normal, usually are asymptomatic, Assays of factor V protein indicate that most homozygotes and compound heterozygotes have a true deficiency rather than a dysfunctional protein. Above 80 total distinct mutations have been identified, of which one quarter are missense, Homozygous or compound heterozygous patients whose factor V level ranges from less than 1 to 10 percent of normal exhibit a lifelong bleeding tendency. Common manifestations include ecchymoses, epistaxis, gingival bleeding, hemorrhage following minor lacerations, and menorrhagia. Postpartum hemorrhage occurs in more than 50 percent of pregnancies in patients with severe factor V deficiency. Bleeding from other sites is less common. Trauma, dental extractions, and surgery confer a high risk of excessive bleeding. In case a severe spontaneous bleeding occurs, or surgery is performed, fresh-frozen plasma replacement should be given. When planning plasma replacement therapy it is important to consider surgical procedures at sites having high local fibrinolytic activity such as the urogenital tract, oral cavity, and nose, since surgery at these sites will result in excessive bleeding and postpartum hemorrhage is common. Therefore, in some embodiments, the tPA and plasminogen-deficient products provided by the invention may be particularly relevant for treating patients with Factor V deficiency, specifically, any of the conditions discussed above.

In certain embodiments, the methods of the invention may be particularly applicable for treating, preventing, reducing attenuating, inhibiting bleeding associated with hereditary factor II deficiency, or any acquired bleeding or hemostatic condition in patients suffering from factor II deficiency.

Inherited factor II (prothrombin) deficiency is one of the rarest coagulation factor deficiencies. It presents in two forms: type I, true deficiency (hypoprothrombinemia), and type II, in which dysfunctional prothrombin is produced (dysprothrombinemia). These autosomal recessive disorders are genetically heterogeneous, and characterized by a mild to moderate bleeding tendency.

Abnormalities of prothrombin are inherited in an autosomal recessive manner. Among individuals with type I deficiency, heterozygotes exhibit prothrombin levels that are approximately 50 percent of normal, whereas homozygotes display levels that typically are less than 10 percent of normal. Above fifty mutations that cause prothrombin deficiency have been identified, most of which are missense mutations.

Inherited types I and II deficiencies are characterized by mild to moderate mucocutaneous and soft-tissue bleeding that usually correlates with the degree of functional prothrombin deficiency. With prothrombin levels of approximately 1 percent of normal, bleeding may occur spontaneously or following trauma. Surgical bleeding may be significant. Menorrhagia, epistaxis, gingival bleeding, easy bruising, and subcutaneous hematomas may occur.

Replacement therapy in patients with inherited prothrombin deficiency consists of administration of FFP. Therefore, in some embodiments, the tPA and plasminogen-deficient FFP provided by the invention may be particularly relevant for treating patients with Factor II deficiency, specifically, any of the conditions discussed above.

In yet another embodiment, the invention may be applicable for treating, preventing, reducing attenuating, inhibiting bleeding associated with hereditary fibrinogen deficiency or any acquired bleeding or hemostatic condition in patients suffering from hereditary fibrinogen deficiency.

"Fibrinogen (factor I) deficiency" as used herein relates to hereditary fibrinogen abnormalities comprises the afibrinogenemia (complete absence of the fibrinogen), dysfibrinogenemia and hypodysfibrinogenemia. Inherited disorders of fibrinogen are rare and can be subdivided into type I and type II disorders. Type I disorders (afibrinogenemia and hypofibrinogenemia) affect the quantity of fibrinogen in circulation. Type II disorders (dysfibrinogenemia and hypodysfibrinogenemia) affect the quality of circulating fibrinogen. Afibrinogenemia, the most severe form of fibrinogen deficiency, is characterized by autosomal recessive inheritance and the complete absence of fibrinogen in plasma.

Dysfibrinogenemia is defined by the presence of normal levels of functionally abnormal plasma fibrinogen. Hypodysfibrinogenemia is defined by low levels of a dysfunctional protein. These are heterogeneous disorders caused by many different mutations in the three fibrinogen coding genes. Dysfibrinogenemias and hypodysfibrinogenemias are autosomal dominant disorders. Most affected patients are heterozygous for mis sense mutations in the coding region of one of the three fibrinogen genes. Because the secreted fibrinogen hexamer contains two copies of each of the three fibrinogen chains, and the resulting fibrin network contains multiple copies of the molecule, heterozygosity for one mutant allele is sufficient to impair the structure and function of the fibrin clot.

Bleeding because of afibrinogenemia usually manifests in the neonatal period, with 85 percent of cases presenting umbilical cord bleeding, but a later age of onset is not unusual. Bleeding may occur in the skin, gastrointestinal tract, genitourinary tract, or the central nervous system with intracranial hemorrhage being the major cause of death. There is an intriguing susceptibility of spontaneous rupture of the spleen in afibrinogenemic patients. Menstruating women may experience menometrorrhagia. In addition, first trimester abortion is usual in afibrinogenemic women. These patients may also have antepartum and postpartum hemorrhage. Hemoperitoneum after rupture of the corpus luteum has also been observed.

Replacement therapy with fibrinogen containing commercial products is the only option for treatment of patients with inherited fibrinogen deficiency. Therefore, in some embodiments, the methods the invention may be particularly relevant for treating patients with fibrinogen deficiency, specifically, any of the conditions discussed above. Particularly, in some embodiments where the product used by the invention is supplemented with fibrinogen.

In contrast to the commercial preparations of blood-derived products used for the treatment of hereditary coagulation factor deficiencies, t-PA-deficient and plasminogen-depleted plasma-derived products of the invention have a substantial advantage, because in addition to providing the missing factor (pro-coagulant quality) the removal of t-PA and plasminogen from the products renders them antifibrinolytic qualities that are essential for preventing further clot lysis in case of bleeding.

In some embodiments, the methods of the invention may be applicable for treating acquired hemostatic disorders. The acquired hemostatic disorder may be at least one of surgery-induced bleeding, trauma-induced bleeding, acute gastrointestinal bleeding, bleeding associated with burns, hemorrhagic stroke, lung injury associated with emphysema and chronic obstructive pulmonary disease (COPD), bleeding associated with childbirth, disseminated intravascular coagulation (DIC), and bleeding resulting from fibrinolytic or thrombolytic therapy.

In some specific embodiments, the method of the invention may be applicable for treating, preventing, reducing, attenuating, and inhibiting bleeding associated with surgical procedures, specifically, minor or major surgical procedures.

Surgical procedures are a great challenge to the hemostatic system, especially when surgery is performed at places rich in fibrinolytic proteins. Even patients with no or mild to moderate bleeding disorders can bleed excessively following surgery. In addition to the extent of the surgical trauma, the magnitude of the fibrinolytic activity at the surgical site must be considered.

It should be understood that in cases the surgical procedures are elective, expected or not urgent (e.g., cesarean surgery, or any other major surgery that allow sufficient time for pre-operative preparations), the products of the invention may be used for pre-operative treatment to facilitate prevention or reduction of excessive bleeding during the surgical intervention. Thus, in some embodiments, the invention may provide a preventive method particularly useful for patients having hereditary disorders, patients suffering from hyperfibrinolysis and/or patients that are expected to be operated.

In a further specific embodiment the method of the invention is suitable for treating trauma-induced bleeding (traumatic bleeding).

Traumatic bleeding can be caused by any type of injury, for example any injury caused by, work and car accidents, combats or falls. There are different types of traumatic wounds which may cause bleeding. In general, trauma causes damage to a blood vessels that in turn causes blood to flow externally outside the body or internally into body organs such as brain, lung, liver, kidney, spleen or into body cavities, such as thorax and abdomen.

Beside the physical measures to stop the bleeding, blood and blood-derived components are usually administered in order to initiate blood clotting, which will eventually result in a cessation of bleeding.

The tPA and plasminogen deficient blood and blood-derived products of the invention display an advantage over the commercial blood-derived products, because they provide an additional antifibrinolytic quality, which will prevent dissolution of a formed clot that might be essential for rapid cessation of bleeding.

In some specific embodiments the blood-derived products of the invention comprising t-PA-deficient and/or plasminogen-deficient blood, t-PA-deficient and/or plasminogen-deficient plasma, t-PA-deficient and/or plasminogen-deficient FFP and t-PA-deficient and/or plasminogen-deficient plasma derived glue/sealant supplemented or not with exogenous fibrinogen, as well as methods of using them, may be suitable for treatment of acute or chronic gastrointestinal bleeding.

"Gastrointestinal (GI) bleeding", also known as gastrointestinal hemorrhage, as used herein, relates to all forms of bleeding in the gastrointestinal tract, from the mouth to the rectum. "Acute gastrointestinal bleeding" means that there is a significant blood loss over a short time causing acute blood loss and hemorrhagic shock. Symptoms may include vomiting (hemathemesis) either red blood or black blood (due to digested blood also called "coffee ground"), bloody stool, or black stool (digested blood called melena). In contrast, chronic gastrointestinal bleeding is bleeding of small amounts of blood over a long time. In this case the symptoms are of iron-deficiency anemia.

GI bleeding is typically divided into two main types: upper gastrointestinal bleeding and lower gastrointestinal bleeding. Causes of upper GI bleeds include: peptic ulcer disease, esophageal varices, that may occur in some embodiments, due to liver cirrhosis and cancer, among others. Causes of lower GI bleeds include: hemorrhoids, cancer, and inflammatory bowel disease among others. Endoscopy of the lower and upper gastrointestinal track may locate the area of bleeding. Medical imaging may be useful in cases that are not clear.

Acute upper GI bleed is more common than lower GI bleed. An upper GI bleed occurs in 50 to 150 per 100,000 adults per year. A lower GI bleed is estimated to occur in 20 to 30 per 100,000 per year. It results in about 300,000 hospital admissions a year in the United States. Risk of death from a GI bleed is between 5% and 30%. Risk of bleeding is more common in males and increases with age.

The most common source of upper gastrointestinal bleeding is peptic ulcer. Esophageal inflammation and erosive disease are the next most common causes. In those with liver cirrhosis, 50-60% of bleeding is due to esophageal varices. Approximately half of those with peptic ulcers have an *H. pylori* infection. Other causes include gastric or duodenal ulcers, Mallory-Weiss tears, cancer, and angiodysplasia. A number of medications are found to cause upper GI bleeds: NSAIDs, COX-2 inhibitors, SSRIs, corticosteroids, and anticoagulants.

Lower gastrointestinal bleeding is typically from the colon, rectum or anus. Common causes of lower gastrointestinal bleeding include hemorrhoids, cancer, angiodysplasia, ulcerative colitis, Crohn's disease, and aortoenteric fistula.

The initial focus of the treatment of acute gastrointestinal bleeding is on resuscitation, beginning with airway management and fluid resuscitation using intravenous fluids and blood.

Colonoscopy is useful for the diagnosis and treatment of lower GI bleeding. A number of techniques may be employed including: clipping, cauterizing, and sclerotherapy. Surgery, while rarely used to treat upper GI bleeds, is still commonly used to manage lower GI bleeds by cutting out the part of the intestines that is causing the problem. Angiographic embolization may be used for both upper and lower GI bleeds.

The findings of the inventors that the t-PA-deficient and plasminogen-deficient products of the invention have a decreased fibrinolytic activity (Examples), are highly valuable, and may be utilized for treating acute gastrointestinal bleeding. Specifically, parenteral administration of t-PA-deficient and plasminogen-deficient blood and t-PA-deficient and plasminogen-deficient FFP of the invention to a patient presented with acute gastrointestinal bleed may provide an additional benefit by more rapid cessation of bleeding due to the ability of these products to prevent dissolution of formed clots (FIG. 5, FIG. 6A-C). In addition, in case there is a clinical indication to use biological glue to stop local bleed in a patient with acute gastrointestinal hemorrhage, the implementation of the t-PA-deficient and plasminogen-deficient blood or plasma derived glue/sealant of the invention may provide an additional hemostatic value in stopping rapidly the bleed, due to its antifibrinolytic quality.

In other particular embodiments, the products and methods of the invention may be suitable for treatment of burns, and specifically, bleeding associated with burns.

A burn is a type of injury to skin, or other tissues, caused by heat, cold, electricity, chemicals, friction, or radiation. Most burns are due to heat from hot liquids, solids, or fire. Among women in many areas of the world the risk is related to the use of open cooking fires or unsafe cook stoves. Alcoholism and smoking are other risk factors.

Burns that affect only the superficial skin layers are known as superficial or first-degree burns. They appear red without blisters and pain typically lasts around three days. When the injury extends into some of the underlying skin layer, it is a partial-thickness or second-degree burn. Blisters are frequently present and they are often very painful. Healing can require up to eight weeks and scarring may occur. In a full-thickness or third-degree burn, the injury extends to all layers of the skin. Often there is no pain and the burn area is stiff. Healing typically does not occur on its own. A fourth-degree burn additionally involves injury to deeper tissues, such as muscle, tendons, or bone.

Treatment depends on the severity of the burn. Superficial burns may be managed with little more than simple pain medication, while major burns may require prolonged treatment in specialized burn centers. Cooling with tap water may help pain and decrease damage; however, prolonged cooling may result in low body temperature. Partial-thickness burns may require cleaning with soap and water, followed by dressings. It is not clear how to manage blisters, but it is probably reasonable to leave them intact if small and drain them if large. Full-thickness burns usually require surgical treatments, such as skin grafting. Extensive burns often require large amounts of intravenous fluid, due to capillary fluid leakage and tissue swelling. The most common complications of burns involve infection.

Burns are caused by a variety of external sources classified as thermal (heat-related), chemical, electrical, and radiation. In the United States, the most common causes of burns are: fire or flame (44%), scalds (33%), hot objects (9%), electricity (4%), and chemicals (3%). Most (69%) burn injuries occur at home or at work (9%), and most are accidental, with 2% due to assault by another, and 1-2% resulting from a suicide attempt. These sources can cause inhalation injury to the airway and/or lungs, occurring in about 6%.

At temperatures greater than 44° C. (111° F.), proteins begin losing their three-dimensional shape and start breaking down. This results in cell and tissue damage. Many of the direct health effects of a burn are secondary to disruption in the normal functioning of the skin. They include disruption of the skin's sensation, ability to prevent water loss through evaporation, and ability to control body temperature. Disruption of cell membranes causes cells to lose potassium to the spaces outside the cell and to take up water and sodium.

In large burns (over 30% of the total body surface area), there is a significant inflammatory response. This results in increased leakage of fluid from the capillaries, and subsequent tissue edema. This causes overall blood volume loss, with the remaining blood suffering significant plasma loss, making the blood more concentrated. Poor blood flow to organs such as the kidneys and gastrointestinal tract may result in renal failure and stomach ulcers.

Blood transfusions when required are recommended when the hemoglobin level falls below 6-8 g/dL. Plasma is administered as a colloid volume expander fluid.

Thus, when there is an indication to use blood or plasma and related products for the treatment of burns in a subject in need thereof. Thus, the t-PA-deficient and plasminogen-deficient blood or t-PA-deficient and plasminogen-deficient plasma products of the invention are a more appropriate alternative to the conventional blood products and therefore, in some embodiments may be used for treating subjects affected by any burn as discussed above.

In yet further embodiments the products of the invention and methods provided by the invention may be applicable for the treatment of hemorrhagic stroke or any other brain injury or trauma.

"Hemorrhagic stroke" as used herein, relates to bleeding occurring directly into the brain parenchyma. The usual mechanism is thought to be leakage from small intracerebral arteries damaged by chronic hypertension. Patients with intracerebral bleeds are more likely than those with ischemic stroke to have headache, altered mental status, seizures, nausea and vomiting, and/or marked hypertension. Even so, none of these findings reliably distinguishes between hemorrhagic and ischemic stroke. Specific symptoms may stem from focal neurologic deficits. The type of deficit depends on the area of brain involved. If the dominant (usually the left) hemisphere is involved, a syndrome consisting of the following may result: right hemiparesis, right hemisensory loss, left gaze preference, right visual field cut and aphasia. If the nondominant (usually the right) hemisphere is involved, a syndrome consisting of the following may result: left hemiparesis, left hemisensory loss, right gaze preference and left visual field cut.

Brain imaging is a crucial step in the evaluation of suspected hemorrhagic stroke and must be obtained on an emergent basis. Brain imaging aids diagnosing hemorrhage, and it may identify complications such as intraventricular hemorrhage, brain edema, or hydrocephalus. Either noncontrast computed tomography (NCCT) scanning or magnetic resonance imaging (MRI) is the modality of choice.

In case the treatment with blood products is indicated for hemorrhagic stroke, blood, FFP and platelets obtained from a blood bank are used. Taking into account the prothromboyic and antifibrinolytic quality of the t-PA-deficient and/or plasminogen-deficient blood products of the invention (Examples), it seems that they are more appropriate cessation of bleeding in a patient suffering from hemorrhagic stroke than the conventional blood products.

In some specific embodiments, the methods of the invention may be suitable for treating lung injury associated with emphysema and COPD. In more specific embodiments, the method of the invention may comprise the step of administering to the treated subject a therapeutically effective amount of t-PA-deficient and plasminogen-deficient FFP. In some specific embodiments, t-PA-deficient and plasminogen-deficient FP or t-PA-deficient and plasminogen-deficient FFP of the invention, due to its enrichment in alpha-1 antitrypsin, makes its use more appropriate for the treatment of a subject with emphysema and COPD. In these diseases leukocyte proteases break down the elasticity of the lungs resulting in lung fuller and consequent development of lung emphysema and chronic obstructive pulmonary disease (COPD). Therefore, alpha-1 antitrypsin within the t-PA-deficient and plasminogen-deficient FFP of the invention may inhibit the activity of leukocyte proteases and by this means restore the elasticity if the lung tissue.

Emphysema is a form of chronic (long-term) lung disease. People with emphysema have difficulty breathing from a limitation in blowing air out. There are multiple causes of emphysema, but smoking is by far the most common.

Emphysema is one of the main types of chronic obstructive pulmonary disease (COPD). It's called "obstructive" because people with emphysema exhale as if something were obstructing the flow of air. The other form of COPD is chronic bronchitis, which can also be caused by smoking.

Emphysema results when the delicate linings of the air sacs in the lungs become damaged beyond repair. Most commonly, the toxins in cigarette smoke create the damage. The lung changes of emphysema evolve slowly over years as the fragile tissues between air sacs are destroyed and air pockets in the lungs develop. Air becomes trapped in these spaces of damaged lung tissue. The lungs slowly enlarge, and breathing requires more effort.

This problem of emphysema is called airflow limitation. During lung function testing, it takes someone with emphysema far longer to empty their lungs than it does a person without emphysema.

Besides smoking, the other major known cause of emphysema is alpha-1 antitrypsin deficiency. However, this is a minor cause compared to smoking. Alpha-1 antitrypsin is a natural protein circulating in human blood. Its main function is to keep white blood cells from damaging normal tissues. Thus, treatment of a subject with emphysema with t-PA-deficient and plasminogen-deficient FP or t-PA-deficient and plasminogen-deficient FFP enriched in alpha-1 antitrypsin may inhibit the activity of proteases and thereby restore the elasticity to the lung tissue.

Chronic obstructive pulmonary disease (COPD) is a type of obstructive lung disease characterized by long term poor airflow. The main symptoms include shortness of breath and cough with sputum production. COPD typically worsens over time. Eventually walking upstairs or carrying things will be difficult. Chronic bronchitis and emphysema are older terms used for different types of COPD. The term "chronic bronchitis" is still used to define a productive cough that is present for at least three months each year for two years.

COPD is a type of obstructive lung disease in which chronic incompletely reversible poor airflow (airflow limitation) and inability to breathe out fully (air trapping) exist. The poor airflow is the result of breakdown of lung tissue (known as emphysema) and small airways disease (known as obstructive bronchiolitis). The relative contributions of these two factors vary between people. Severe destruction of small airways can lead to the formation of large air pockets known as bullae that replace lung tissue. This form of disease is called bullous emphysema.

Tobacco smoking is the most common cause of COPD, with a number of other factors such as air pollution and genetics playing a smaller role. In the developing world, one of the common sources of air pollution is poorly vented heating and cooking fires. Long-term exposure to these irritants causes an inflammatory response in the lungs resulting in narrowing of the small airways and breakdown of lung tissue. The diagnosis is based on poor airflow as measured by lung function tests. In contrast to asthma, the airflow reduction does not improve much with the use of a bronchodilator.

The most common symptoms of COPD are sputum production, shortness of breath, and a productive cough. These symptoms are present for a prolonged period of time and typically worsen over time. It is unclear if different types of COPD exist. While previously divided into emphysema and chronic bronchitis, emphysema is only a description of lung changes rather than a disease itself, and chronic bronchitis is simply a descriptor of symptoms that may or may not occur with COPD.

Advanced COPD leads to high pressure on the lung arteries, which strains the right ventricle of the heart and right hear failure. This situation is referred to as cor pulmonale, and leads to symptoms of leg swelling and bulging neck veins. COPD is more common than any other lung disease as a cause of cor pulmonale. Cor pulmonale has become less common since the use of supplemental oxygen.

Consequently, the t-PA-deficient and/or plasminogen-deficient FP or t-PA-deficient and plasminogen-deficient FFP of the invention may be beneficial as a complementary treatment of COPD, since its enrichment in alpha-1 antiplasmin may inhibit leukocyte's proteases and thereby repair the elastic quality to the damaged lung tissue.

In certain specific embodiments, the method of the invention may be suitable for treating, preventing, reducing, attenuating, and inhibiting bleeding associated with major surgery.

Major surgery is defined as any surgical procedure that involves anesthesia or respiratory assistance. In case of bleeding during major surgery the treatment includes replacement of missing or non-functional coagulation factors by commercial FP, FFP or cryoprecipitate. However, this may not be sufficient since the presence of tPA and plasminogen within the above products can mediate the fibrinolytic activity at the site of injury of surgery and thereby promote the dissolution of clot formed to stop or prevent the bleeding. Therefore, administration of the t-PA and plasminogen-deficient products of the invention that display significantly reduced fibrinolytic activity, is a better and more efficient therapeutic option that the commercial products, since in addition to supplementation of coagulation factors by the products of the invention their antifibrinolytic activity (as demonstrated by the Examples), may decrease or prevent bleeding contributed by the clot lysis induced by fibrinolytic proteins that are present in commercial products.

In particular embodiments the methods of the invention are applicable for open heart surgery. Some surgical procedures can be anticipated to cause severe bleeding, such as open heart surgery. In these operations extracorporeal circulation (cardiopulmonary bypass—CPB) is used.

Cardiovascular (open heart) surgery is surgery on the heart or great vessels performed by cardiac surgeons. Frequently, it is done to treat complications of ischemic heart disease (for example, coronary artery bypass grafting), correct congenital heart disease, or treat valvular heart disease from various causes including endocarditis, rheumatic heart disease and atherosclerosis. It also includes heart transplantation. During open-heart surgery, the heart is temporarily stopped. Patients undergoing an open-heart surgery are placed on cardiopulmonary bypass, meaning a machine which pumps their blood and oxygen for them. A machine will never function the same as a normal heart and lungs, therefore, similar to many surgical procedures, the time on this machine is kept to a minimum. This artificial method provides a bypass, to overcome temporarily a patient's needs with regard to the function of the heart and lungs.

The bleeding phenomena that occur in these operations are due to the anticoagulation used during the surgery, which, deliberately induces coagulation deficiency. In addition, platelet dysfunction that stems from the passing of the blood through an extracorporeal circulation contributes to the tendency to bleed.

It should be realized that the methods of the invention may be particularly applicable for subjects undergoing open heart surgery by CPB. The products, compositions and methods of the invention may impart dual beneficial effect to these patients as follows:

1. During the open heart surgery, blood will flow through a tube added to the heart-lung machine (CPB machine), while the tube is coated with tranexamic acid to deplete t-PA and/or plasminogen from the blood (as detailed in Experimental Procedures). The pump will direct the blood flow from the CPB machine to the patient. While flowing through this tube, the blood depleted in t-PA and plasminogen is returned to patient's circulation.

By this way the returned blood is poor in fibrinolytic activity and enriched in antifibrinolytic activity, thereby providing protection from bleeding tendency.

2. In case bleeding occurs due to the above mentioned reasons, the patient may then be treated to stop bleeding with t-PA-deficient and plasminogen-depleted blood or blood-derived products of the invention, which are expected to be more potent in cessation of bleeding due to their antifibrinolytic qualities (as also demonstrated in FIG. 7).

In further embodiments the methods of the invention are suitable for implementation in treatment of bleeding associated with liver transplantation surgery. The liver plays a central role in hemostasis and thrombosis. Liver parenchymal cells are the site of synthesis of most coagulation factors, the physiologic inhibitors of coagulation, and essential components of the fibrinolytic system. The liver also regulates hemostasis and fibrinolysis by clearing activated coagulation factors and enzyme inhibitor complexes from the circulation. Therefore, when liver dysfunction occurs in patients with liver disease, a complicated hemostatic derangement ensues, which can lead to bleeding.

During the first stage of liver transplantation, the removal of the diseased liver, (the anhepatic stage), significant hemostatic changes can occur. Because activated clotting factors are not removed from the circulation, their consumption can develop together with consumption of platelets and secondary hyperfibrinolysis. Moreover, primary hyperfibrinolysis also occurs as a result of defective clearance of tPA. The most severe hemostatic changes during liver transplantation occur after reperfusion of the donor liver. Platelets are trapped in the graft, giving rise to an aggravation of thrombocytopenia and causing damage to the graft by induction of endothelial cell apoptosis. Release of tissue factor and tPA from the reperfused graft further causes fibrinolysis. Thus, hyperfibrinolysis is thought to contribute significantly to impaired hemostasis during the anhepatic and reperfusion phases. Moreover, the graft releases heparin-like substances that can inhibit coagulation. In addition, other factors such as hypothermia, metabolic acidosis, and hemodilution adversely affect hemostasis during this phase. Liver transplantation is a lengthy procedure with extensive surgical wound surfaces including potential transaction of collateral veins. Improved surgical techniques and anesthesiologic care have led to a remarkable reduction of blood loss during liver transplantation. When uncontrolled bleeding occurs, packed red cells, platelets, and fresh-frozen plasma can be transfused. Use of synthetic antifibrinolytic agents, such as tranexamic acid (a lysine analogue) and aprotinin (a serine protease inhibitor) is a common practice.

Thus it should be appreciated that the products of the invention, compositions, and methods described by the invention, owing to their antifibrinolytic qualities may be particularly applicable for cessation of bleeding associated with hyperfibrinolytic state induced by liver transplantation surgery.

It should be appreciated that the methods of the invention may be applicable for any surgery involving any organ or tissue transplantation, for example, liver, kidney, lung, heart, pancreas, skin, blood vessels and the like.

In yet another embodiment, the products of the invention may be applicable for treating bleeding induced by fibrinolytic/thrombolytic therapy.

Fibrinolytic/thrombolytic therapy is mostly administered in patients with acute myocardial infarction (acute coronary artery thrombosis) or in patients with acute stroke (acute cerebral arterial thrombosis). The goal of fibrinolytic/thrombolytic therapy is rapid restoration of blood flow in an occluded vessel achieved by accelerating fibrinolytic proteolysis of the thrombus. Fibrinolytic therapy typically results in fibrinolytic state because plasminogen activation is not limited to the thrombus. These effects are complex and include a reduction in fibrinogen level, increase in fibrinogen degradation products, and decreases in coagulation factors. The complication of fibrinolytic therapy is bleeding. Bleeding complications are more frequent with fibrinolytic than with anticoagulant therapy and require rapid diagnosis and management. Two problems contribute to excess bleeding. First, the fibrinolytic effect is not limited to the site of thrombosis but is usually systemic. Therefore, any hemostatic plugs needed to prevent bleeding at sites of vascular injury caused either by catheters needed for treatment or within pathologic lesions in the brain, gastrointestinal tract, or elsewhere are also susceptible to dissolution. The most serious complication is intracranial hemorrhage which occurs in approximately 1% of patients and is associated with a high mortality and serious disability in survivors. The most common bleeding complications are related to invasive vascular procedures such as placement of arterial and venous catheters. Some bleeding at these sites is frequent and should not be a reason for interrupting therapy if it can be managed with local pressure or other simple measures. The problem can be minimized by limiting venous and arterial punctures and by early institution of local measures. Major bleeding may also result from preexisting lesions such as gastrointestinal ulcers or genitourinary lesions.

Treatment of bleeding complications following fibrinolysis/thrombolysis involves measures directed to the local site as well as correction of the systemic hypocoagulable state includes replacement therapy to correct the hemostatic defect caused by systemic plasminemia. Fibrinogen replacement is often needed and can be accomplished by administration of cryoprecipitate, and fresh-frozen plasma can be used to replace other hemostatic proteins.

It should be noted that fibrinolytic/thrombolytic therapy, involves the use of anti-coagulants or anti-coagulating agents. As used herein, the term "anticoagulant agent" is intended to mean any agent which interferes with the clotting of blood. Some anticoagulants, such as the coumarin derivatives bishydroxycoumarin (Dicumarol) and warfarin (Coumadin) inhibit synthesis of prothrombin, a clot-forming substance, and other clotting factors. Anticoagulants can include but are not limited to compounds acting as beta2 Adrenoreceptor Antagonists, Neuropeptide V2 Antagonists, prostacyclin analogs, thromboxane synthase inhibitors, calcium agonists, coumarin derivatives, elastase inhibitors, Non-steroidal anti-inflammatories thrombin inhibitors, lipoxygenase inhibitors, Factor Vila inhibitors, Factor Xa inhibitors, phosphodiesterase III inhibitors, Heparins, and fibrinogen glucoprotein IIb/IIIa Antagonists.

Coumarins are vitamin K antagonists. A prominent member of this class is warfarin (Coumadin). These anticoagulants are used to treat patients with deep-vein thrombosis (DVT), pulmonary embolism (PE) and to prevent emboli in patients with atrial fibrillation (AF), and mechanical prosthetic heart valves. Other examples are acenocoumarol, phenprocoumon, atromentin, and phenindione.

Heparin is a biological substance, usually made from pig intestines. It works by activating antithrombin III, which blocks thrombin from clotting blood. Low molecular weight heparin, a more highly processed product, is useful as it does not require monitoring of the APTT coagulation parameter and has fewer side effects as for example Enoxaparin (Clexane).

Fondaparinux is a synthetic sugar composed of the five sugars (pentasaccharide) in heparin that bind to antithrombin and is an inhibitor of factor Xa. It is a smaller molecule than low molecular weight heparin. Another example is Idraparinux sodium which has a similar chemical structure and method of action as fondaparinux.

Drugs such as rivaroxaban, apixaban and edoxaban work by inhibiting factor Xa directly (unlike the heparins and fondaparinux, which work via antithrombin activation). Further examples include but are not limited to betrixaban from Portola Pharmaceuticals, darexaban (YM150) from Astellas, and more recently letaxaban (TAK-442) from Takeda and eribaxaban (PD0348292) from Pfizer.

Another type of anticoagulant is the direct thrombin inhibitor. Current members of this class include but are not limited to the bivalent drugs hirudin, lepirudin, and bivalirudin; and the monovalent drugs argatroban and dabigatran.

The antithrombin protein itself is used as a protein therapeutic anticoagulant agent that can be purified from human plasma or produced recombinantly (for example, Atryn, which is produced in the milk of genetically modified goats).

As indicated above, anti-coagulants administration for example, heparin, is the standard antithrombotic therapy indicated for acute venous thrombosis, for prophylaxis of thrombosis in the post-surgical (especially orthopedic) and immobile patient, and for flushing of intravenous lines to maintain patency. However, due to their potency, heparin and LMWH suffer drawbacks. Uncontrolled bleeding as a result of the simple stresses of motion and accompanying contacts with physical objects or at surgical sites is the major complication. In addition, approximately 5% (range up to 30%) of patients treated with heparin, and about 2% of patients receiving unfractionated heparin (UFH), develop immune-mediated thrombocytopenia (HIT) which may be complicated by either bleeding (as a consequence of decreased platelet count) or by arterial and venous thrombosis due to intravascular platelet clumping. The products and methods of the invention may prevent such undesired effects of these anti-coagulating agents.

It should be further recognized that the method of treatment with the products and compositions of the invention, due to their antifibrinolytic effects (Examples 2 and 3), is particularly applicable for treating the bleeding manifestations induced by thrombolytic/fibrinolytic therapy. As have been already described herein, depletion of the fibrinolytic protein/s, tPA and plasminogen, from the products and compositions of the invention renders them an additional advantage over the commercial blood-derived products (FFP, cryoprecipitate) since they endow with additional antifibrinolytic qualities, and thereby provide further protection against dissolution of the clots.

In yet some further specific embodiments, the invention provides methods applicable for treating, prevention, prophylaxis amelioration, inhibition of any bleeding associated with DIC. More specifically, Disseminated intravascular coagulation (DIC) is a pathological process characterized by the widespread activation of the clotting cascade that results in the formation of blood clots in the small blood vessels throughout the body. This leads to compromised tissue blood flow and can ultimately lead to multiple organ damage. In addition, as the coagulation process consumes clotting factors and platelets, normal clotting is disrupted and severe bleeding can occur from various sites.

In yet some further embodiments, the invention provides methods applicable for treating, prevention, prophylaxis amelioration, inhibition of any bleeding associated with childbirth or pregnancies, for example, postpartum hemorrhage (PPH). Postpartum bleeding or postpartum hemorrhage (PPH) is often defined as the loss of more than 500 ml or 1,000 ml of blood within the first 24 hours following childbirth. Signs and symptoms may initially include: an increased heart rate, feeling faint upon standing, and an increased breath rate. The condition can occur up to six weeks following delivery. The most common cause is poor contraction of the uterus following childbirth, the fact that not all of the placenta was delivered, a tear of the uterus, or poor blood clotting. Causes of postpartum hemorrhage are uterine atony, trauma, retained placenta, and coagulopathy, commonly referred to as the "four Ts":

Tone: uterine atony is the inability of the uterus to contract and may lead to continuous bleeding. Retained placental tissue and infection may contribute to uterine atony. Uterine atony is the most common cause of postpartum hemorrhage.
Trauma: Injury to the birth canal which includes the uterus, cervix, vagina and the perineum which can happen even if the delivery is monitored properly. The bleeding is substantial as all these organs become more vascular during pregnancy.
Tissue: retention of tissue from the placenta or fetus may lead to bleeding.
Thrombin: a bleeding disorder occurs when there is a failure of clotting, such as with diseases known as coagulopathies.

It should be appreciated that in some embodiments, the tPA and/or plasminogen free product of the invention and any methods using the same, may be applicable for the treatment and prevention of PPH as discussed above.

In yet some further embodiments, the method of the invention may be also applicable for treating GPS. Goodpasture syndrome (GPS) is a rare autoimmune disease in which antibodies attack the basement membrane in lungs and kidneys, leading to bleeding from the lungs and kidney failure. The depletion of tPA and/or plasminogen in accordance with the invention, from any blood products that are regularly used for treating said patients may approve treatment.

In yet some further embodiments, the methods of the invention may be applicable for treating bleding caused by vessel rupture.

Still further, as noted herein above, the invention provides methods applicable for treating, prevention, prophylaxis amelioration, inhibition of any bleeding tendency using an extracorporeal apparatus.

In a specific embodiment the extracorporeal apparatus is a pheresis apparatus.

In this particular embodiment the pheresis apparatus is used as a mean to produce the t-PA-deficient and/or plasminogen-depleted products of the invention to be further used in the methods of the invention, the methods suitable for treating bleeds.

As detailed in Experimental Procedures, blood is shifted from the circulation of a subject to a gradient separating container. The whole blood or blood components are flowing through a tube coated either directly or indirectly (e.g., via at least one linker), with tranexamic acid or containing magnetic beads, or any other metallic beads, or any other matrix or solid support, coated with tranexamic acid that can be extracted by subjecting the container to magnetic field, to deplete t-PA and plasminogen, and the t-PA-deficient and/or plasminogen-depleted products are then returned to the circulation of the subject.

In further embodiments, the extracorporeal apparatus may be cardio-pulmonary bypass (CPB).

As described herein above, blood flows through a tranexamic acid-coated tube or containers containing magnetic beads coated with tranexamic acid that can be extracted by submitting the container to magnetic field added to CPB machine to deplete plasminogen (as detailed in Experimental Procedures), and the t-PA-deficient and plasminogen-depleted blood is returned to patient's circulation.

In this particular embodiment, the CPB apparatus is used as a mean to produce the t-PA-deficient and plasminogen-depleted products of the invention to be used in the methods of the invention, the methods suitable for treating bleeding disorders.

In yet some further embodiments, the t-PA-deficient and plasminogen-deficient or t-PA-deficient and/or plasminogen free products of the invention, specifically, the t-PA-deficient and plasminogen-free blood, plasma, FFP, PRP and cryoprecipitate provided by the invention may be useful as safe and advantageous product replacing plasma or platelet-rich plasma (that are not devoid of t-PA-deficient and plasminogen), conventionally used for treating specific pathologic conditions.

In some specific embodiments, intra-articular injection of plasma or platelet-rich plasma is used for treating patients with knee osteoarthritis (OA). It has been shown that PRP injection to the knee, results in significant clinical improvements (Meheux C J et al.). On the other hand, expression of plasminogen activators (PA) of the urokinase type that degrade a variety of extracellular matrix components such as collagens and aggrecan core protein is considered to be of special importance in the development of OA (Pap G et al.). Expression of stromelysin and urokinase type plasminogen activator protein in resection specimens and biopsies at different stages of osteoarthritis of the knee (Pap G. et al.). Therefore, injection of t-PA-free and plasminogen-free PRP would prevent deleterious effect and improve the outcome. Thus, in some embodiments, the t-PA-deficient and plasminogen-deficient or plasminogen free products of the invention, specifically, the t-PA-deficient and plasminogen-free blood, plasma, FFP, PRP and cryoprecipitate may be used for the treatment of osteoarthritis, specifically in knee OA.

The invention further provides a method for the treatment, prevention, prophylaxis, amelioration, inhibition of bleeding, hemostatic disorders and any bleeding or pathologic condition associated therewith in a subject in need thereof, the method comprising the step of topically administering to said subject a therapeutically effective amount of at least one blood and/or blood-derived product that may be tPA-deficient and/or devoid of plasminogen or plasmin activity or of any composition or biological glue or sealant comprising the same.

In certain embodiments the invention provides the method comprising the step of administering to the subject a therapeutically effective amount of a biological glue or sealant of the invention comprising a t-PA-deficient and plasminogen-deficient blood-derived product, wherein said product is at least one of t-PA-deficient and plasminogen-deficient PRP, t-PA-deficient and plasminogen-deficient FFP, and t-PA-deficient and plasminogen-deficient cryoprecipitate.

In further embodiments, the biological glue or sealant of the invention comprises at least one coagulation promoting factor such as fibrinogen and at least one fibrinogen cleaving enzyme or any other agent that directly or indirectly activates fibrinogen, and calcium, wherein each of said coagulation promoting agent is optionally provided within a separate compartment.

In yet further embodiments, at least one of plasmin inhibitors, plasminogen inhibitors and plasminogen activator inhibitors may include, but not limited to aprotinin, tranexamic acid and ε-aminocaproic acid (EACA) may be added to the biological glue of the invention.

The biological glue/sealant of the invention may be particularly suitable in some embodiments, for topical administration.

Thus, in certain specific embodiments, the t-PA-deficient and plasminogen-deficient product of the invention that is administered topically may be a biological (e.g., fibrin) glue or sealant for treating, preventing, inhibiting, reducing, eliminating, protecting or delaying the onset of bleeding or leak of blood or any other organ or tissue components from endogenous organs according to the methods of the invention.

In certain specific embodiments, the methods of the invention may be suitable for using biological glue or sealant in the treatment of bleeding or prevention of anticipated bleeding, bleeding tendency and risk of bleeding. In more specific embodiments, the method of the invention may be used in the prevention of anticipated bleeds in patients who are at high risk for bleeding.

In yet some particular and non-limiting embodiments, the invention further provides the methods using the biological glue/sealant of the invention in the topical treatment or prevention of bleeding associated with surgery, trauma and fibrinolytic or thrombolytic therapy.

In some further embodiments, the methods of the invention may be suitable for the topical use as a biological glue/sealant for the treatment, prophylaxis, amelioration, inhibition or delaying the onset of bleeding induced by a major or minor surgical operation.

In contrast to major surgery that, as detailed above herein, relates to any surgical procedure that involves anesthesia or respiratory assistance, minor surgery is a medical procedure involving an incision with instruments, performed to repair damage or arrest disease in a living body. Since minor surgery includes an incision or cutting, which is an act of penetrating or opening with a sharp edge of any part of a human body, in a subject with bleeding tendency this procedure may induce significant bleeding.

Thus, the methods of the invention are particularly applicable for topical use of the biological glue/sealant of the invention in the treatment, prophylaxis, amelioration, inhibition or delaying the onset of bleeding induced by major and minor surgical procedures.

In yet some other specific embodiments, the method of the invention enables topical use of the biological glue/sealant of the invention in the treatment, prophylaxis, amelioration, inhibition or delaying the onset of bleeding symptoms associated with oper heart surgery.

Still further, in some embodiments the method of the invention enables topical use of biological glue/sealant of the invention in the treatment, prophylaxis, amelioration, inhibition or delaying the onset of bleeding induced by liver transplantation surgery.

In some particular embodiments the method of the invention may be suitable for topical use of biological glue/sealant of the invention in the treatment, prophylaxis, amelioration, inhibition or delaying the onset of bleeding associated with surgical operation in a subject diagnosed with hereditary hemostatic disorder.

Surgical procedures can be anticipated to cause severe bleeding in patients with hereditary hemostatic disorders. These patients can bleed excessively during or following surgery. It should be appreciated that regarding patients with hereditary hemostatic disorders, in addition to the extent of the surgical trauma, the magnitude of the fibrinolytic activity at the surgical site must be considered. Thus, surgical procedures at sites that are rich in fibrinolytic activity such as oral, nasal pharyngeal cavities, as well as urogenital system, particularly a prostatic bed, may end up with excessive bleeding in patients with hereditary hemostatic disorders.

Thus, the methods of the invention that involve topical use of biological glue/sealant of the invention in the treatment, prophylaxis, amelioration, inhibition or delaying the onset of bleeding induced by surgery, especially in regions of increased fibrinolytic activity, are of particular value in patients with hereditary disorders. It should be understood that although the glue of the invention may be used for management of bleeding, it may be used also for connecting and binding tissues, or providing support or scaffold for example, connective tissues (e.g., muscle, tendon and the like). Such support may be applicable for example in tendon injuries or in hernia.

In view of their antifibrinolytic qualities, the topical biological glue/sealant products of the invention are more appropriate for the patients with hereditary hemostatic disorders undergoing surgical procedures, than commercial preparations lacking this quality.

In yet some certain embodiments, the method of the invention may be applicable for topical use as the biological glue/sealant of the invention in the treatment, prophylaxis, amelioration, inhibition or delaying the onset of bleeding in subject diagnosed with coagulation factor deficiency and undefined tendency to bleed.

In a specific embodiment, the method of the invention enables using a topical biological glue/sealant of the invention in the treatment, prophylaxis, amelioration, inhibition or delaying the onset of bleeding in subject diagnosed with factor XI deficiency.

In a more specific embodiment, the method of the invention enables using a topical biological glue/sealant of the invention in the treatment, prophylaxis, amelioration, inhibition or delaying the onset of bleeding in subject diagnosed with factor X deficiency.

In yet further embodiment, the method of the invention enables using a topical biological glue/sealant of the invention in the treatment, prophylaxis, amelioration, inhibition or delaying the onset of bleeding in subject diagnosed with factor VII deficiency.

In a particular embodiment, the method of the invention enables using a topical biological glue/sealant of the invention in the treatment, prophylaxis, amelioration, inhibition or delaying the onset of bleeding in subject diagnosed with factor V deficiency.

In a one embodiment, the method of the invention enables using a topical biological glue/sealant of the invention in the treatment, prophylaxis, amelioration, inhibition or delaying the onset of bleeding in subject diagnosed with factor II deficiency.

In another embodiment, the method of the invention enables using a topical biological glue/sealant of the invention in the treatment, prophylaxis, amelioration, inhibition or delaying the onset of bleeding in subject diagnosed with fibrinogen deficiency.

It should be noted that in some embodiments, the methods and tPA and/or plasminogen free products of the invention may not be used for patients suffering from tPA deficiency. In yet some further embodiments, the methods and tPA and/or plasminogen free products of the invention may not be used for patients suffering from hypofibrinolysis.

As indicated above, the invention provide methods for the treatment of bleeding, hemostatic disorders and any condition associate therewith. As used herein, "disease", "disorder", "condition" and the like, as they relate to a subject's health, are used interchangeably and have meanings ascribed to each and all of such terms.

It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder, condition or pathology causes a second disease, disorder, condition or pathology.

As noted above, the invention provides methods for treating disorders as specified above. The term "treatment" as used herein refers to the administering of a therapeutic amount of the composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above. The treatment may be undertaken when a hemostatic condition initially develops, or may be a continuous administration, for example by administration more than once per day, every 1 day to 7 days, every 7 day to 15 days, every 15 day to 30 days, every month to two months, every two months to 6 months, or even more, to achieve the above-listed therapeutic effects.

The term "prophylaxis" refers to prevention or reduction the risk of occurrence of the biological or medical event, specifically, the occurrence or re occurrence of disorders associated with bleeding, that is sought to be prevented in a tissue, a system, an animal or a human being, by a researcher, veterinarian, medical doctor or other clinician, and the term "prophylactically effective amount" is intended to mean that amount of a pharmaceutical composition that will achieve this goal. Thus, in particular embodiments, the methods of the invention are particularly effective in the prophylaxis, i.e., prevention of conditions associated with bleeding disorders. Thus, subjects administered with said compositions are less likely to experience symptoms associated with said bleeding disorders that are also less likely to re-occur in a subject who has already experienced them in the past.

The term "amelioration" as referred to herein, relates to a decrease in the symptoms, and improvement in a subject's condition brought about by the compositions and methods according to the invention, wherein said improvement may be manifested in the forms of inhibition of pathologic processes associated with the bleeding disorders described herein, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the invention described below.

The terms "delay", "delaying the onset", "retard" and all variations thereof are intended to encompass the slowing of the progress and/or exacerbation of a disorder associated with protein misfolding or protein aggregation, specifically, bleeding disorders and their symptoms slowing their progress, further exacerbation or development, so as to appear later than in the absence of the treatment according to the invention.

As noted above, treatment or prevention include the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process, specifically, a bleeding disorder by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

As indicated above, the method of the invention involves the administration of a therapeutically effective amount of the tPA-deficient blood and blood-derived product devoid of plasminogen or plasmin activity of the invention. The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the distribution profile within the body, a variety of pharmacological parameters such as half-life in the body, on undesired side effects, if any, on factors such as age and gender, etc.

More specifically, the products, compositions or kits comprising t-PA-deficient and/or plasminogen-deficient blood or t-PA-deficient and plasminogen-deficient plasma (frozen and fresh), t-PA-deficient and/or plasminogen-deficient cryoprecipitate or t-PA-deficient and/or plasminogen-deficient PRP provided by the invention, or any combination or mixture thereof may be administered for prophylactic and/or therapeutic treatments. In therapeutic application, compositions are administered to a patient already affected by a bleeding disorder or will manifest with bleeding symptoms in different situations that induce bleeding, specifically, in an amount sufficient to cure or at least partially arrest the bleeding and its complications. An amount adequate to accomplish this is defined as a "therapeutically effective dose." Amounts effective for this use will depend upon the severity of the condition and the general state of the patient, and may therefore include one or more units of blood or blood products in accordance with the invention. Thus, for blood transfusion purpose, the effective amount may depend on the patient's condition and may range between 1 to 20 and more blood units within 24 hrs, specifically, 1, 2, 3, 4, 5, 6, 7, 8, 9, 10, 11, 12, 13, 14, 15, 16, 17, 18, 19, 20 or more.

Single or multiple administrations on a daily, weekly or monthly schedule can be carried out with dose levels and pattern being selected by the treating physician. More specific embodiments relate to the use of typically 2-3 doses per week.

The present invention relates to the treatment of subjects, or patients, in need thereof. By "patient" or "subject in need" it is meant any organism who may be infected by the above-mentioned pathogens, and to whom the preventive and prophylactic products, kit/s and methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal.

More specifically, the tPA and/or plasminogen deficient products, composition/s, kit/s and method/s of the invention are intended for preventing pathologic condition in mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection (intra venous (IV), intra arterial (IA), intramuscular (IM) or sub cutan (SC)), drinking water, feed, spraying, oral lavage and directly into the digestive tract of subjects in need thereof.

Still further, the tPA and plasminogen deficient products, composition/s and kit/s of the invention and any components thereof may be applied as a single daily dose or multiple daily doses, preferably, every 1 to 7 days. It is specifically contemplated that such application may be carried out once, twice, thrice, four times, five times or six times daily, or may be performed once daily, once every 2 days, once every 3 days, once every 4 days, once every 5 days, once every 6 days, once every week, two weeks, three weeks, four weeks or even a month. The application of the tPA and plasminogen deficient products, composition/s and kit/s of the invention or of any component thereof may last up to a day, two days, three days, four days, five days, six days, a week, two weeks, three weeks, four weeks, a month, two months three months or even more. Specifically, application may last from one day to one month. Most specifically, application may last from one day to 7 days.

It should be appreciated that the method of the invention are not limited to any rout of administration. Specifically, the tPA and plasminogen deficient products, composition/s and kit/s may be administered either systemically, or locally, for example, topically. The phrases "systemic administration", "administered systemically" as used herein mean the administration of a compound, drug or other material (e.g., the tPA and plasminogen deficient products of the invention) other than directly into the central blood system, such that it enters the patient's system and, thus, is subject to metabolism and other like processes.

In a further aspect, the invention encompasses a blood and blood-derived product that may be tPA-deficient and/or devoid of plasminogen or plasmin activity or any composition or glue or sealant thereof, for use in the treatment, prevention prophylaxis, amelioration, inhibition or delaying the onset of bleeding, hemostatic disorders and any bleeding or pathologic condition associated therewith in a subject in need thereof. In some further embodiments, the product for use of the invention may be a t-PA-deficient blood or blood-derived product. In some other specific embodiments, the product for use of the invention may be devoid of plasminogen and/or plasmin activity. In yet some specific embodiments, the product for use of the invention may be a t-PA-deficient and devoid of plasminogen and/or plasmin activity. Still further, in some further embodiments, the product for use of the invention may be a t-PA-deficient blood or blood-derived product. In some other specific embodiments, the product for use of the invention may be a plasminogen-deficient blood or blood-derived product. In yet some specific embodiments, the product for use of the invention may be a t-PA-deficient and plasminogen-deficient blood or blood-derived product.

Thus, in further embodiments, the products of the invention may be relevant for use in the treatment of bleeding in a subject in need thereof. said it should be noted that the product/s of the invention comprise at least one coagulation factor and display reduced fibrinolytic activity.

In some specific embodiments, the t-PA-deficient and plasminogen-deficient blood or blood-derived product of the invention may be applicable for use in the treatment of bleeding, or any hemostatic disease or condition disclosed by the invention, in a subject in need thereof. In some embodiments, the products may comprise at least one coagulation factor and display reduced fibrinolytic activity.

In a certain embodiments, the t-PA-deficient and plasminogen-deficient blood or blood-derived product for use in accordance with the invention, may be at least one of t-PA-deficient and plasminogen-deficient whole blood, t-PA-deficient and plasminogen-deficient plasma, t-PA-deficient and plasminogen-deficient FFP, t-PA-deficient and plasminogen-deficient PRP and t-PA-deficient and plasminogen-deficient cryoprecipitate.

A specific embodiment of the invention comprises t-PA-deficient and plasminogen-deficient product that contains fibrinogen.

Yet in some further specific embodiment, the t-PA-deficient and plasminogen-deficient product for use according to the invention may further comprise at least one inhibitor of at least one of plasmin, plasminogen, and plasminogen activator or combination thereof.

In some specific embodiments, the product of the invention is applicable for parenteral use. In yet more specific embodiments, at least one inhibitor of fibrinolysis. Non-limiting examples may include, but are not limited to TLCK hydrochloride (TLCK), Camostat mesylate, Benzamidine HCl, α2-anti-plasmin, tPA-mutant, PAI-1, aprotonin, PPACK dihydrochloride, RG1192, biotinylated (tTA inhibitor), TAFI and lysine analogs like tranexamic acid may be added to the parenterally used product of the invention.

In further embodiments the product of the invention may be derived from autologous or allogeneic source (e.g., blood, blood products or plasma).

Still additional embodiments of the invention provide the blood-derived t-PA-deficient and plasminogen-deficient biological glue/sealant with reduced fibrinolytic activity for use in the treatment, prevention prophylaxis, amelioration, inhibition or delaying the onset of bleeding, hemostatic disorders and any bleeding or pathologic condition associated therewith in a subject in need thereof.

According to some embodiments, the tPA-deficient and plasminogen-deficient biologic glue/sealant of the invention may be at least one of t-PA-deficient and plasminogen-deficient FP or FFP, t-PA-deficient and plasminogen-deficient cryoprecipitate and t-PA-deficient and plasminogen-deficient PRP. In yet some further embodiments, the FP, FFP, cryoprecipitate and PRP may be derived from autologous human source or allogeneic human source (blood, plasma or blood product).

Still further, the biologic glue/sealant for use, in accordance with the invention may comprise at least one coagulation promoting factor such as fibrinogen and at least one fibrinogen cleaving enzyme and calcium. In some embodiments, the fibrinogen cleaving enzyme may be at least one of thrombin or reptilase or any other enzyme as discussed herein before in connection with other aspects of the invention.

In some specific embodiments, at least one inhibitor of at least one of plasmin, plasminogen and plasminogen activator may be added to the biologic glue/sealant for use in accordance with the invention. More specifically, such inhibitor may be at least one of aprotinin, tranexamic acid and ϵ-aminocaproic acid (EACA).

It should be appreciated that the biological glue/sealant of the invention for use in accordance with the invention may be adapted in some embodiments, for topical use.

In yet some further embodiments, the biological glue for you in accordance with the invention may be applicable for treating bleeding and hemostatic disorders in patients subject diagnosed with hereditary or acquired hemostatic disorder and having trauma- or surgery-induced bleeding. It is to be understood that any of the disorders or conditions disclosed above for other aspects of the invention, may be also applicable for the present aspect as well.

In some specific embodiments, the t-PA-deficient and/or plasminogen-deficient blood or blood-derived product for use according to the invention may be applicable for use in the treatment of bleeding or any pathologic condition associated therewith in a subject in need thereof. In more specific embodiments, the product comprises at least one coagulation factor and display reduced fibrinolytic activity.

In certain embodiments, the invention provides at least one of t-PA-deficient and/or plasminogen-deficient whole blood, t-PA-deficient and/or plasminogen-deficient plasma, t-PA-deficient and/or plasminogen-deficient FFP, t-PA-deficient and/or plasminogen-deficient PRP and t-PA-deficient and/or plasminogen-deficient cryoprecipitate, for use as discussed above.

A specific embodiment of the invention comprises t-PA-deficient and plasminogen-deficient product for use as discussed above that contains fibrinogen.

Yet further the specific embodiment of the invention provide t-PA-deficient and plasminogen-deficient product for use in accordance with the invention, wherein the product may further comprise at least one inhibitor of at least one of plasmin, plasminogen, and plasminogen activator or combination thereof.

In a specific embodiment, the product of the invention may be applicable for parenteral use. In yet more specific embodiments, at least one of inhibitors of fibrinolysis, α2-anti-plasmin, anti-trypsin, tPA-mutant and PAI-1 or lysine analogs like tranexamic acid, may be added to the parenterally used product of the invention.

In further embodiments the product of the invention may be derived from autologous or allogeneic source.

In still further embodiments, the t-PA-deficient and plasminogen-deficient blood-derived product for use in accordance with the invention, may be specifically suitable for treating bleeding associated with hereditary or acquired bleeding disorders. More specifically, hereditary hemostatic disorder may be a disorder resulting from at least one of deficiency in at least one coagulation factor and undefined tendency to bleeding. In yet some further embodiments, the said deficiency in at least one coagulation factor may be deficiency in at least one of factor XI, factor X, factor V, factor VII, factor II (prothrombin) and factor I (fibrinogen), as discussed herein before.

According to some further embodiments, the product of the invention may be used in the treatment of bleeding associated with acquired hemostatic disorder. In more specific embodiments, such acquired hemostatic disorder may be at least one of surgery-induced bleeding, trauma-induced bleeding, acute gastrointestinal bleeding, burns, hemorrhagic stroke and bleeding resulting from fibrinolytic or thrombolytic therapy.

In some specific embodiments, said surgery-induced bleeding is bleeding induced by a major or minor surgery. In more specific embodiments, major surgery may be an open heart surgery. In yet some other embodiments a major surgery may be liver transplantation surgery.

In yet some further particular embodiments, the product/s of the invention may be provided for use in the treatment of at least one of gastrointestinal bleeding, burns and hemorrhagic stroke.

In yet some further embodiments, the products of the invention may be particularly applicable for use in the treatment of lung injury associated with emphysema and COPD.

In some specific embodiments, the t-PA-deficient and/or plasminogen-deficient blood-derived product of the invention may be specifically suitable for use in the treatment of bleeding associated with hereditary or acquired bleeding disorders, wherein said product is adapted for parenteral administration.

In yet some other embodiments, the t-PA-deficient and/or plasminogen-deficient product of the invention may be provided for use in the treatment of acquired bleeding disorder. In such case, administration may be performed using an extracorporeal apparatus. More particularly, the extracorporeal apparatus may be an aphaeresis apparatus or cardio-pulmonary bypass (CPB).

In some specific embodiments, t-PA-deficient and/or plasminogen-deficient products of the invention that may be obtained by aphaeresis apparatus, as detailed herein above, may be particularly suitable for use in autologous or allogeneic donation.

In a yet further embodiment t-PA-deficient and/or plasminogen-deficient products of the invention obtained by cardio-pulmonary bypass (CPB), as detailed herein above, are particularly suitable for use in open heart surgery.

In a further aspect the invention encompasses the use of the t-PA-deficient and/or plasminogen-deficient blood-derived products or any composition or glue or sealant thereof in the preparation of a medicament for the treatment, prevention prophylaxis, amelioration, inhibition or delaying the onset of bleeding, hemostatic disorders and any bleeding or pathologic condition associated therewith in a subject in need thereof. Thus, in further embodiments, the products of the invention may be relevant preparation of a medicament for the treatment of bleeding in a subject in need thereof. In some embodiments, the products may comprise at least one coagulation factor and display reduced fibrinolytic activity. In some embodiments, the product may be adapted for topical use.

In a certain embodiment the invention provides the use of at least one of t-PA-deficient and/or plasminogen-deficient whole blood, t-PA-deficient and/or plasminogen-deficient plasma, t-PA-deficient and/or plasminogen-deficient FFP, t-PA-deficient and/or plasminogen-deficient PRP and t-PA-deficient and/or plasminogen-deficient cryoprecipitate, wherein said t-PA-deficient and plasminogen-deficient product comprises fibrinogen.

Yet further the specific embodiment of the invention provides the use of the tPA-deficient and plasminogen-deficient product of the invention that may further comprise at least one inhibitor of at least one of plasmin, plasminogen, and plasminogen activator or combination thereof.

Still further, additional embodiments of the invention provide the use of the blood-derived tPA-deficient and plasminogen-deficient biological glue/sealant having reduced fibrinolytic activity in the preparation of a medicament for the treatment, prevention prophylaxis, amelioration, inhibition or delaying the onset of bleeding, hemostatic disorders and any bleeding or pathologic condition associated therewith in a subject in need thereof.

According to some particular embodiments the t-PA-deficient and plasminogen-deficient blood derived product used by the invention may be biological glue/sealant. Such glue/sealant of the invention may comprise at least one of t-PA-deficient and plasminogen-deficient FP, t-PA-deficient and plasminogen-deficient FFP, t-PA-deficient and plasminogen-deficient cryoprecipitate and t-PA-deficient and plasminogen-deficient PRP. In yet some further embodiments, the FFP, cryoprecipitate and PRP may be derived from autologous human or allogeneic human source.

Still further, the biologic glue/sealant use by the invention may comprise at least one coagulation promoting factor such as fibrinogen and at least one fibrinogen cleaving enzyme and calcium. In some embodiments, the fibrinogen cleaving enzyme may be at least one of thrombin or reptilase.

In some specific embodiments, at least one inhibitor of at least one of plasmin, plasminogen and plasminogen activator may be added to the biologic glue/sealant used by the invention. More specifically, such inhibitor may be at least one of aprotinin, tranexamic acid and ϵ-aminocaproic acid (EACA).

Still additional embodiments of the invention provide the use of the blood-derived t-PA-deficient and/or plasminogen-deficient product or any composition or glue or sealant thereof in the preparation of a medicament for the treatment, prevention prophylaxis, amelioration, inhibition or delaying the onset of bleeding, hemostatic disorders and any bleeding or pathologic condition associated therewith in a subject in need thereof. In some embodiments, the product may comprise at least one coagulation factor. In yet some further embodiments, such product has reduced fibrinolytic activity. Still further, in some embodiments, the product of the invention may be administered topically, is a biological glue or sealant.

The invention relates to the use of the biological glue or sealant of the invention that comprises a t-PA-deficient and/or plasminogen-deficient blood-derived product, wherein said product is at least one of t-PA and plasminogen-deficient PRP, t-PA-deficient and plasminogen-deficient FFP, and t-PA-deficient and plasminogen-deficient cryoprecipitate, wherein said PRP, FFP and cryoprecipitate are of autologous human or allogeneic human source.

Still further, the biologic glue/sealant used by the invention may comprise at least one coagulation promoting factor such as fibrinogen and at least one fibrinogen cleaving enzyme and calcium. More specifically, the fibrinogen cleaving enzyme may be at least one of reptilase and thrombin.

In some specific embodiments, at least one inhibitor of at least one of plasmin, plasminogen and plasminogen activator may be added to the biological glue/sealant used by the invention. Such inhibitor may be at least one of aprotinin, tranexamic acid and leaminocaproic acid (EACA).

In still further embodiments, the glue or sealant of the invention may be used in the preparation of a medicament intended to stop or prevent bleeding associated with hereditary or acquired bleeding disorder. Specifically, such bleeding may be induced by trauma or surgery.

Still further, additional embodiments of the invention provide the use of the blood-derived t-PA-deficient and plasminogen-deficient biologic glue/sealant of the invention with reduced fibrinolytic activity in the preparation of a medicament for the treatment, prevention prophylaxis, amelioration, inhibition or delaying the onset of bleeding in a subject in need thereof and any bleeding or pathologic condition associated therewith.

It should be understood that a patient diagnosed with hemostatic disorder either hereditary or acquired is at particularly high risk for bleeding following any kind of trauma (as detailed herein above) and during or after any kind of surgery (minor or major surgery), particularly surgery performed at sites rich in fibrinolytic proteins.

Therefore, the biologic glue/sealant of the invention owing to its antifibrinolytic activity provides a better alternative than commercial glue preparations for treatment of trauma or surgery-induced bleeding especially at sites of increased fibrinolytic activity, as detailed herein above.

It should be appreciated that the invention provides the use of any of the products disclosed herein before in connection with other aspects of the invention, in any of the methods described herein for the treatment of any of the disorders disclosed by the invention in connection with other aspects of the invention.

In yet a further aspect, the invention provides a kit. In some embodiments, the kit of the invention may comprise: (i) at least one blood and blood-derived product that may be tPA-deficient and/or devoid of plasminogen or plasmin activity; and (ii) at least one coagulation promoting agent. In yet some further embodiments, the kit of the invention may comprise: (i) at least one of t-PA-deficient and/or plasminogen-deficient blood, t-PA-deficient and/or plasminogen-deficient PRP, t-PA-deficient and/or plasminogen-deficient FFP, and t-PA-deficient and/or plasminogen-deficient cryoprecipitate; and (ii) at least one coagulation promoting agent.

In more specific embodiments, the kit of the invention may comprise: (i) at least one of t-PA-deficient and plasminogen-deficient blood, t-PA-deficient and plasminogen-deficient PRP, t-PA-deficient and plasminogen-deficient FFP, and t-PA-deficient and plasminogen-deficient cryoprecipitate; and (ii) at least one coagulation promoting agent.

In certain embodiments, the coagulation promoting agent comprised within the kit of the invention may be at least one of fibrinogen, and at least one of fibrinogen cleaving enzymes. Specifically, the fibrinogen cleaving enzyme may be at least one of thrombin and reptilase. In some specific embodiments, the kit of the invention may further comprise calcium.

Optionally, each of said coagulation promoting agent may be provided in a separate compartment. This may facilitate the treatment of diseases and conditions with a combination of active ingredients that may be kept and optionally administered separately. The kit of the invention may further provides a convenient modular format of the different constituents of the compounds and related components required for treatment and allows the required flexibility in therapeutic procedures.

Still further, in some embodiments, the at least one of t-PA-deficient and plasminogen-deficient whole blood, t-PA-deficient and plasminogen-deficient plasma, p t-PA-deficient and plasminogen-deficient FFP, t-PA-deficient and plasminogen-deficient cryoprecipitate, t-PA-deficient and plasminogen-deficient PRP of the kit of the invention may further comprises fibrinogen.

According to some specific embodiments, the kit of the invention may be particularly suitable for parenteral use. In some embodiments when used parenterally, the kit of the invention may further comprise at least one inhibitor of at least one of plasmin, plasminogen and plasminogen activator. More specifically, such inhibitor may be at least one of, α2-anti-plasmin, tPA-mutant and PAI-1 or lysine analogs like tranexamic acid.

It should be appreciated that each one of the blood or blood-derived products of the kit of the invention may be derived from autologous human or allogeneic human source.

According to some embodiments, the kit of the invention is intended to achieve a therapeutic effect in a subject suffering from bleeding disorders associated with any of the hereditary or acquired tendency to bleed as described herein above. It should be further appreciated that the kit of the invention may be also used for preventing said bleeding in subjects having an increased risk for bleeding.

Achieving a therapeutic effect is meant for example, where the kit is intended for the treatment of a specific bleeding disorder, such as hereditary deficiencies in coagulation factors or any conditions associated with acquired disorders with tendency to bleed.

Thus, in some embodiments, the kit of the invention enables the use of the active ingredients in a method of treating, preventing, inhibiting, reducing, eliminating, protecting or delaying the onset of pathological conditions or disorders associated with bleeding tendency.

More specifically, the kit may further include container means for containing separate products, such as a divided bottle or a divided foil packet. However, the separate products may also be contained within a single, undivided container. Typically the kit includes directions for the administration of the separate components. As noted above, the kit form may be particularly advantageous when the separate components are preferably administered in different dosage forms (e.g., parenteral vs. topical), are administered at different dosage intervals, or when titration of the individual components of the combination is desired by the prescribing physician.

According to some embodiments, the kit of the invention is intended for achieving a therapeutic effect in a subject suffering from disorders associated with bleeding. Achieving a therapeutic effect is meant for example, where the kit is intended for the treatment of a specific disorder, such as bleeding or hereditary or acquired pathologic condition associated therewith in subject in need thereof. It should be further noted that the application of the kit of the invention or any component thereof, may form a complementary treatment regimen for subjects suffering from any of the pathological disorders or diseases as discussed above, specifically, those disclosed in connection with other aspects of the invention. Still further, in some embodiments, the invention further encompasses a kit that comprises any of the products disclosed by the invention in connection with other aspects of the invention.

It should be appreciated that the products of the invention, kits, biological glue or sealant and methods described by the invention, may be applicable for any form of bleeding disorder, specifically, any form of bleeding tendency disclosed herein.

A further aspect of the invention relates to a method for the preparation of at least one blood and blood-derived product that may be tPA-deficient and/or devoid of plasminogen or plasmin activity. More specifically, the method of the invention may comprise the step of subjecting whole blood or blood-derived product comprising at least one coagulation factor to affinity-depletion procedure specific for at least one of tPA and plasminogen. During this procedure, the t-PA-deficient and/or plasminogen-deficient blood-derived product is recovered. This product is devoid of plasminogen or plasmin activity and therefore displays reduced fibrinolytic activity.

Still further, in some embodiments the method for the preparation of at least one t-PA-deficient and/or plasminogen-deficient blood-derived product employs an affinity-based plasminogen and/or t-PA depletion procedure, wherein said blood-derived product is contacting at least one molecule that specifically binds plasminogen and/or t-PA.

It should be appreciated that in the method for the preparation of at least one t-PA-deficient and/or plasminogen-deficient blood-derived product employing an affinity-based t-PA and plasminogen depletion procedure, the molecule that specifically binds t-PA and/or plasminogen is covering a device, a container or a tube within an apparatus. In some particular embodiments, the apparatus may be an extracorporeal apparatus such as aphaeresis apparatus or cardio-pulmonary bypass (CPB) machine.

In yet some particular embodiments the molecule that specifically binds tPA and plasminogen and is covering a device, a container or a tube may be at least one of 4-(aminomethyl)-cyclo-hexane-carboxylic acid (tranexamic acid), or ε-amino caproic acid or lysine or anti plasminogen antibodies, or anti-tPA antibodies or any combinations thereof.

In some particular embodiments the molecule or agent that specifically binds at least one of tPA and plasminogen, may comprises tranexamic acid. Tranexamic acid (TXA) as used herein, is a medication used to treat or prevent excessive blood loss in major bleeding conditions. TXA, also known as Trans-4-(Aminomethyl)cyclohexanecarboxylic acid and Tranexamsaeure, has a molecular Weight of 157.213 g/mol and the formula of $C_8H_{15}NO_2$. Tranexamic acid is marketed in different counties and is known by the following commercial names, Lysteda, Cyklokapron, Cyclo-F, Femstrual, Transcam, Traxyl, Pause, Espercil, Nicolda, Exacyl, Kapron, Hemostan and Hexakapron. It should be noted that any commercially available preparation or TXA product may be used by the methods of the invention. In yet some further embodiments, any TXA may be used by the invention with the proviso that the TXA used by the invention does not recognize and binds only plasminogen and/or plasmin. Still further, any TXA may be used by the invention with the proviso that said TXA is not a TXA that does not deplete tPA. In yet some further embodiments, any TXA that recognizes and binds both tPA and plasminogen, may be used by the invention.

As noted above, for depleting at least one of tPA and plasminogen from blood and blood products, an agent that specifically binds at least one of tPA and plasminogen may be used by the method of the invention, for example, TXA. In some embodiments, to facilitate the separation and cleaning of the tPA and plasminogen from the products of the invention, the binding agent may be linked to a solid support. As used herein, "solid support", also referred to herein as "matrix", is defined as any surface to which molecules may be attached through either covalent or non-covalent bonds. Thus, useful solid supports include solid and semi-solid matrixes, such as aero gels and hydro gels, resins, beads, biochips (including thin film coated biochips), micro fluidic chip, a silicon chip, multi-well plates (also referred to as microtiter plates or microplates), membranes, tubes, containers, filters, conducting and no conducting metals, glass (including microscope slides) and magnetic supports. More specific examples of useful solid supports include silica gels, polymeric membranes, particles, derivative plastic films, glass beads, cotton, plastic beads, alumina gels, nylon, latex bead, magnetic bead, paramagnetic bead, super paramagnetic bead, starch and the like. This also includes, but is not limited to, microsphere particles such as Lumavidin™ Or LS-beads, magnetic beads, charged paper, Langmuir-Blodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces. Thus, in some specific embodiments, the tPA and plasminogen binding agent, specifically, TXA used by the methods of the invention may be linked to, coupled or cover magnetic beads, metallic beads, or any other particles that can be centrifuged, as well as any container, for example, tubes, vessel, syringe, or apparatus, thereby performing affinity-based tPA and/or plasminogen depletion from the blood products of the invention. It must be appreciated that in some embodiments, any solid support, matrixes or bead may be used for the methods of the invention with the proviso that the TXA, when linked (either directly or indirectly) to said solid support, matrix or bead, does not recognize and binds only plasminogen and/or plasmin. Still further, any solid support, matrix or bead, may be used with the proviso that TXA, when linked (either directly or indirectly) to said solid support, matrix or bead, TXA is not a TXA that does not deplete tPA. In yet some further embodiments, any solid support, matrix or bead that when linked to TXA, the TXA recognizes and binds both tPA and plasminogen, may be used by the invention.

In some specific embodiments, the methods of the invention may use but is not limited to magnetic beads or particle as the solid support for the tPA and plasminogen binding agent, specifically, TXA. Magnetic particles are a class of particle that can be manipulated using magnetic fields. Such particles commonly consist of two components, a core made of magnetic material, often iron, nickel and cobalt, and a chemical component that has functionality. The term "magnetic beads" and "magnetic particles" are used herein interchangeably and refer to any particle dispersible or suspendable in solution, which may be attracted or guided by application of a magnetic field. Non-limiting examples of magnetic particles include microspheres, conjugates, micelles, colloids, liposomes, aggregates or complexes of a ferromagnetic, paramagnetic or superparamagnetic material.

It should be appreciated that in certain embodiments, the solid support used by the methods of the invention may comprise magnetic particles of one type or more, specifically, 1, 2, 3, 4, 5, 6, 7, 8, 9, 10 or more. The magnetic particles used may vary in size, composition and coating. In some embodiments, magnetic particles used in the methods of the invention, specifically as a solid support for the tPA and/or plasminogen binding agent, may comprise a magnetic core with a biocompatible coating. The biocompatible coating may comprise a polymer, e.g., polystyrene, dextran, polyvinyl alcohol (PVA), polyethylenimine (PEI), silica, dextransulfate, starch, citric acid salt, PEG/Amine, and the like. In some embodiments any coating that may reduce, minimize or avoid any aggregation of the beads used by the invention, may be used for coating the beads.

In yet some specific embodiments, any magnetic particles of any size may be used by the methods of the invention. In yet some specific embodiments, magnetic beads having a diameter ranging between about 10 μm to 1000 μm, may be used by the methods of the invention, specifically, 100 μm to 1000 μm. Specifically, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm and 1000 μm. In yet some further specific embodiments, magnetic beads having a diameter of between about 400 μm-450 μm may be particularly useful for the methods of the invention.

In some specific embodiments, magnetic beads coated with polystyrene having a diameter of about 400 polystyrene to 450 polystyrene, may be used by the methods of the invention.

In some embodiments, the magnetic particles used by the methods of the invention may be conjugated, attached, linked, mixed with, encapsulated within, or encapsulating at least one agent that binds at least one of tPA and plasminogen, specifically, tranexamic acid (TXA). The term "conjugation" or "association" may be used interchangeably with the term "entrapped", "attachment", "linked", "embedded", "absorbed" and the like, and contemplates any manner by which the at least one agent that binds at least one of tPA and plasminogen, specifically, TXA is held by or the magnetic particles used by the present invention. This may include for example, physical, chemical or non-chemical attachment to the carrier. In some embodiments, chemical attachment may be via a linker.

The linker can be composed of any assembly of atoms, including oligomeric and polymeric chains, which functions to connect one or more of the magnetic beads to the tPA and plasminogen binding agent, specifically, TXA.

As described herein, the magnetics bead/s or any other solid support or matrix as discussed above, may be associated with the tranexamic acid. In some embodiments, the association between the magnetics bead and the tranexamic acid is via at least one chemical bond. In namely the magnetics bead and the tranexamic acid, may be held together via bonding such as covalent, ionic, hydrogen, van der Waals, coordination, etc.

As used herein, the term "association" or any lingual variation thereof refers to the chemical or physical force which holds the two entities together. Such force may be any type of chemical or physical bonding interaction known to a person skilled in the art. Non-limiting examples of such association interactions are covalent bonding, ionic bonding, coordination bonding, complexation, hydrogen bonding, van der Waals bonding, hydrophobicity-hydrophilicity interactions, etc. As described herein the association of the solid support or matrix, specifically, magnetics bead with the tranexamic acid is also referred to as coating of the solid support or matrix, specifically, the magnetic bead/s with the tranexamic acid. In some embodiments, the association is via covalent bonding. In some embodiments, the magnetic beads are covalently bound to the tranexamic acid.

The binding between the magnetic beads or any other solid support and the tranexamic acid may be via at least one linker. As used herein the term "activated magnetic beads" or "activated solid support or matrix", refer to magnetic beads or any other solid support or matrix which can be covalently bound to the tranexamic acid or to a linker. The activated beads are obtained by pre-coating the beads with a suitable material having an active moiety enabling the covalent binding. In other words, in order for the magnetic beads to covalent bind the tranexamic acid either directly or via at least one linker, the magnetic beads are pre-coated to include reactive groups enabling this covalent binding.

In some embodiments the magnetic beads may be activated for example by pre-coating with any coating material. Non-limiting examples of such material include for example, amino acid, protein, epoxy, tosyl, carboxylic acid, carboxylated polyvinyl alcohol. when referring to "pre-coating" it should be understood as a preliminary step which results in coating of the magnetic beads with an active material that in turn enables covalent binding of the beads with the tranexamic acid (i.e. directly) or via at least one linker. In some embodiments, the magnetic beads are pre-coated with an amino acid, peptide or any derivative thereof. Pre-coated magnetic beads may comprise for example as active groups, a primary amine (—NH2), carboxyl (—COOH), sulfhydryl (—SH) or carbonyl (—CHO). In some embodiments, the magnetic beads are pre-coated to include a moiety that may react with primary or secondary amino groups. In some other embodiments, the magnetic beads are coated with polylysine.

In some further embodiments, the tranexamic acid is covalently bound to the magnetic bead via the amino group of the tranexamic acid. In some embodiments, the magnetic bead are coated with an amino-acid like compounds that has a free carboxylic end which in turn binds to the amino group of the tranexamic acid or to the linker. In yet some further embodiments, the coating may present a free carboxylic group by performing a chemical reaction. In some other embodiments, the pre-coated magnetic bead bind via the carboxylic acid (carboxyl) to the amino group of the tranexamic acid.

In some embodiment, the pre-coated magnetic bead binds the tranexamic acid via a linker, preferably a bifunctional crosslinker. As used herein the term "crosslinker" refers to a reagent which contain two or more reactive ends capable of chemically attaching to specific functional groups (for example primary amines, carboxyl, sulfhydryls, etc.) on amino acids, peptides, proteins or other molecules.

As appreciated, the crosslinker may have different length depending on variety of experimental requirements. The length refers to the molecular span of a crosslinker, i.e., the distance between conjugated molecules. In some embodiments, the crosslinker is cleavable (i.e., whether the linkage can be reversed or broken when desired, for example, EDC). In some embodiments, the crosslinker is a zero-length crosslinker. In some embodiments, the crosslinker cause direct conjugation of without becoming part of the final crosslink covalent bond.

In some other embodiments, the crosslinker has a length of about 1° A to about 20° A. In some other embodiments, the crosslinker has a length smaller than 5° A. In some other embodiments, the crosslinker has a length of about 1° A to about 5° A. In some other embodiments, the crosslinker has a length of about 2° A to about 4° A. In some other embodiments, the crosslinker has a length of about 9° A to about 20° A. n some other embodiments, the crosslinker has a length of about 9° A to about 15° A The crosslinker may be a homobifunctional crosslinker or heterobifunctional crosslinker. Homobifunctional crosslinkers are reagents that have the same type of reactive group at either end. Amine crosslinkers (namely bind amine reactive groups) may be selected for example from glutaraldehyde, bis (imidoesters) or bis (succinimidylesters) (also known as NHS esters). According to some embodiments, homobifunctional crosslinkers such as but not limited to dimethyl pimelimidate (DMP) or Glutaraldehyde can bind to $NH_2$ groups (primary groups) on the magnetic bead and to $NH_2$ groups the tranexamic acid. Sulfhydryl crosslinkers may be selected for example from maleimides, or pyridyl-dithiols.

In some embodiments, the linker is a heterobifunctional crosslinker. Heterobifunctional crosslinkers are reagents that have different type of reactive group at either end for example but not limited to amine-to-sulfhydryl or amine-to-carboxyl.

Amine-to-Sulfhydryl crosslinkers may have NHS esters and maleimides at each end, or NHS esters and pyridyldithiols at each end. Examples of heterobifunctional crosslinkers that can bind amine and Sulfhydryl groups are selected from but not limited to N-Succinimidyl 3-[2-pyridyldithio]-propionate (SPDP), Succinimidyl-4-(N-maleimidomethyl)cyclohexane-1-carboxylate (SMCC), or Succinimidyl-4-(p-maleimidophenyl) butyrate (SMPB).

Amine-to-carboxyl crosslinkers may have carbodiimide. Such carbodiimide crosslinker that activates carboxyl groups for spontaneous reaction with primary amines. These crosslinkers may conjugate carboxyl groups (glutamate, aspartate, C-termini) to primary amines (lysine, N-termini) and N-hydroxysuccinimide (NHS). Examples of heterobifunctional crosslinkers that can bind amine and carboxyl groups are selected from but not limited to dicyclohexylcarbodiimide (DCC) and (1-ethyl-3-(3-dimethylaminopropyl)carbodiimide hydrochloride (EDC) 1-Ethyl-3-(3-Dimethylaminopropyl)carbodiimide, Hydrochloride (EDAC). These crosslinkers are used for the conjugation of carboxyl groups (glutamate, aspartate, C-termini) to primary amines (lysine, N-termini) and N-hydroxysuccinimide (NHS) for stable activation of carboxylates for amine-conjugation.

In some embodiments, the linker is an aromatic system. Non-limiting examples include benzoic acid or substituted benzoic acid, benzenesulfonyl chloride, benzaldehyde, chloromethyl-benzene.

In some specific embodiments, the linker used is (1-ethyl-3-(3-dimethylaminopropyl)carbodiimide hydrochloride (EDC) 1-Ethyl-3-(3-Dimethylaminopropyl)carbodiimide.

It must be appreciated that in some embodiments, any linker may be used for linking the TXA to the solid support, matrix or bead in accordance with the methods of the invention, with the proviso that the TXA-bound to the solid support via said linker does not recognize and binds only plasminogen and/or plasmin. In yet some further embodiments, any linker that presents TXA in a manner that it recognizes and binds both tPA and plasminogen, may be used by the invention.

In some particular and non-limiting embodiments, for depletion and removal of tPA and plasminogen from blood and blood products, the method of the invention may use Polystyrene magnetic beads having a diameter of about 400-450 μm bearing 0.7-1.2 m·moles/g of Tranexamic Acid. (TXA).

As indicated above, the present invention provides a method for the preparation of at least one of t-PA-deficient and/or plasminogen-deficient blood-derived product, wherein said blood-derived product is at least one of whole blood, plasma, fresh frozen plasma (FFP), platelet rich plasma (PRP) and cryoprecipitate.

It is to be understood that the invention further encompasses any product, specifically, blood and blood-derived product that may be tPA-deficient and/or devoid of plasminogen or plasmin activity, that has been prepared by any of the methods of the invention. In yet some further embodiments, the invention further encompasses any of the products disclosed herein that may be in some embodiments prepared by any of the methods of the invention.

Yet in a further aspect, the invention provides a method for performing an extracorporeal procedure in a subject in need thereof to prepare blood and blood-derived product that may be tPA-deficient and/or devoid of plasminogen or plasmin activity, specifically, of autologous source. More specifically, the method of the invention may comprise the step of transferring of the blood of said subject into an extracorporeal apparatus. The blood is then subjected to affinity depletion procedure specific for t-PA-deficient and plasminogen, wherein said depletion procedure is performed before, during or after blood is being transferred into and out-off said apparatus, thereby obtaining a t-PA-deficient and plasminogen-deficient blood or plasma of said subject; which is then returns to said subject.

In one embodiment of the invention, a method for performing an extracorporeal procedure in a subject in need thereof employs cardiopulmonary bypass machine (CPB), where an affinity-based plasminogen depletion procedure is performed. This procedure of the invention can be particularly applicable for a patient undergoing open heart surgery by CPB machine. As has been described herein above, CPB procedure can be associated with significant bleeding. Therefore, taking a preventive measure such as depleting plasminogen from the blood and thereby decreasing its fibrinolytic activity may substantially reduce bleeding tendency.

In another embodiment a method for performing an extracorporeal procedure in a subject in need thereof employs aphaeresis apparatus/machine. In this procedure the whole blood is transferred into an aphaeresis apparatus. The blood is then separated into components as detailed herein above and the separated plasma and platelets may further undergo affinity-based plasminogen depletion procedure. The generated t-PA-deficient and plasminogen-depleted plasma and platelets can be further used for an autologous or allogeneic donation.

In case of autologous donation before planned surgery, this procedure of the invention may enable to obtain a sufficient amount of t-PA-deficient and/or plasminogen-deficient blood product with a decreased fibrinolytic activity that is supposed to be more efficient than commercial products to prevent clot lysis and thereby control bleeding associated with surgery.

In yet some certain embodiments, a method for obtaining t-PA-deficient and plasminogen-deficient blood or blood product of the invention performed by an extracorporeal procedure in a subject in need thereof may employ CPB and aphaeresis. The procedure for producing tPA-deficient and plasminogen-deficient blood products of the invention comprises affinity-based depletion of tPA and plasminogen by contacting the blood with at least one molecule that specifically binds plasminogen.

In some further specific embodiments, the molecule that specifically binds (either directly or indirectly) tPA and plasminogen may be tranexamic acid, ϵ-aminocaproic acid lysine or other lysine analogs, such as 6-amino hyxanoic acid, anti-plasminogen antibodies and anti-tPA antibodies or any combinations thereof. It should be noted that a tPA and/or plasminogen binding agent useful in the method of the invention may bind either directly or non-directly, at least one of tPA and plasminogen, thereby facilitating depletion thereof from the treated blood, plasma or blood product/s of the invention.

In yet another aspect, the invention provides an extracorporeal apparatus for blood and blood product/s pheresis. The apparatus of the invention may comprise or coated, at least in part, by tranexamic acid that specifically binds at least one of tPA and/or plasminogen. It should be noted that in some embodiments, the apparatus of the invention may be used to prepare any of the products of the invention. Still further, the apparatus of the invention may be used in the treatment of any of the disclosed disorders. It should be noted that in some embodiments, the extracorporeal apparatus provided by the invention may generate blood or blood products with decreased fibrinolytic activity. In some embodiments, such products are t-PA-deficient and/or plasminogen-deficient that could returned to the patients. In case returned to the donor, the products are considered autologous. In yet some further embodiments, where the resulting blood products may be administered as an allogenic product to a recipient. Still further, Apheresis units as used herein, may in some embodiments, incorporate polyvinyl tubing that draws blood from the patient and moves it through centrifuges and/or filters that also contain Tranexamic acid linked to a solid support, for example, beads, to separate blood products. The blood is then returned to the patient via tubing or is collected in bags, often suspended from a pole, for donation or disposal. A display and control panel allow the operator to program the unit and view progress and/or alerts. Safety features include pressure sensors, ultrasonic air-bubble detectors, optical fluid-level detectors, and dry-heat fluid warmers. The warmers help prevent hypothermia caused by infusing low-temperature fluids. The unit may have wheels or it may be placed on a cart.

All scientific and technical terms used herein have meanings commonly used in the art unless otherwise specified. The definitions provided herein are to facilitate understanding of certain terms used frequently herein and are not meant to limit the scope of the present disclosure.

All definitions, as defined and used herein, should be understood to control over dictionary definitions, definitions in documents incorporated by reference, and/or ordinary meanings of the defined terms.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The indefinite articles "a" and "an," as used herein in the specification and in the claims, unless clearly indicated to the contrary, should be understood to mean "at least one." It must be noted that, as used in this specification and the appended claims, the singular forms "a", "an" and "the" include plural referents unless the content clearly dictates otherwise.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Throughout this specification and the Examples and claims which follow, unless the context requires otherwise, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures. More specifically, the terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988).

Standard organic synthesis protocols known in the art not specifically described herein are generally followed essentially as in Organic syntheses: Vol. 1-79, editors vary, J. Wiley, New York, (1941-2003); Gewert et al., Organic synthesis workbook, Wiley-VCH, Weinheim (2000); Smith & March, Advanced Organic Chemistry, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Vanderkerken K The 5T2MM murine model of multiple myeloma: maintenance and analysis [Methods Mol. Med. 113:191-205 (2005); Epstein J. The SCID-hu myeloma model. Methods Mol. Med. 113:183-90 (2005)].

Materials and Reagents

Polystyrene beads having a diameter of about 400-450 µm, purchased from Polysciences, Inc.

Tranexamic acid purchased from Tess Pharmaceuticals Co., Ltd., Sendi Biotechnology CO., Ltd.

EVICEL®—fibrin sealant, purchased from J&J.

Plasminogen Rmoval Gel, 28-4109-03, purchased from J&J.

Experimental Procedures

Preparation of Magnetic Beads Coated with Amino Acids

Amino acids binding to paramagnetic iron oxide nanoparticles were achieved by a coupling reaction between the amine group of the amino acid and the carboxylic groups of the nanoparticles using EDC as a coupling reagent. Briefly, 5 mg of magnetic nanoparticles (beads) were mixed with 2 ml of a solution (acetonitrile) containing 2.5 mg glutaric anhydride. After 2 hours, the magnetic beads were centrifuged and the supernatant was discarded, the pellets were washed with acetonitrile (twice), centrifuged and the supernatant was discarded. The pellet was re-suspended in 1.5 ml of phosphate-buffered saline containing lysine (Lys) (0.5 mg/ml), 6-Aminohexanoic acid, tranexamic acid (TXA) (0.5 mg/ml), or Alanine (ALA) (0.5 mg/ml), and 0.5 mg of EDC, and reacted with a constant stirring. The particles suspension was submitted to magnetic field and washed three times with phosphate-buffered saline (PBS). Centrifugation can also be used to precipitate the magnetic nanoparticles instead of magnetic field. Schematic illustration of the magnetic beads of the invention is disclosed in FIG. 1.

Preparation of Plasminogen and/or tPA Deficient Whole Blood (PDWB)

Whole human blood was collected into a collection bag containing citrate phosphate dextrose CPD anticoagulant using standard procedures. Whole blood deficient in plasminogen was prepared by mixing the whole blood with saline containing magnetics beads coated with tranexamic acid. The mixture was incubated for 10-30 min by gentle shaking. At the end of the incubation, the mixture was exposed to magnetic field to precipitate the beads and supernatant was collected for clinical use.

Preparation of Plasminogen and/or tPA Deficient, Platelet Rich Plasma (PDPRP)

Human blood was collected into a collection bag containing citrate phosphate dextrose CPD anticoagulant using standard procedures. Platelet rich plasma (PRP) was separated from the rest of the components by two centrifugations at 1000 g for 6 min each at room temperature. PRP was then used to generate PDPRP.

Removal of plasminogen from the PRP fraction was undertaken by transferring the PRP to sterile plastic bags containing magnetics beads coated with tranexamic acid in saline solution. The mixture was shaken gently for 10-30 min at room temperature. After the incubation, the beads were precipitated by exposure to a magnetic field and the supernatant was collected for clinical use.

Preparation of Plasminogen and/or tPA Deficient Plasma (PDP)

Human blood was collected by phlebotomy into a collection bag containing citrate phosphate dextrose CPD anticoagulant using standard procedures. Cellular components of the blood (including platelets) were removed by centrifugation for 15 minutes at 2,000×g. Plasma remained in the supernatant was then incubated with magnetics beads coated with tranexamic acid in saline solution to generate plasma depleted in plasminogen (PDP). The beads were precipitated by exposure to a magnetic field or by centrifugation for 5-15 minutes at 2,000×g. The PDP was maintained at 2-8° C.

while handling. If the plasma was not used immediately, it was frozen and stored (Fresh Frozen Plasma—FFP) according to standard protocols.

Preparation of Plasminogen and/or tPA Deficient Cryoprecipitate (PDCP)

FFP was produced as detailed above. Cryoprecipitate was prepared from FFP by thawing at 4° C. Cold-insoluble proteins were removed from the cryoprecipitate by centrifugation at 4000 (RPM) for 5 min.

The cryoprecipitate was mixed with normal saline containing magnetics beads coated with tranexamic acid. The mixture was shacked gently for 10-30 min. The beads were precipitated by exposure to a magnetic field or by centrifugation for 5-15 minutes at 2,000×g. The supernatant containing plasminogen deficient cryoprecipitate (PDCP) was collected for clinical use.

Depletion of Plasminogen and/or tPA from the Blood by Apheresis Apparatus

The procedure comprises a commercial apparatus for removal of blood from the circulation of an individual and returning it to the individual after separation into several components. The method is used for therapeutic or donation purposes. More specifically, the method may be used to obtain autologous tPA and/or plasminogen free blood or blood product, or alternatively, tPA and/or plasminogen free blood or blood product for allogeneic use in a recipient. Anti-coagulated blood is shifted from the circulation passing through a shunt system outside the body while the shunt system is connected to a gradient separating container. Blood cells are separated from the plasma by centrifugation within the container, and the blood cells beside platelets are returned to the circulation, while the plasma and platelets are treated by flowing through a tube coated with tranexamic acid to deplete plasminogen or through container that contains magnetic beads coated with tranexamic acid. In case of container that contains magnetic beads coated with tranexamic acid, the beads are extracted by submitting the container to magnetic field or using a filter that prevents their incorporation to the circulating plasma. The plasma flow continues, where the beads are extracted. The t-PA-deficient and/or plasminogen-depleted plasma and platelets are then kept for autologous or allogeneic donation. In some embodiments, the whole blood is passing without separation through a tube coated with tranexamic acid or through container that contains magnetic beads or any other matrix coated with tranexamic acid to deplete the tPA and/or plasminogen and then the plasminogen depleted blood is returned to the circulation. To increase the efficacy of the depleting systems, in case of coated tubes or magnetic beads, the tPA and/or plasminogen can be removed periodically from the tranexamic acid-coated tube or magnetic beads by washing with saline containing soluble tranexamic acid. By that, the systems will be regenerated and will be able to deplete more plasminogen. It should be noted that in some embodiments, some of the elements in the systems provided by the invention may be disposable (e.g., for a single use).

Plasminogen and/or tPA Removal During Extracorporeal Circulation

Cardiopulmonary bypass (CPB) is a device used in open heart surgery to support the body during the surgical procedure.

CPB machine is connected to the large vessels veins and arteries near the heart. CPB machine consists of three principle components, the pump, the oxygenator, and the reservoir. The three components of the heart-lung machine are connected to each other and to the patient by a series of tubes, placed in part by the surgical team.

During the open heart surgery, blood flows through a tube coated with TXA that is added to the heart-lung machine as in plasmapheresis method. While flowing through this tube, the blood is depleted in plasminogen and the depleted blood or plasma is then returned to the circulation. The tPA and/or plasminogen can be released from the tranexamic acid-coated tube by washing with saline containing soluble tranexamic acid. Alternatively, the blood could flow through container that contains magnetic beads coated with tranexamic acid. The magnetic beads coated with tranexamic acid are extracted from the blood by submitting the container to magnetic field or by the use of filter that prevents there incorporation to the blood or plasma returned to the circulation. The blood flow continue, where the beads are further extracted and released for further use.

The same modification can be incorporated to cell saver apparatus, a system designed for autologous blood recovery for use in procedures where medium- to high-volume blood loss occurs, such as trauma cases. With the ability to deliver moderate hematocrit and to help remove traces of undesirable components such as free hemoglobin.

The idea could also be used to designee a stand-alone apparatus to be used in clinical cases of blood loss or internal or external bleeding. Furthermore, the same standing alone system could be used to prepare blood or blood products depleted of plasminogen and/or tPA.

Clot Lysis Assay

Clot lysis assay was performed as previously reported (Higazi A A et al. (1998)). First, clots were generated by adding thrombin (0.4 NIH U/mL final concentration) to either blood, FFP or cryoprecipitate untreated or pretreated with magnetics beads coated with tranexamic acid. Then the lysis of plasma clots was measured by adding phosphate buffered saline (PBS) containing WT-tPA (10 nM) to the clot surface for 1 hour at 37° C. Clots were then washed with PBS, incubated overnight with 0.2% trypan blue, rinsed with PBS, and photographed. Photographs were scanned using a Hoefer GS 300 densitometer (Amersham Pharmacia Biotech, Piscataway, N.J.). Sizes of the lytic zones were calculated using the National Institutes of Health Image program and the extend of fibrinolysis was determined as previously reported (Higazi A A et al. Blood (1998)).

Clot Lysis Monitored by Thromboelastography (TEG)

Clots were prepared from whole human blood untreated or treated with magnetic beads coated with tranexamic acid or lysine by adding kaolin. Lysis of the clots was induced by WT-tPA (10 nM). The lysis observed following addition of PBS served as a control. Clot formation and clot lysis parameters were measured using a TEG 5000 Thromboelastograph as previously reported (Higazi N et al. (2015)).

Tail Bleeding Assay

The tail bleeding tendency method was used with slight modification from the previously described model (Pleines I et al.). In brief, 2 mm of the tail tip of anesthetized mice was amputated. Before the amputation the tails were immersed in saline at 37° C. for 10 minutes. The amputated tails were immersed in Eppendorf tubes containing 500 µl of human FFP treated or untreated with magnetic beads coated with ⅒ volume/volume of 9 FFP and 1 coated beads of each one of the following amino acids: lysine, 6-aminohexanoic acid (6AHA), tranexamic acid or alanine. At the end of the 30 min, the Eppendorf tubes were collected. For dissolution of the blood clots formed in the FFP, tPA was added (100 nM) for 60 min at 37° C. The hemoglobin concentration reflecting the amount of bleeding was determined as previously reported (Higazi N. et al. (2015)).

Internal Bleeding Rat Model

Adult male, 8- to 10-wk-old Sprague-Dawley rats (average weight 250-280 g) were anesthetized with an intraperitoneal injection of ketamine (75 mg/ml) and xylazine (5 mg/ml) before the experiments. After shaving and cleaning, the abdomen was entered to respect the inferior edge of the left liver lobe as described in (World J Gastroenterol. Jan. 7, 2008; 4: 81-84).

Example 1 t-PA and Plasminogen Depleted Blood Products Prevents Fibrinolysis

Figure 1:
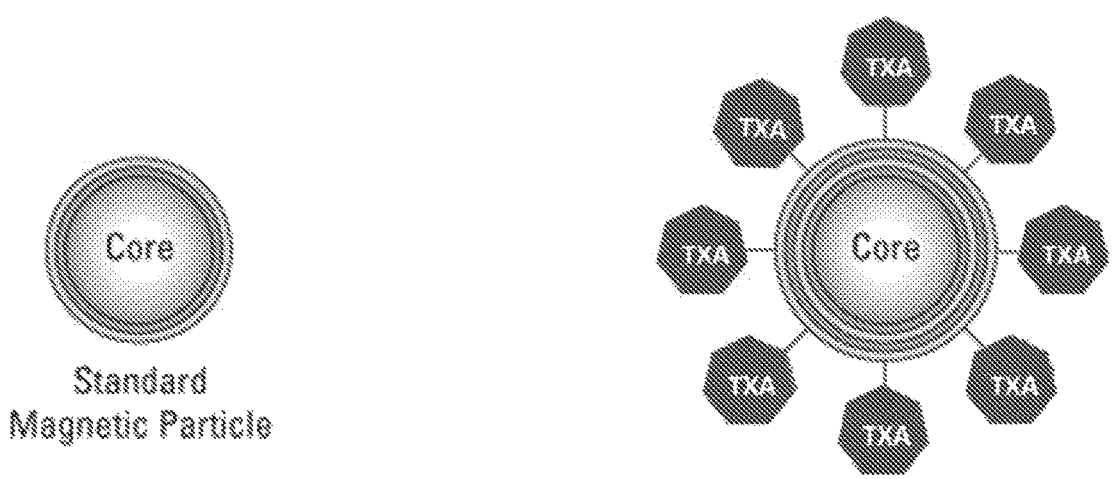
FIG. 1. Tranexamic acid magnetic beads

As mentioned herein before, the concept of the inventors was to prove that a depletion of fibrinolytic proteins, i.e. plasminogen and t-PA, from plasma products will increase their pro-coagulant properties. Hence, the inventors employed an affinity-based approach for depletion of plasminogen and t-PA from plasma products (whole blood, FFP and cryoprecipitate) to produce blood products with an inhibited and markedly reduced fibrinolytic activity. TXA, a synthetic derivative of the amino acid lysine, is capable of binding plasminogen molecules with high affinity and prevent their activation. Using a cross-linking approach, the inventors have demonstrated the generation TXA-conjugated magnetic beads as illustrated in FIG. 1.

FIG. 2 illustrates that plasma treated with magnetic beads carrying lysine or its analogs 6AHA or TXA is resistant to fibrinolysis. The data also show that the obtained antifibrinolytic effect is specific to lysine-mediated depletion of plasminogen and t-PA, since alanine-treated plasma failed to exhibit an inhibition of fibrinolysis. Furthermore, the data also indicate that TXA is significantly more potent in depleting the plasminogen from the plasma than lysine or 6AHA.

In line with these findings pretreating of another human blood product, cryoprecipitate, with magnetic beads coated with lysine analog (TXA) resulted in inhibition of fibrinolysis (FIG. 3).

The data presented in FIG. 3 also indicate that clots formed from untreated or alanine-treated cryoprecipitate can be easily dissolved by externally added tPA indicating that these clots are prone to fibrinolysis. Similar to the results obtained in FIG. 2, the findings shown in FIG. 3 reveals that the obtained antifibrinolytic effect is specific to lysine analog TXA.

Similarly to the results shown in previous Figures, the findings shown in FIG. 4 provide an additional support for the concept of the invention that pretreating of human blood with magnetic beads coated with lysine or lysine analogs inhibits fibrinolysis. The data presented in FIG. 4 indicate that depletion of plasminogen using magnetic beads coated with TXA rendered blood clots that are resistant to fibrinolysis. As in FIGS. 2 and 3, the data in FIG. 4 also show that the effect is specific to lysine analog, since no inhibitory effect was observed with blood treated with alanine.

Example 2

Use of Thromboelastography (TEG) to Demonstrate the Inhibition of Lysis of Clot Derived from Blood Products Deficient in Plasminogen and t-PA Thromboelastography has become a well-established monitoring device for hemostasis and transfusion management in major surgery, trauma, and bleeding disorders. Thromboelastography is performed in whole blood and assesses the viscoelastic property of clot formation under low shear condition. Thromboelastography provides clot formation and clot lysis variables that are different in clinical situation, and therefore could be used for diagnosis and treatment of bleeding disorders. Thus, the inventors have used this method to unambiguously show that a depleting of plasminogen and t-PA from human blood by pretreating it with magnetic beads coated with lysine or tranexamic acid resulted in inhibition of clot lysis (FIG. 5).

In contrast, lysis of clots prepared from untreated human blood is not inhibited. Thus, as in the previous Figures, the data in FIG. 5 indicate that depletion of plasminogen and t-PA using magnetic beads coated with lysine or TXA rendered blood clots that are resistance to fibrinolysis. The R value, in the TEG experiments, represents the time until the first evidence of a clot is detected. FIG. 5 also shows that the time until the first evidence of a clot formation is detected (as represented by shorter R value), is shorter in blood treated with magnetic beads coated with TXA. Such data indicate that treating the blood with magnetic beads coated with TXA stimulates the coagulation process. As in the previous figures, the data in FIG. 5 indicate that depletion of plasminogen and t-PA using magnetic beads coated with lysine or TXA rendered blood clots that are resistant to fibrinolysis.

This pro-coagulant effect of TXA-treated blood is further emphasized in FIG. 6. FIG. 6A shows that the R value in untreated blood is 4.2 min, while in blood pretreated with magnetic beads coated with TXA, the R is significantly shorter, 1.8 min (FIG. 6B), indicating that the time until the first evidence of a clot formation is decreased. To exclude the possibility that the decrease in R value seen in FIG. 6B is due to decreased fibrinolysis, the inventors determined the R value in presence of an initiator of fibrinolysis (FIG. 6C). Besides increasing fibrinolysis, presence of tPA contributes to plasminogen depletion, by converting plasminogen into plasmin. FIG. 6C shows that in spite of the increased fibrinolysis seen in presence of tPA, the R value is 2.8 min, indicating that the R value is not affected by fibrinolysis in this case. Taken together, the outcomes seen in blood pretreated with magnetic beads coated with TXA clearly demonstrate the feasibility of the product of the invention in reducing clot lysis.

Example 3

Depletion of Plasminogen and t-PA from Human Plasma Inhibits Bleeding Tendency Induced by Tail Tip Amputation in Mice Model Replacement therapy is a mainstay of treatment for bleeding disorders. However, replacing coagulation factors by FFP may not be sufficient to stop bleeding owing to the presence of fibrinolytic activity in FFP. Thus, the concept of the present invention is that providing a replacement by FFP with pro-coagulant activity but deficient in fibrinolytic activity is more beneficial in situations of bleeding.

Using a tail tip model in mice (FIG. 7), the inventors showed that immersion of cut tail in FFP significantly increased the amount of bleeding compared to saline. This finding excludes the possibility that dilution of coagulation factors is responsible for the excessive bleeding and suggests that FFP pro-coagulant effect is not sufficient to stop bleeding, probably due to its counteracting fibrinolytic activity. To prove the concept that a fibrinolytic activity present in FFP is responsible for the insufficient cessation of bleeding the amputated tails were immersed in FFP previously treated with magnetic beads coated with either lysine (Lys), 6-Aminohexanoic-Acid (6AHA), tranexamic acid (TXA) or alanine (Ala). The results as illustrated in FIG. 7, clearly indicate that only FFP depleted in plasminogen and t-PA by treatment with magnetic beads coated with lysine, 6AHA or TXA significantly reduced the amount of bleeding as compared to untreated or alanine-treated FFP.

Example 4

Transfusion of Mouse with t-PA and Plasminogen-Depleted Plasma Reduces Excessive Bleeding Plasma was collected form C57black mice, following the plasma was transferred through TXA-coated magnetic beads. C57black male mice were intravenous injected with 50 µl of: PBS (control), normal plasma and treated plasma, then the tip of the tail of those mice was cut and the mice were allowed to bleed for 30 min. As can be seen in FIG. 8 normal plasma failed to reduce the amount of blood the mice lost in compare to PBS treated mice. In contrast, t-PA and Plasminogen-depleted Plasma reduces the bleeding in more than 40%. This experiment establishes the feasibility of using the product of the invention systemically (i.v.) for the treatment of hemostatic disorders.

Example 5

Depletion of tPA from Blood and Plasma Components Treated with Magnetic Beads Coated with Lysine Analogs (TXA)

The effect of adding exogenous tPA to clots formed from plasma treated with magnetic beads coated with lysine analogs (TXA) or clots formed from a commercially available product (EVICEL® Fibrin Sealant, Ethicon, corresponding product of U.S. Pat. No. 7,125,569) was analyzed.

Figure 9:
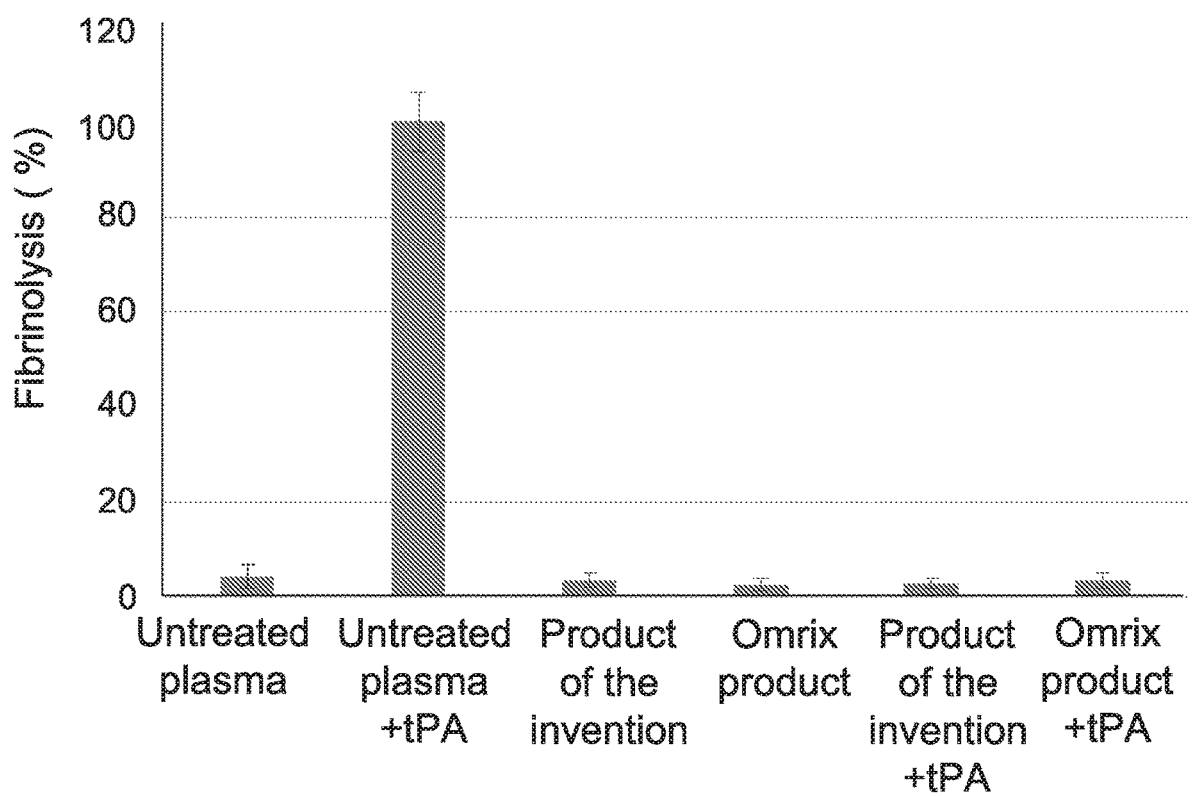

Clots were formed by adding thrombin as previously reported (Higazi A A et al. 1998). Then tPA (10 nM) was added and the lysis of plasma clots was measured as a percent of fibrinolysis relative to that of plasma in absence of tPA. FIG. 9 shows that external addition of tPA to both products induced very poor fibrinolysis compared to untreated plasma indicating that both products are plasminogen deficient.

Following, the effect of adding exogenous plasminogen to clots formed form plasma treated with magnetic beads coated with TXA or clots formed from the same commercially available product as above (EVICEL®), was examined.

The clots were formed also by adding thrombin. Plasminogen (3 µM) was added to the clots and fibrinolysis was evaluated as described above. FIG. 10 shows that adding plasminogen to clots from plasma treated with magnetic beads coated with TXA in accordance with the invention, resulted in no significant fibrinolytic effect. In contrast, adding plasminogen to clots from the commercial product resulted in dramatic increase in fibrinolysis. These results clearly indicate that the plasma treated with magnetic beads coated with TXA is deficient with tPA, in contrast the commercial product contains significant amount of tPA, that may lead to fibrinolysis.

Furthermore, the concentration of tPA in both products was determined directly using a commercial ELISA kit (Technozym, Vienna, Austria). FIG. 11 shows that the commercial product contains 1.5 ng/ml of tPA compared to 0.013 ng/ml found in the plasma treated with magnetic beads coated with TXA. It should be noted that the concentration of tPA in EVICEL® was significantly higher than in blood, plasma or serum (FIG. 11).

To further analyze the ability of the matrix of the invention (TXA-magnetic beads) to elute tPA from solutions (e.g., blood and blood products), as compared to a commercially available matrix coated with TXA [TEA-Sepharose 4B, Omrix, Plasminogen removal gel (28-4109-03, J & J)], both products were compared by their ability to bind tPA present in a solution. More specifically, magnetic beads coated with TXA (the matrix of the invention), as well as TEA-Sepharose 4B (Omrix), both, in an amount equivalent to the amount sufficient to clean 1 cc of human plasma from plasminogen (100 µl), were incubated with commercially available tPA (Boehringer Ingelheim) in PBS (0.1 mg/ml) for 15 min at room temperature. Before incubation with tPA, both preparations were washed 3 times with PBS. To remove the unbound tPA, both incubated matrixes were washed 3 times with PBS [1 ml each wash, followed by centrifugation (5000 RPM for 5 min)]. After the third wash, each resulting preparation was re-suspended in 1 ml of PBS and 25 µl of each was used for western blot. Commercially available monoclonal anti-tPA antibodies [anti-TPA Tissue Plasminogen Activator antibody [T-1] (ab82249), diluted 1:1,000] were used as first antibodies. Polyclonal Goat Anti-Mouse Immunoglobulins horseradish peroxidase (DAKO) was used as a secondary antibody for enhanced chemiluminescence reaction.

FIG. 12 clearly shows that in contrast to the TXA-magnetic beads of the invention that bound tPA, the amount of tPA bound to TEA-Sepharose 4B, Omrix matrix was undetectable. These results support the specificity of the TEA-Sepharose 4B, Omrix to plasminogen only, as declared for example in U.S. Pat. No. 7,125,569. Moreover, these results clearly demonstrate the effective ability of the matrix of the invention (e.g., TXA magnetic beads) to deplete tPA from any solution (e.g. blood or any blood product).

Example 6

Effect of Plasminogen and tPA Free Plasma on Internal Bleeding

Encouraged by the in vitro comparative data that establish the superiority of the tPA deficient product of the invention over the prior art products, the inventors next examined the effect of both products on in vivo internal bleeding rat model as described in experimental procedures. Briefly, 40 adult male, 8- to 10-wk-old Sprague-Dawley rats with resected inferior edge of the left liver lobe were divided into the following four groups (10 rats in each):

Group 1: Fibrin sealant (EVICEL®) group consisting of 10 rats.

The liver surface was coated with fibrin sealant (EVICEL®, Omrix, Israel), containing a mix human fibrinogen (1 ml) and human thrombin. The fibrin seal was applied using EVICEL® L application device and according to the instructions of the manufacturer.

Group 2: Untreated plasma group.

The liver surface was coated as in the previous group with one change; the 1 ml of human fibrinogen was substituted by 1 ml of human plasma.

Group 3: Plasminogen and tPA free plasma product of the invention. The liver surface was coated as in the previous groups with one change; the 1 ml of human fibrinogen was substituted by 1 ml of human plasma that was treated with beads coated with tranexamic acid.

Group 4: Untreated group.

Bleeding time was determined in all groups as described in (World J Gastroenterol. Jan. 7, 2008; 14: 81-84).

More specifically, bleeding time was 145.3±37.2 seconds in the untreated group. In the rats treated with fibrin sealant (EVICEL®) the bleeding time was 92.41±41.9 seconds. In rats treated with untreated plasma, the bleeding time was 206.73±64.2. However, in rats treated with the treated plasma of the invention, the bleeding time was 41.82±29.2 seconds. These results show a clear advantage and superiority of the product of the invention and its applicability in topical application of internal bleeding.

The invention claimed is:

1. A blood and/or blood-derived product that has a reduced fibrinolytic activity, said product comprising at least one coagulation factor, wherein said product is blood or a blood-derived product that has been treated so as to be tissue plasminogen activator (tPA)-deficient and at least one of plasminogen-deficient and devoid of plasminogen or plasmin activity, wherein said product has decreased R-value in thromboelastography (TEG) analysis, as compared to the untreated blood or blood-derived product.

2. The product according to claim 1, wherein said blood and/or blood-derived product is at least one of whole blood, plasma, fresh frozen plasma (FFP), platelet rich plasma (PRP) and cryoprecipitate.

3. The product according to claim 2, wherein said blood, plasma or any blood product is of autologous or allogeneic source.

4. A composition comprising at least one blood and/or blood-derived product as defined in claim 1, said composition further comprising at least one of pharmaceutically acceptable carriers, excipients, additives, diluents and adjuvants.

5. The composition according to claim 4, wherein said composition is further supplemented with fibrinogen and/or any other coagulation factor.

6. A biological glue or sealant comprising a blood and/or blood-derived product, as defined in claim 1, and
   at least one coagulation promoting agent being at least one of fibrinogen, thrombin or any fibrinogen cleaving enzyme, and calcium, wherein each said coagulation promoting agent is provided within a separate compartment.

7. The biological glue or sealant of claim 6, further comprising at least one inhibitor of at least one of plasmin, plasminogen and plasminogen activator.

8. A method for the treatment, amelioration, or inhibition of bleeding in a subject having a hemostatic disorder or any bleeding or pathologic condition associated therewith, the method comprising administering to said subject a therapeutically effective amount of at least one blood and/or blood-derived product in accordance with claim 1, or of any composition or biological glue or sealant comprising the same.

9. The method according to claim 8, wherein said product further comprises at least one inhibitor of at least one of plasmin, plasminogen and plasminogen activator.

10. The method according to claim 9, wherein said product is a biological glue or sealant containing said product, said biological glue or sealant further comprising at least one coagulation promoting agent being at least one of fibrinogen, thrombin or any fibrinogen cleaving enzyme, and calcium, wherein each of said coagulation promoting agent is provided within a separate compartment.

11. The method according to claim 10, further comprising at least one inhibitor of at least one of plasmin, plasminogen and plasminogen activator.

12. The method according to claim 8, wherein said product is a tPA-deficient and plasminogen-deficient blood-derived product and is administered parenterally.

13. The method according to claim 12, wherein said hemostatic disorder is hereditary or acquired bleeding disorder.

14. The method according to claim 13, wherein said hereditary hemostatic disorder is a disorder resulting from at least one of deficiency in at least one coagulation factor and undefined tendency to bleeding.

15. The method according to claim 14, wherein said deficiency in at least one coagulation factor is deficiency in at least one of factor XI, factor X, factor V, factor VII, factor II (prothrombin) and factor I (fibrinogen).

16. The method according to claim 13, wherein said acquired hemostatic disorder is at least one of surgery-induced bleeding, trauma-induced bleeding, acute gastrointestinal bleeding, bleeding associated with burns, hemorrhagic stroke, lung injury due to emphysema and Chronic Obstructive Pulmonary Disease (COPD), bleeding associated with childbirth and bleeding resulting from fibrinolytic or thrombolytic therapy.

17. The method of claim 16, wherein said acquired hemostatic disorder is bleeding induced by open heart surgery or a liver transplantation surgery.

18. The method according to claim 13, wherein said acquired hemostatic disorder is bleeding resulting from fibrinolytic or thrombolytic therapy.

19. The method according to claim 16, wherein said administration is performed using an extracorporeal apparatus.

20. The method according to claim 8, wherein said product is a biological glue or sealant comprising said tPA-deficient and plasminogen-deficient blood and/or blood-derived product adapted for topical administration.

21. The method according to claim 20, wherein said glue or sealant is administered to a subject suffering from at least one of bleeding, bleeding tendency and increased risk for bleeding, wherein said bleeding or increased risk for bleeding is at least one of surgery-induced bleeding, trauma-induced bleeding, and bleeding resulting from fibrinolytic or thrombolytic therapy.

22. The method according to claim 21, wherein said bleeding or increased risk for bleeding is bleeding induced by a major or minor surgical operation.

23. A kit comprising at least one blood and/or blood-derived product, as defined in claim 1, and at least one coagulation promoting agent.

24. The kit according to claim 23, wherein said coagulation promoting agent is at least one of fibrinogen, thrombin and calcium.

25. The kit according to claim 23, comprising more than one said coagulation promoting agent and wherein each said coagulation promoting agent is provided within a separate compartment.

26. The blood and/or blood-derived product according to claim 1, wherein said product is prepared by a method comprising:
   (i) subjecting whole blood or blood-derived product comprising at least one coagulation factor to affinity-depletion procedure specific for t-PA and plasminogen, wherein said affinity-depletion procedure uses a molecule that specifically binds tPA and plasminogen; and (ii) recovering the t-PA-deficient and/or plasminogen-deficient blood-derived product obtained in step (i).

27. The blood and/or blood-derived product according to claim 26, wherein the molecule that specifically binds tPA and plasminogen is at least one of 4-(aminomethyl)-cyclo-hexane-carboxylic acid (tranexamic acid), ε-amino caproic acid, lysine, anti-plasminogen antibodies and anti-tPA antibodies.

28. A method for performing an extracorporeal procedure in a subject in need thereof, the method comprising the steps of:
   (i) transferring blood of said subject into an extracorporeal apparatus;
   (ii) subjecting said blood to affinity depletion procedure specific for tPA and plasminogen, wherein said depletion is performed before, during or after blood is transferred into and out-off said apparatus, thereby obtaining an extracorporeal tPA-deficient and plasminogen deficient blood and/or blood-derived product of said subject; and
   (iii) returning the t-PA and plasminogen-deficient blood or plasma obtained in step (ii) to said subject.

29. The method according to claim 28, wherein the extracorporeal apparatus is a cardiopulmonary bypass machine (CPB), and wherein the extracorporeal apparatus is a plasmapheresis machine.

30. The method according claim 28, wherein said affinity depletion procedure of tPA and plasminogen is performed by contacting said blood with at least one molecule that specifically binds at least one of tPA and/or plasminogen.

31. The method according to claim 30, wherein said molecule that specifically binds at least one of tPA and plasminogen is at least one of tranexamic acid, lysine, 6-amino hyxanoic acid and any lysine analog.

32. The blood and/or blood-derived product, as defined in claim 1, wherein said product is adapted for topical administration as a biological glue or sealant.

33. A method for producing a blood and/or blood-derived product in accordance with claim 1, comprising:
   (i) subjecting whole blood or blood-derived product comprising at least one coagulation factor to affinity-depletion procedure specific for t-PA and plasminogen, wherein said affinity-depletion procedure uses a molecule that specifically binds tPA and plasminogen; and
   (ii) recovering the t-PA-deficient and/or plasminogen-deficient blood-derived product obtained in step (i).

34. The method according to claim 33, wherein the molecule that specifically binds tPA and plasminogen is at least one of 4-(aminomethyl)-cyclo- hexane-carboxylic acid (tranexamic acid), ε-amino caproic acid, lysine, anti-plasminogen antibodies and anti-tPA antibodies.

* * * * *